(12) United States Patent
Corper et al.

(10) Patent No.: US 12,060,436 B2
(45) Date of Patent: Aug. 13, 2024

(54) ENGINEERED IMMUNOGLOBULIN HEAVY CHAIN-LIGHT CHAIN PAIRS AND USES THEREOF

(71) Applicant: Zymeworks BC INC., Vancouver (CA)

(72) Inventors: Adam Louis Corper, Vancouver (CA); Dunja Urosev, Vancouver (CA); Stacey A. L. Tom-Yew, New Westminster (CA); Dustin Weyland Blue Bleile, Vancouver (CA); Thomas Spreter Von Kreudenstein, Vancouver (CA); Surjit Dixit, Richmond (CA); Paula Irene Lario, Vancouver (CA); Mario Sanches, Vancouver (CA)

(73) Assignee: ZYMEWORKS BC INC., Vancouver (CA)

( * ) Notice: Subject to any disclaimer, the term of this patent is extended or adjusted under 35 U.S.C. 154(b) by 331 days.

(21) Appl. No.: 17/343,198

(22) Filed: Jun. 9, 2021

(65) Prior Publication Data

US 2021/0309760 A1    Oct. 7, 2021

Related U.S. Application Data

(62) Division of application No. 15/896,170, filed on Feb. 14, 2018, now Pat. No. 11,078,296, which is a division of application No. 14/092,804, filed on Nov. 27, 2013, now Pat. No. 9,914,785.

(60) Provisional application No. 61/761,641, filed on Feb. 6, 2013, provisional application No. 61/730,906, filed on Nov. 28, 2012.

(51) Int. Cl.
*C07K 16/36*    (2006.01)

(52) U.S. Cl.
CPC .......... *C07K 16/36* (2013.01); *C07K 2317/55* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,624,821 | A | 4/1997 | Winter et al. |
| 5,731,168 | A | 3/1998 | Carter et al. |
| 5,807,706 | A | 9/1998 | Carter et al. |
| 5,821,333 | A | 10/1998 | Carter et al. |
| 5,885,573 | A | 3/1999 | Bluestone et al. |
| 6,194,551 | B1 | 2/2001 | Idusogie et al. |
| 6,268,488 | B1 | 7/2001 | Barbas et al. |
| 6,331,415 | B1 | 12/2001 | Cabilly et al. |
| 6,737,056 | B1 | 5/2004 | Presta |
| 6,809,185 | B1 | 10/2004 | Schoonjans et al. |
| 7,183,076 | B2 | 2/2007 | Arathoon et al. |
| 7,635,472 | B2 | 12/2009 | Kufer et al. |
| 7,642,228 | B2 | 1/2010 | Carter et al. |
| 7,695,936 | B2 | 4/2010 | Carter et al. |
| 7,769,573 | B2 | 8/2010 | Fejes et al. |
| 7,923,221 | B1 | 4/2011 | Cabilly et al. |
| 7,947,271 | B2 | 5/2011 | Browning et al. |
| 7,951,917 | B1 | 5/2011 | Arathoon et al. |
| 8,501,185 | B2 | 8/2013 | Heitner Hansen et al. |
| 8,592,562 | B2 | 11/2013 | Kannan et al. |
| 8,623,361 | B2 | 1/2014 | Beirnaert et al. |
| 8,771,988 | B2 | 7/2014 | Goepfert et al. |
| 9,079,965 | B2 | 7/2015 | Zhou et al. |
| 9,499,634 | B2 | 11/2016 | Dixit et al. |
| 9,527,927 | B2 | 12/2016 | Chowdhury et al. |
| 9,562,109 | B2 | 2/2017 | Von Kreudenstein et al. |
| 9,574,010 | B2 | 2/2017 | Spreter Von Kreudenstein et al. |
| 9,708,388 | B2 | 7/2017 | Beckmann |

(Continued)

FOREIGN PATENT DOCUMENTS

| | | |
|---|---|---|
| AU | 2013351888 | 6/2015 |
| AU | 2013351888 | 9/2018 |

(Continued)

OTHER PUBLICATIONS

Briney et al., Nature 566: 393 (Year: 2019).*
Piche-Nicholas et al., MABS 10(1): 81-94 (Year: 2018).*
Spiess et al., Molecular Immunology 67: 95-106 (Year: 2015).*
U.S. Appl. No. 15/896,170, "Notice of Allowability", Jun. 9, 2021, 2 pages.
U.S. Appl. No. 16/122,417, "Ex-Parte Quayle Action", Jul. 8, 2021, 8 pages.
U.S. Appl. No. 16/122,417, "Notice of Allowance", Oct. 18, 2021, 8 pages.
Arnau J. et al., Current strategies for the use of affinity tags and tag removal for the purification of recombinant proteins, Protein expression and purification, 2006, V. 48, N. 1, pp. 1-13, all text, p. 2 in particular.

(Continued)

*Primary Examiner* — Phuong Huynh
(74) *Attorney, Agent, or Firm* — Kilpatrick Townsend & Stockton LLP

(57) ABSTRACT

Provided are heterodimer pairs comprising a first heterodimer and a second heterodimer wherein each heterodimer comprises an immunoglobulin heavy chain or fragment thereof and an immunoglobulin light chain. At least one of the heterodimers comprises amino acid modifications in the $C_{H1}$ and/or $C_L$ domains, amino acid modifications in the $V_H$ and/or $V_L$ domains or a combination thereof. The modified amino acid residues are part of the interface between the light chain and heavy chain and are modified in order to create preferential pairing between each heavy chain and a desired light chain such that when the two heavy chains and two light chains of the heterodimer pair are co-expressed in a mammalian cell, the heavy chain of the first heterodimer preferentially pairs with one of the light chains rather than the other. Likewise, the heavy chain of the second heterodimer preferentially pairs with the second light chain rather than first.

14 Claims, 8 Drawing Sheets

(56) References Cited

U.S. PATENT DOCUMENTS

| | | |
|---|---|---|
| 9,732,155 B2 | 8/2017 | Spreter Von Kreudenstein et al. |
| 9,771,573 B2 | 9/2017 | Ohrn et al. |
| 9,914,785 B2* | 3/2018 | Corper .................. C07K 16/36 |
| 9,988,460 B2 | 6/2018 | Spreter Von Kreudenstein et al. |
| 10,000,576 B1 | 6/2018 | Weisser et al. |
| 10,077,298 B2* | 9/2018 | Corper .................. G16B 40/10 |
| 10,392,438 B2 | 8/2019 | Bennett et al. |
| 10,457,742 B2 | 10/2019 | Spreter Von Kreudenstein et al. |
| 10,508,154 B2 | 12/2019 | Dixit et al. |
| 11,078,296 B2* | 8/2021 | Corper .................. C07K 16/36 |
| 11,161,915 B2 | 11/2021 | Urosev et al. |
| 11,286,293 B2* | 3/2022 | Corper .................. A61P 35/00 |
| 11,306,156 B2* | 4/2022 | Sanches ................ C07K 16/32 |
| 2003/0003502 A1 | 1/2003 | Jardetzky et al. |
| 2003/0129659 A1 | 7/2003 | Whelihan et al. |
| 2003/0190311 A1 | 10/2003 | Dall'Acqua et al. |
| 2004/0071696 A1 | 4/2004 | Adams et al. |
| 2005/0069549 A1 | 3/2005 | Herman |
| 2005/0227324 A1 | 10/2005 | Huang et al. |
| 2005/0273247 A1 | 12/2005 | Lyakir et al. |
| 2006/0074225 A1 | 4/2006 | Chamberlain et al. |
| 2006/0106905 A1 | 5/2006 | Chren, Jr. |
| 2006/0136184 A1 | 6/2006 | Gustafsson et al. |
| 2006/0160184 A1 | 7/2006 | Mattheus Hoogenboom et al. |
| 2006/0263882 A1 | 11/2006 | Fazio et al. |
| 2007/0041987 A1 | 2/2007 | Carter et al. |
| 2007/0196363 A1 | 8/2007 | Arathoon et al. |
| 2007/0274985 A1 | 11/2007 | Dubel et al. |
| 2007/0276791 A1 | 11/2007 | Fejes et al. |
| 2007/0278170 A1 | 12/2007 | Wiebe |
| 2008/0050370 A1 | 2/2008 | Glaser et al. |
| 2008/0147360 A1 | 6/2008 | Fejes et al. |
| 2009/0162360 A1 | 6/2009 | Klein et al. |
| 2009/0182127 A1 | 7/2009 | Kjaergaard et al. |
| 2009/0226466 A1 | 9/2009 | Fong et al. |
| 2009/0232811 A1 | 9/2009 | Klein et al. |
| 2009/0263392 A1 | 10/2009 | Igawa et al. |
| 2010/0015133 A1 | 1/2010 | Igawa et al. |
| 2010/0032293 A1 | 2/2010 | Pollack et al. |
| 2010/0075326 A1 | 3/2010 | Jin et al. |
| 2010/0104564 A1 | 4/2010 | Hansen et al. |
| 2010/0105874 A1 | 4/2010 | Schuurman et al. |
| 2010/0149876 A1 | 6/2010 | Mokhlesi |
| 2010/0166749 A1 | 7/2010 | Presta |
| 2010/0196265 A1 | 8/2010 | Adams et al. |
| 2010/0256338 A1 | 10/2010 | Brinkmann et al. |
| 2010/0286374 A1 | 11/2010 | Kannan et al. |
| 2010/0322934 A1 | 12/2010 | Imhof-Jung et al. |
| 2010/0322935 A1 | 12/2010 | Croasdale et al. |
| 2010/0331243 A1 | 12/2010 | Davis et al. |
| 2011/0008345 A1 | 1/2011 | Ashman et al. |
| 2011/0053261 A1 | 3/2011 | Lario et al. |
| 2011/0059076 A1 | 3/2011 | McDonagh et al. |
| 2011/0200596 A1 | 8/2011 | Huang et al. |
| 2011/0274691 A1 | 11/2011 | Arvedson et al. |
| 2011/0275787 A1 | 11/2011 | Kufer et al. |
| 2011/0287009 A1 | 11/2011 | Scheer et al. |
| 2011/0293613 A1 | 12/2011 | Brinkmann et al. |
| 2012/0003221 A1 | 1/2012 | Mcdonagh et al. |
| 2012/0076728 A1 | 3/2012 | Wu et al. |
| 2012/0143580 A1 | 6/2012 | Constantine et al. |
| 2012/0149876 A1 | 6/2012 | Von Kreudenstein et al. |
| 2012/0244577 A1 | 9/2012 | Dixit et al. |
| 2012/0244578 A1 | 9/2012 | Kannan et al. |
| 2012/0270801 A1 | 10/2012 | Frejd et al. |
| 2013/0078249 A1 | 3/2013 | Ast et al. |
| 2013/0195849 A1 | 8/2013 | Spreter Von Kreudenstein et al. |
| 2013/0238299 A1 | 9/2013 | Ohrn |
| 2013/0245963 A1 | 9/2013 | Ohrn et al. |
| 2013/0336973 A1 | 12/2013 | Spreter Von Kreudenstein et al. |
| 2014/0051835 A1 | 2/2014 | Dixit et al. |
| 2014/0066378 A1 | 3/2014 | Dixit et al. |
| 2014/0066599 A2 | 3/2014 | Blein et al. |
| 2014/0072581 A1 | 3/2014 | Dixit et al. |
| 2014/0154253 A1 | 6/2014 | Ng et al. |
| 2014/0154254 A1 | 6/2014 | Kannan et al. |
| 2014/0179547 A1 | 6/2014 | Fischer et al. |
| 2014/0187753 A1 | 7/2014 | Blein et al. |
| 2014/0199294 A1 | 7/2014 | Mimoto et al. |
| 2014/0200331 A1 | 7/2014 | Corper et al. |
| 2014/0370020 A1 | 12/2014 | Kuramochi et al. |
| 2015/0051889 A1 | 2/2015 | Ohrn et al. |
| 2015/0125449 A1 | 5/2015 | Ng et al. |
| 2015/0142326 A1 | 5/2015 | Lakatos et al. |
| 2015/0211001 A1 | 7/2015 | Ohrn et al. |
| 2015/0220681 A1 | 8/2015 | Dixit |
| 2015/0284470 A1 | 10/2015 | Spreter Von Kreudenstein et al. |
| 2015/0307594 A1 | 10/2015 | Corper et al. |
| 2016/0083480 A1 | 3/2016 | Ng et al. |
| 2016/0114057 A1 | 4/2016 | Dixit et al. |
| 2016/0257763 A1 | 9/2016 | Von Kreudenstein et al. |
| 2016/0289328 A1 | 10/2016 | Ng et al. |
| 2016/0289335 A1 | 10/2016 | Weisser et al. |
| 2016/0297891 A1 | 10/2016 | Ng et al. |
| 2016/0355588 A1 | 12/2016 | Ng et al. |
| 2017/0158779 A1 | 6/2017 | Dixit et al. |
| 2017/0204199 A1 | 7/2017 | Sanches et al. |
| 2018/0016347 A1 | 1/2018 | Spreter Von et al. |
| 2018/0030150 A1 | 2/2018 | Spreter Von Kreudenstein et al. |
| 2018/0179296 A1 | 6/2018 | Corper et al. |
| 2018/0194860 A1 | 7/2018 | Von Kreudenstein et al. |
| 2018/0280429 A1 | 10/2018 | Wang et al. |
| 2019/0002589 A1 | 1/2019 | Bardroff et al. |
| 2019/0085055 A1 | 3/2019 | Corper et al. |
| 2019/0218311 A1 | 7/2019 | Loew et al. |
| 2019/0338048 A1 | 11/2019 | Urosev et al. |
| 2020/0087414 A1 | 3/2020 | Spreter Von Kreudenstein et al. |

FOREIGN PATENT DOCUMENTS

| | | |
|---|---|---|
| BR | 112016027888 | 10/2017 |
| BR | 112015012385 | 8/2019 |
| CA | 2548757 | 7/2005 |
| CN | 1176659 | 3/1998 |
| CN | 102153650 | 7/2012 |
| CN | 103261220 | 8/2013 |
| CN | 103429620 | 12/2013 |
| CN | 104114579 | 10/2014 |
| CN | 104640561 | 5/2015 |
| CN | 105026430 | 11/2015 |
| CN | 105121630 | 12/2015 |
| CN | 106661121 | 5/2017 |
| EA | 11879 | 6/2009 |
| EP | 368684 | 5/1990 |
| EP | 1870459 | 12/2007 |
| EP | 2543680 | 1/2013 |
| EP | 2635607 | 9/2013 |
| EP | 2647707 | 10/2013 |
| EP | 2635607 | 5/2014 |
| EP | 2925785 | 10/2015 |
| EP | 2925785 | 11/2016 |
| EP | 3107938 | 12/2016 |
| HK | 1200465 | 8/2015 |
| HK | 1216899 | 12/2016 |
| HK | 1217496 | 1/2017 |
| HK | 1231490 | 12/2017 |
| HK | 1237351 | 4/2018 |
| IN | 4953 | 11/2014 |
| IN | 1299 | 7/2015 |
| IN | 3768CHENP2015 | 7/2016 |
| IN | 201647044175 | 5/2017 |
| JP | 2009541275 | 11/2009 |
| JP | 2011504742 | 2/2011 |
| JP | 2011508604 | 3/2011 |
| JP | 2012512894 A | 6/2012 |
| JP | 2012525149 A | 10/2012 |
| JP | 2013536966 | 9/2013 |
| JP | 2013539461 | 10/2013 |
| JP | 2014504265 | 2/2014 |
| JP | 2014533243 | 12/2014 |
| JP | 2016508117 | 3/2016 |
| JP | 6347490 | 6/2018 |
| JP | 6351572 | 6/2018 |
| KR | 1020130135866 | 12/2013 |

(56) References Cited

FOREIGN PATENT DOCUMENTS

| | | |
|---|---|---|
| RU | 2015125486 | 1/2017 |
| WO | 9308829 | 5/1993 |
| WO | 9404690 | 3/1994 |
| WO | 9627011 | 9/1996 |
| WO | 9734631 | 9/1997 |
| WO | 9937791 | 7/1999 |
| WO | 9958572 | 11/1999 |
| WO | 0042072 | 7/2000 |
| WO | 03031464 | 4/2003 |
| WO | 2004029207 | 4/2004 |
| WO | 2004068820 | 8/2004 |
| WO | 2005018629 | 3/2005 |
| WO | 2006003388 | 1/2006 |
| WO | 2006030220 | 3/2006 |
| WO | 2006064136 | 6/2006 |
| WO | 2006106905 | 10/2006 |
| WO | 2007110205 | 10/2007 |
| WO | 2007147901 | 12/2007 |
| WO | 2008131242 | 10/2008 |
| WO | 2008141449 | 11/2008 |
| WO | 2009089004 | 7/2009 |
| WO | 2010068722 | 6/2010 |
| WO | 2010085682 | 7/2010 |
| WO | 2010112194 | 10/2010 |
| WO | 2010115553 | 10/2010 |
| WO | 2011005621 | 1/2011 |
| WO | 2011028952 | 3/2011 |
| WO | 2011034605 | 3/2011 |
| WO | 2011063348 | 5/2011 |
| WO | 2011066655 | 6/2011 |
| WO | 2011119484 | 9/2011 |
| WO | 2011120134 | 10/2011 |
| WO | 2011120135 | 10/2011 |
| WO | 2011131746 | 10/2011 |
| WO | 2011131749 | 10/2011 |
| WO | 2011143545 | 11/2011 |
| WO | 2011133886 | 12/2011 |
| WO | 2011147982 | 12/2011 |
| WO | 2012006635 | 1/2012 |
| WO | 2012020096 | 2/2012 |
| WO | 2012023053 | 2/2012 |
| WO | 2012037659 | 3/2012 |
| WO | 2012040833 | 4/2012 |
| WO | 2012058768 | 5/2012 |
| WO | 2012073985 | 6/2012 |
| WO | 2012116453 | 9/2012 |
| WO | 2012131555 | 10/2012 |
| WO | 2012143523 | 10/2012 |
| WO | 2012163519 | 12/2012 |
| WO | 2013002362 | 1/2013 |
| WO | 2013005194 | 1/2013 |
| WO | 2013060867 | 5/2013 |
| WO | 2013063702 | 5/2013 |
| WO | 2013065708 | 5/2013 |
| WO | 2013096291 | 6/2013 |
| WO | 2013166594 | 11/2013 |
| WO | 2013166604 | 11/2013 |
| WO | 2014004586 | 1/2014 |
| WO | 2014005784 | 1/2014 |
| WO | 2014012082 | 1/2014 |
| WO | 2014012085 | 1/2014 |
| WO | 2014018572 | 1/2014 |
| WO | 2014055784 | 4/2014 |
| WO | 2014067011 | 5/2014 |
| WO | 2014081955 | 5/2014 |
| WO | 2014082179 | 6/2014 |
| WO | 2014124326 | 8/2014 |
| WO | 2014150973 | 9/2014 |
| WO | 2014182970 | 11/2014 |
| WO | 2014186905 | 11/2014 |
| WO | 2015006749 | 1/2015 |
| WO | 2015052230 | 4/2015 |
| WO | 2015173756 | 11/2015 |
| WO | 2015181805 | 12/2015 |
| WO | 2015181805 | 2/2016 |
| WO | 2016026943 | 2/2016 |
| WO | 2016172485 | 10/2016 |
| WO | 2017059551 | 4/2017 |
| WO | 2017117179 | 7/2017 |
| WO | 2018057955 | 3/2018 |
| WO | 2018141894 | 8/2018 |
| WO | 2018158719 | 9/2018 |

OTHER PUBLICATIONS

Safdari Y. et al., Antibody humanization methods- and review and update. Biotechnology and Genetic Engineering Reviews, 2013, V. 29, N. 2, pp. 175-186, pp. 178, 180.

Shen J. et al., Single variable domain-IgG fusion: a novel recombinant approach to Fc domain-containing bispecific antibodies, Journal of Biological Chemistry, 2006, V. 281, N. 16, p. 10706-10714, p. 10713.

Zhu Z. et al., Engineering high affinity humanized anti-p185HER2/anti-CD3 bispecific F (ab') 2 for efficient lysis of p185HER2 overexpressing tumor cells, International journal of cancer, 1995, V. 62, N. 3, p. 319-324, p. 322.

Torres M. et al., The immunoglobulin constant region contributes to affinity and specificity, Trends in immunology, 2008, V. 29, N. 2, p. 91-97, p. 93-94.

Pakula A.A. et al. Genetic analysis of protein stability and function, Annual review of genetics, 1989, V. 23, N, 1, p. 289-310, p. 305-306.

Gasser B. et al., Antibody production with yeasts and filamentous fungi: on the road to large scale? Biotechnology letters, 2007, V. 29, N. 2, pp. 201-212, see p. 208.

Martin A. S. R., Protein sequence and structure analysis of antibody variable domains, Antibody engineering, Springer, Berlin, Heidelberg, 2010, p. 33-51, pp. 44-45.

"NCI Dictionary of Cancer Terms", National Cancer Institute, Accessed from Internet at Aug. 24, 2018, 70 pages.

U.S. Appl. No. 13/289,934, Advisory Action, Mailed on Feb. 5, 2016, 5 pages.

U.S. Appl. No. 13/289,934, Final Office Action, Mailed on Nov. 16, 2015, 19 pages.

U.S. Appl. No. 13/289,934, Non-Final Office Action, Mailed on Feb. 27, 2015, 15 pages.

U.S. Appl. No. 13/289,934, Non-Final Office Action, Mailed on May 13, 2015, 17 pages.

U.S. Appl. No. 13/289,934, Notice of Allowance, Mailed on Apr. 25, 2016, 9 pages.

U.S. Appl. No. 13/289,934, Notice of Allowance, Mailed on Sep. 29, 2016, 9 pages.

U.S. Appl. No. 13/289,934, "Restriction Requirement", Sep. 16, 2014, 6 pages.

U.S. Appl. No. 13/668,098, Final Office Action, Mailed on Nov. 17, 2015, 16 pages.

U.S. Appl. No. 13/668,098, Non-Final Office Action, Mailed on Apr. 3, 2015, 18 pages.

U.S. Appl. No. 13/668,098, Notice of Allowance, Mailed on Sep. 23, 2016, 12 pages.

U.S. Appl. No. 13/668,098, "Restriction Requirement", Dec. 5, 2014, 10 pages.

U.S. Appl. No. 13/892,198, Non-Final Office Action, Mailed on Oct. 6, 2015, 23 pages.

U.S. Appl. No. 13/892,198, "Restriction Requirement", Jul. 10, 2015, 12 pages.

U.S. Appl. No. 13/927,065, Final Office Action, Mailed on Feb. 22, 2016, 6 pages.

U.S. Appl. No. 13/927,065, Non-Final Office Action, Mailed on Oct. 7, 2015, 10 pages.

U.S. Appl. No. 13/927,065, Notice of Allowance, Mailed on Aug. 26, 2016, 7 pages.

U.S. Appl. No. 13/927,065, "Restriction Requirement", Apr. 15, 2015, 9 pages.

U.S. Appl. No. 13/941,449, Advisory Action, Mailed on Mar. 30, 2017, 5 pages.

U.S. Appl. No. 13/941,449, Final Office Action, Mailed on Jul. 24, 2018, 19 pages.

(56) References Cited

OTHER PUBLICATIONS

U.S. Appl. No. 13/941,449, Final Office Action, Mailed on Oct. 31, 2016, 58 pages.
U.S. Appl. No. 13/941,449, Non-Final Office Action, Mailed on Dec. 21, 2017, 18 pages.
U.S. Appl. No. 13/941,449, Non-Final Office Action, Mailed on Apr. 13, 2016, 41 pages.
U.S. Appl. No. 13/941,449, "Restriction Requirement", Dec. 3, 2015, 10 pages.
U.S. Appl. No. 13/949,166, Advisory Action, Mailed on Sep. 28, 2016, 3 pages.
U.S. Appl. No. 13/949,166, Final Office Action, Mailed on Aug. 21, 2015, 12 pages.
U.S. Appl. No. 13/949,166, Final Office Action, Mailed on Jun. 16, 2016, 19 pages.
U.S. Appl. No. 13/949,166, Final Office Action, Mailed on May 11, 2017, 21 pages.
U.S. Appl. No. 13/949,166, Non-Final Office Action, Mailed on Jan. 13, 2016, 12 pages.
U.S. Appl. No. 13/949,166, Non-Final Office Action, Mailed on Apr. 14, 2015, 22 pages.
U.S. Appl. No. 13/949,166, Non-Final Office Action, Mailed on Oct. 28, 2016, 24 pages.
U.S. Appl. No. 13/949,166, "Restriction Requirement", Dec. 16, 2014, 9 pages.
U.S. Appl. No. 14/092,804, Final Office Action, Mailed on Dec. 29, 2016, 46 pages.
U.S. Appl. No. 14/092,804, Non-Final Office Action, Mailed on Sep. 10, 2015, 33 pages.
U.S. Appl. No. 14/092,804, Notice of Allowance, Mailed on Nov. 1, 2017, 10 pages.
U.S. Appl. No. 14/092,804, "Restriction Requirement", Jun. 18, 2015, 5 pages.
U.S. Appl. No. 14/092,804, "Restriction Requirement", May 12, 2016, 5 pages.
U.S. Appl. No. 14/399,789, Final Office Action, Mailed on Jul. 20, 2016, 30 pages.
U.S. Appl. No. 14/399,789, Non-Final Office Action, Mailed on Dec. 17, 2015, 31 pages.
U.S. Appl. No. 14/399,789, "Restriction Requirement", Sep. 14, 2015, 11 pages.
U.S. Appl. No. 14/432,153, "Corrected Notice of Allowability", Aug. 18, 2017, 7 pages.
U.S. Appl. No. 14/432,153, Non-Final Office Action, Mailed on Oct. 27, 2016, 10 pages.
U.S. Appl. No. 14/432,153, Notice of Allowance, Mailed on May 15, 2017, 8 pages.
U.S. Appl. No. 14/432,153, "Restriction Requirement", Jun. 30, 2016, 7 pages.
U.S. Appl. No. 14/439,532, Notice of Allowance, Mailed on Mar. 1, 2017,.
U.S. Appl. No. 14/439,532, Notice of Allowance, Mailed on Feb. 9, 2017, 11 pages.
U.S. Appl. No. 14/439,532, Notice of Allowance, Mailed on May 19, 2017, 9 pages.
U.S. Appl. No. 14/439,532, "Restriction Requirement", Nov. 8, 2011, 7 pages.
U.S. Appl. No. 14/648,222, Advisory Action, Mailed on Apr. 20, 2018, 3 pages.
U.S. Appl. No. 14/648,222, Final Office Action, Mailed on Dec. 29, 2017, 12 pages.
U.S. Appl. No. 14/648,222, Non-Final Office Action, Mailed on May 16, 2017, 43 pages.
U.S. Appl. No. 14/648,222, Notice of Allowance, Mailed on May 8, 2018, 7 pages.
U.S. Appl. No. 14/648,222, "Restriction Requirement", May 9, 2016, 14 pages.
U.S. Appl. No. 14/648,222, "Restriction Requirement", Dec. 2, 2016, 33 pages.
U.S. Appl. No. 14/888,580, Final Office Action, Mailed on Sep. 7, 2017, 11 pages.
U.S. Appl. No. 14/888,580, Final Office Action, Mailed on Aug. 7, 2018, 16 pages.
U.S. Appl. No. 14/888,580, Non-Final Office Action, Mailed on Mar. 1, 2018, 11 pages.
U.S. Appl. No. 14/888,580, Non-Final Office Action, Mailed on Apr. 12, 2017, 16 pages.
U.S. Appl. No. 14/888,580, Notice of Allowance, Mailed on Nov. 15, 2018, 8 pages.
U.S. Appl. No. 14/888,580, "Restriction Requirement", Jan. 30, 2017, 10 pages.
U.S. Appl. No. 14/888,580, "U.S. Patent Application", Bispecific HER2 and HER3 Antigen Binding Constructs, filed Nov. 2, 2015.
U.S. Appl. No. 14/893,706, Final Office Action, Mailed on Dec. 1, 2017, 17 pages.
U.S. Appl. No. 14/893,706, Non-Final Office Action, Mailed on Jun. 30, 2017, 15 pages.
U.S. Appl. No. 14/893,706, "Restriction Requirement", Aug. 24, 2018, 6 pages.
U.S. Appl. No. 14/893,706, "Restriction Requirement", Apr. 4, 2017, 8 pages.
U.S. Appl. No. 14/893,706, "U.S. Patent Application", Modular Protein Drug Conjugate Therapeutic, filed Nov. 24, 2015.
U.S. Appl. No. 14/903,184, "Bispecific CD3 and CD19 Antigen Binding Constructs", U.S. Patent Application filed Jan. 6, 2016.
U.S. Appl. No. 14/903,184, Non-Final Office Action, Mailed on Feb. 2, 2018, 30 pages.
U.S. Appl. No. 14/903,184, "Restriction Requirement", Jun. 23, 2017, 12 pages.
U.S. Appl. No. 14/989,648, Final Office Action, Mailed on Sep. 26, 2018, 13 pages.
U.S. Appl. No. 14/989,648, Non-Final Office Action, Mailed on Sep. 25, 2018, 13 pages.
U.S. Appl. No. 14/989,648, Non-Final Office Action, Mailed on Mar. 29, 2019, 15 pages.
U.S. Appl. No. 14/989,648, Non-Final Office Action, Mailed on Apr. 18, 2018, 19 pages.
U.S. Appl. No. 14/989,648, "Restriction Requirement", Jan. 9, 2018, 6 pages.
U.S. Appl. No. 14/989,648, "U.S. Appl. No.", Heteromultimer Constructs of Immunoglobulin Heavy Chains With Mutations in the Fc Domain, filed Jan. 6, 2016, 247 pages.
U.S. Appl. No. 15/036,174, Non Final Office Action, Mailed on Jul. 5, 2018, 12 pages.
U.S. Appl. No. 15/036,174, Non-Final Office Action, Mailed on Dec. 14, 2017, 18 pages.
U.S. Appl. No. 15/036,174, Notice of Allowance, Mailed on Dec. 17, 2018, 3 pages.
U.S. Appl. No. 15/036,174, "Restriction Requirement", Jul. 20, 2017, 9 pages.
U.S. Appl. No. 15/036,174, "U.S. Appl. No.", filed May 12, 2016.
U.S. Appl. No. 15/036,175, Non Final Office Action, Mailed on Nov. 8, 2018, 9 pages.
U.S. Appl. No. 15/036,175, "Restriction Requirement", Jun. 28, 2018, 7 pages.
U.S. Appl. No. 15/036,175, "U.S. Appl. No.", filed May 12, 2016,.
U.S. Appl. No. 15/036,176, Non-Final Office Action, Mailed on Mar. 14, 2018, 21 pages.
U.S. Appl. No. 15/036,176, "Restriction Requirement", Jul. 28, 2017, 16 pages.
U.S. Appl. No. 15/036,176, "U.S. Appl. No.", filed May 12, 2016.
U.S. Appl. No. 15/298,625, Non-Final Office Action, Mailed on Jun. 1, 2018, 28 pages.
U.S. Appl. No. 15/298,625, "Restriction Requirement", Jan. 17, 2018, 15 pages.
U.S. Appl. No. 15/314,496, Final Office Action, Mailed on Jul. 28, 2020, 16 pages.
U.S. Appl. No. 15/314,496, Final Office Action, Mailed on Apr. 24, 2019, 24 pages.
U.S. Appl. No. 15/314,496, Non-Final Office Action, Mailed on Mar. 30, 2021, 12 pages.

(56) References Cited

OTHER PUBLICATIONS

U.S. Appl. No. 15/314,496 , Non-Final Office Action, Mailed on Jan. 6, 2020, 20 pages.
U.S. Appl. No. 15/314,496 , Non-Final Office Action, Mailed on Oct. 17, 2018, 20 pages.
U.S. Appl. No. 15/314,496 , "Restriction Requirement", May 8, 2018, 35 pages.
U.S. Appl. No. 15/355,019 , Non-Final Office Action, Mailed on Jan. 8, 2019, 5 pages.
U.S. Appl. No. 15/355,019 , Non-Final Office Action, Mailed on Jul. 21, 2017, 7 pages.
U.S. Appl. No. 15/355,019 , Notice of Allowance, Mailed on Jul. 29, 2019, 5 pages.
U.S. Appl. No. 15/355,019 , Notice of Allowance, Mailed on May 22, 2018, 6 pages.
U.S. Appl. No. 15/355,019 , Notice of Allowance, Mailed on Nov. 17, 2017, 8 pages.
U.S. Appl. No. 15/409,456 , Final Office Action, Mailed on Oct. 24, 2019, 7 pages.
U.S. Appl. No. 15/409,456 , Final Office Action, Mailed on May 13, 2020, 8 pages.
U.S. Appl. No. 15/409,456 , Non-Final Office Action, Mailed on May 23, 2019, 9 pages.
U.S. Appl. No. 15/409,456 , Notice of Allowance, Mailed on Aug. 27, 2020, 7 pages.
U.S. Appl. No. 15/409,456 , "Restriction Requirement", Jan. 10, 2019, 9 pages.
U.S. Appl. No. 15/411,799 , "Notice of Allowability", Jul. 10, 2019, 3 pages.
U.S. Appl. No. 15/411,799 , Notice of Allowance, Mailed on Jun. 10, 2019, 12 pages.
U.S. Appl. No. 15/411,799 , "Restriction Requirement", Jan. 25, 2019, 9 pages.
U.S. Appl. No. 15/526,888 , "U.S. Appl. No.", filed May 15, 2017.
U.S. Appl. No. 15/572,362 , "U.S. Appl. No.", filed Nov. 7, 2017.
U.S. Appl. No. 15/675,248 , Notice of Allowance, Mailed on Mar. 22, 2018, 22 pages.
U.S. Appl. No. 15/741,984 , "U.S. Appl. No.", filed Jan. 4, 2018.
U.S. Appl. No. 15/765,574 , Non-Final Office Action, Mailed on Dec. 27, 2019, 25 pages.
U.S. Appl. No. 15/765,574 , Notice of Allowance, Mailed on Sep. 2, 2020, 14 pages.
U.S. Appl. No. 15/765,574 , Notice of Allowance, Mailed on Apr. 26, 2021, 6 pages.
U.S. Appl. No. 15/765,574 , Notice of Allowance, Mailed on Jan. 27, 2021, 8 pages.
U.S. Appl. No. 15/765,574 , "Restriction Requirement", Sep. 10, 2019, 16 pages.
U.S. Appl. No. 15/896,170 , Final Office Action, Mailed on May 18, 2020, 6 pages.
U.S. Appl. No. 15/896,170 , Final Office Action, Mailed on Feb. 1, 2021, 8 pages.
U.S. Appl. No. 15/896,170 , Non-Final Office Action, Mailed on Sep. 18, 2019, 22 pages.
U.S. Appl. No. 15/896,170 , Notice of Allowance, Mailed on Mar. 30, 2021, 7 pages.
U.S. Appl. No. 15/896,170 , "Restriction Requirement", Jun. 26, 2019, 9 pages.
U.S. Appl. No. 16/122,417 , Final Office Action, Mailed on Feb. 8, 2021, 18 pages.
U.S. Appl. No. 16/122,417 , Non-Final Office Action, Mailed on Jun. 19, 2020, 34 pages.
U.S. Appl. No. 16/122,417 , "Restriction Requirement", Mar. 6, 2020, 11 pages.
U.S. Appl. No. 16/568,611 , "U.S. Appl. No.", filed Sep. 12, 2019.
U.S. Appl. No. 17/107,217 , "U.S. Appl. No.", filed Nov. 30, 2020.
Alegre et al., "A Non-activating "Humanized" Anti-CD3 Monoclonal Antibody Retains Immunosuppressive Properties in Vivo", Transplantation, vol. 57, No. 11, Jun. 15, 1994, pp. 1537-1543.
Altintas et al., "Targeting Epidermal Growth Factor Receptor in Tumors: From Conventional Monoclonal Antibodies via Heavy Chain-only Antibodies to Nanobodies", Eur J Pharm Sci., vol. 45, No. 4, Mar. 12, 2012, pp. 399-407.
Altman et al., "Copy Number Polymorphism in Fcgr3 Predisposes to Glomerulonephritis in Rats and Humans", Nature, vol. 439, No. 7078, Feb. 16, 2006, pp. 851-855.
Arnau et al., "Current Strategies for the Use of Affinity Tags and Tag Removal for the Purification of Recombinant Proteins", Protein Expression and Purification, vol. 48, No. 1, Jul. 2006, pp. 1-13.
Arnold et al., "The Impact of Glycosylation on the Biological Function and Structure of Human Immunoglobulins", Annu Rev Immunol., vol. 25, Apr. 23, 2007, pp. 21-50.
Atwell et al., "Stable Heterodimers from Remodeling the Domain Interface of a Homodimer Using a Phage Display Library", Journal of Molecular Biology, vol. 270, No. 1, Jul. 4, 1997, pp. 26-35.
Application No. AU2011325833 , First Examiner Report, Mailed on May 17, 2016, 3 pages.
Application No. AU2012332021 , First Examiner Report, Mailed on Jan. 10, 2017, 5 pages.
Application No. AU2013258834 , First Examiner Report, Mailed on Mar. 6, 2017, 4 pages.
AU2013351888 , "First Examination Report", Dec. 19, 2017, 4 pages.
Application No. AU2013351888 , Notice of Allowance, Mailed on May 9, 2018, 3 pages.
AU2015265457 , "First Examination Report", Feb. 21, 2020, 4 pages.
AU2015265457 , "Second Examination Report", Dec. 11, 2020, 3 pages.
AU2018220048 , "First Examination Report", Jun. 21, 2019, 11 pages.
AU2018220048 , "Second Examination Report", May 18, 2020, 3 pages.
Barthelemy et al., "Comprehensive Analysis of the Factors Contributing to the Stability and Solubility of Autonomous Human Vh Domains", J. Bioi. Chem., vol. 283, No. 6, Feb. 8, 2008, pp. 3639-3654.
Beck et al., "Strategies and Challenges for the Next Generation of Therapeutic Antibodies", Nature Reviews Immunology, vol. 10, No. 5, May 2010, pp. 345-352.
Beckman et al., "Antibody Constructs in Cancer Therapy", Protein Engineering Strategies to Improve Exposure in Solid Tumors, vol. 109, Jan. 15, 2007, pp. 170-179.
Bell et al., "Differential Tumor-targeting Abilities of Three Single-domain Antibody Formats", Cancer Letters, vol. 289, No. 1, Mar. 1, 2010, pp. 81-90.
Bolon et al., "Specificity Versus Stability in Computational Protein Design", Proceedings of the National Academy of Sciences, vol. 102, No. 36, Sep. 6, 2005, pp. 12724-12749.
Application No. BR112015012385-6 , Office Action, Mailed on Dec. 23, 2020.
Application No. BR1120160278887 , Office Action, Mailed on Dec. 16, 2020.
Application No. BR112018007152-8 , Office Action, Mailed on Mar. 23, 2021, 4 pages.
Braden , "Structural Features of the Reactions Between Antibodies and Protein Antigens", The FASEB Journal, vol. 9, Issue 1, Jan. 1995, pp. 9-16.
Application No. CA2,872,540 , Office Action, Mailed on Feb. 18, 2019, 4 pages.
Application No. CA2,893,562 , Office Action, Mailed on Dec. 15, 2020, 5 pages.
Application No. CA2,893,562 , Office Action, Mailed on Oct. 22, 2019, 9 pages.
Carter et al., "Humanization of an Anti-p185HER2 Antibody for Human Cancer Therapy", Proceedings of the National Academy of Sciences of the United States of America, vol. 89, No. 10, May 1992, pp. 4285-4289.
Carter , "Introduction to Current and Future Protein Therapeutics: a Protein Engineering Perspective", Experimental Cell Research, vol. 317, No. 9, May 15, 2011, pp. 1261-1269.

(56) References Cited

OTHER PUBLICATIONS

Cespedes et al., "Mouse Models in Oncogenesis and Cancer Therapy", Clinical and Translational Oncology, vol. 8, No. 5, May 2006, pp. 318-329.
Chames et al., "Therapeutic Antibodies: Successes, Limitations and Hopes for the Future", British Journal of Pharmacology, vol. 157, No. 2, May 2009, pp. 220-233.
Chen et al., "Preferential Germline Usage and VH/VL Pairing Observed in Human Antibodies Selected by mRNA Display", Protein Engineering, Design & Selection : PEDS, vol. 28, No. 10, 2015, pp. 427-435.
Application No. CN201180064119 .X , Office Action, Mailed on Aug. 5, 2014, 9 pages.
Application No. CN201180064119.X , Office Action, Mailed on Nov. 27, 2015, 1 page.
Application No. CN201180064119.X , Office Action, Mailed on Dec. 19, 2016, 6 pages.
Application No. CN201180064119.X , Office Action, Mailed on Jul. 6, 2015, 8 pages.
Application No. CN201180064119.X , Office Action, Mailed on Jun. 7, 2016, 9 pages.
Application No. CN201280057691.8 , Office Action, Mailed on Jul. 4, 2016, 11 pages.
Application No. CN201280057691.8 , Office Action, Mailed on Oct. 19, 2015, 21 pages.
Application No. CN201380036538.1 , Office Action, Mailed on Jul. 19, 2016, 12 pages.
Application No. CN201380062006.5 , Office Action, Mailed on Jun. 9, 2017, 14 pages.
Application No. CN201380062006.5 , Office Action, Mailed on Jan. 29, 2018, 5 pages.
Application No. CN201380062006.5 , Office Action, Mailed on Mar. 26, 2020, 8 pages.
Application No. CN201380062006.5 , Office Action, Mailed on Aug. 30, 2018, 9 pages.
Application No. CN201380063081.3 , Office Action, Mailed on Mar. 17, 2017, 7 pages.
Application No. CN201580036617.1 , Office Action, Mailed on Dec. 1, 2020, 18 pages.
Application No. CN201580036617.1 , Office Action, Mailed on Jan. 3, 2020, 27 pages.
Application No. CN201680061001.4 , Office Action, Mailed on Feb. 26, 2021, 27 pages.
Cochlovius et al., "Treatment of Human B Cell Lymphoma Xenografts with a CD3 X CD19 Diabody and T Cells", Journal of Immunology, vol. 165, No. 2, Jul. 15, 2000, pp. 888-895.
Colbere-Garapin et al., "A New Dominant Hybrid Selective Marker for Higher Eukaryotic Cell", Journal of Molecular Biology, vol. 150, No. 1, Jul. 25, 1981, pp. 1-14.
Colman , "Effects of Amino Acid Sequence Changes on Antibody-antigen Interactions", Research in Immunology, vol. 145, No. 1, Jan. 1994, pp. 33-36.
Coloma et al., "Design and Production of Novel Tetravalent Bispecific Antibodies", Nature Biotechnology, vol. 15, No. 2, Feb. 1997, pp. 159-163.
Dall'Acqua et al., "Contribution of Domain Interface Residues to the Stability of Antibody CH3 Domain Homodimers", Biochemistry, American Chemical Society, US, vol. 37, No. 26, Jun. 30, 1998, pp. 9266-9273.
Davis et al., "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies", Protein Engineering, Design & Selection, vol. 23, No. 4, Feb. 4, 2010, pp. 195-202.
De Kruif et al., "Leucine Zipper Dimerized Bivalent and Bispecific Scfv Antibodies From a Semi-Synthetic Antibody Phage Display Library", Journal of Biological Chemistry, vol. 271, No. 13, Mar. 29, 1996, pp. 7630-7634.

Demarest et al., "Antibody Therapeutics, Antibody Engineering, and the Merits of Protein Stability", Current Opinion in Drug Discovery and Development vol. 11, No. 5, Sep. 2008, pp. 675-687.
Demarest et al., "Optimization of the Antibody CH3 Domain by Residue Frequency Analysis of IgG Sequences", Journal of Molecular Biology, vol. 335, No. 1, Jan. 2, 2004, pp. 41-48.
Dennis , "Off by a Whisker", Nature, vol. 442, Aug. 17, 2006, pp. 739-741.
Deyev et al., "Modern Technologies for Creating Synthetic Antibodies for Clinical Application", Acta Naturae, vol. 1, No. 1, Apr. 2009, pp. 32-50.
Dockal et al., "Conformational Transitions of the Three Recombinant Domains of Human Serum Albumin Depending on pH", The Journal of Biological Chemistry, vol. 275, No. 5, Feb. 4, 2000, pp. 3042-3050.
Dockal et al., "Five Recombinant Fragments of Human Serum Albumin-tools for the Characterization of the Warfarin Binding Site", Protein Science, vol. 9, No. 8, Aug. 2000, pp. 1455-1465.
Ducry et al., "Antibody-drug Conjugates: Linking Cytotoxic Payloads to Monoclonal Antibodies", Bioconjugate Chem., vol. 21, No. 1, Jan. 2010, pp. 5-13.
Dufner et al., "Harnessing Phage and Ribosome Display for Antibody Optimisation", Trends in Biotechnology, vol. 24, No. 11, 2006, pp. 523-529.
Duncan et al., "Localization of the Binding Site for the Human High-affinity FC Receptor on IgG", Nature, vol. 332, No. 7, Apr. 7, 1988, pp. 563-564.
Durocher et al., "High-Level and High-Throughput Recombinant Protein Production by Transient Transfection of Suspension-Growing Human 293-EBNA1 Cells", Nucleic Acids Research, vol. 30, No. 2, Jan. 2002, 9 pages.
Application No. EA201692476 , Office Action, Mailed on Feb. 10, 2017, 2 pages.
Application No. EA201692476 , Office Action, Mailed on Nov. 21, 2018, 8 pages.
Edwards et al., "The Remarkable Flexibility of the Human Antibody Repertoire; Isolation of Over One Thousand Different Antibodies to a Single Protein, BLyS", Journal of Molecular Biology, vol. 334, No. 1, Nov. 14, 2003, pp. 103-118.
Application No. EP11837370.3 , Extended European Search Report, Mailed on Apr. 29, 2014, 14 pages.
Application No. EP11837370.3 , Office Action, Mailed on Mar. 22, 2016, 7 pages.
Application No. EP12845801.5 , Extended European Search Report, Mailed on May 8, 2015, 7 pages.
Application No. EP12845801.5 , Office Action, Mailed on Oct. 21, 2016, 4 pages.
Application No. EP13788302.1 , Extended European Search Report, Mailed on Nov. 18, 2015, 9 pages.
Application No. EP13788302.1 , Office Action, Mailed on Sep. 5, 2017, 3 pages.
Application No. EP13788302.1 , Office Action, Mailed on Apr. 10, 2019, 6 pages.
Application No. EP13788302.1 , Office Action, Mailed on Feb. 13, 2018, 6 pages.
Application No. EP13822129.6 , Extended European Search Report, Mailed on Dec. 1, 2015, 10 pages.
Application No. EP13843363.6 , Extended European Search Report, Mailed on May 11, 2016, 10 pages.
Application No. EP13858496.6 , Extended European Search Report, Mailed on Oct. 13, 2016, 19 pages.
Application No. EP13858496.6 , Office Action, Mailed on Jul. 1, 2016, 12 pages.
Application No. EP13858496.6 , Office Action, Mailed on Mar. 23, 2018, 5 pages.
Application No. EP13858496.6 , Office Action, Mailed on Sep. 23, 2020, 6 pages.
Application No. EP13858496.6 , Office Action, Mailed on Dec. 14, 2018, 7 pages.
Application No. EP13858496.6 , Office Action, Mailed on Apr. 30, 2020, 8 pages.
Application No. EP15799575.4 , Extended European Search Report, Mailed on Jan. 30, 2018, 17 pages.

(56) References Cited

OTHER PUBLICATIONS

Application No. EP15799575.4, Office Action, Mailed on Dec. 10, 2020, 4 pages.
Application No. EP15799575.4, Office Action, Mailed on Feb. 6, 2019, 6 pages.
EP15799575.4, "Partial Supplementary European Search Report", Oct. 30, 2017, 16 pages.
EP15799575.4, "Summons to Attend Oral Proceedings", Apr. 16, 2021, 5 pages.
EP15799575.4, "Summons to Attend Oral Proceedings", Feb. 27, 2020, 8 pages.
Application No. EP16852954.3, Extended European Search Report, Mailed on Jul. 31, 2019, 19 pages.
Application No. EP16852954.3, Office Action, Mailed on Dec. 21, 2020, 12 pages.
EP16852954.3, "Partial Supplementary European Search Report", Apr. 25, 2019, 21 pages.
Feng et al., "Dual Function Antibody Drug Substance Research Study Progress", Chinese Medical Bio Technology, vol. 9, No. 4, Aug. 2014, pp. 1-6.
Feng et al., "Research Progress of Bifunctional Antibody Drugs", Chinese Medical Biotechnology, vol. 9, No. 4, Aug. 31, 2014, pp. 291-293.
Ferguson, "A Structure-Based View of Epidermal Growth Factor Receptor Regulation", Annual Review of Biophysics, vol. 37, 2008, 23 pages.
Fischer et al., "Exploiting Light Chains for the Scalable Generation and Platform Purification of Native Human Bispecific IgG", Nature Communications, vol. 6, No. 6113, Feb. 12, 2015, pp. 1-12.
Fujimori et al., "A Modeling Analysis of Monoclonal Antibody Percolation Through Tumors: a Binding-site Barrier", J Nucl Med., vol. 3, No. 17, Jul. 1990, pp. 1191-1198.
Glockshuber et al., "A Comparison of Strategies to Stabilize Immunoglobulin Fv-Fragments", Biochemistry, vol. 29, 1990, pp. 1362-1367.
Grabulovski et al., "A Novel, Non-Immunogenic Fyn SH3-derived Binding Protein With Tumor Vascular Targeting Properties", J Bioi Chem., vol. 282, No. 5, Feb. 2007, pp. 3196-3204.
Gramer et al., "Production of Stable Bispecific LgG1 by Controlled Fab-Arm Exchange", mAbs, vol. 5, No. 6, Nov.-Dec. 2013, pp. 962-973.
Groot et al., "Identification by Phage Display of Single-domain Antibody Fragments Specific for the Odd Domain in Hypoxia-inducible Factor 1 Alpha", Lab Invest vol. 86, No. 4, Apr. 2006, pp. 345-356.
Gunasekaran et al., "Enhancing Antibody Fc Heterodimer Formation Through Electrostatic Steering Effects: Applications to Bispecific Molecules and Monovalent IgG", Journal of Biological Chemistry, vol. 285, No. 25, Jun. 18, 2010, pp. 19637-19646.
Guss et al., "Structure of the IgG-binding Regions of Streptococcal Protein G", The EMBO Journal, vol. 5, No. 7, Jul. 1986, pp. 1567-1575.
Hamel et al., "The Role of the VL- and VH-Segments in the Preferential Reassociation of Immunoglobulin Subunits", Molecular Immunology, vol. 23, No. 5, May 1986, pp. 503-510.
Hardy et al., "Valency of Antibody Binding to Enveloped Virus Particles as Determined by Surface Plasmon Resonance", Journal of Virology, vol. 77, No. 2, Jan. 2003, pp. 1649-1652.
Havranek et al., "Automated Design of Specificity in Molecular Recognition", Nature Structure Biology, vol. 10, No. 1, Jan. 2003, pp. 45-52.
Heads et al., "Relative Stabilities of Igg1 and Igg4 Fab Domains: Influence of The Light-heavy Interchain Disulfide Bond Architecture", Protein Science, vol. 21, No. 9, Jun. 28, 2012, pp. 1315-1322.
Hennecke et al., "Composition and Arrangement of Genes Define the Strength of IRES-driven Translation in Bicistronic mRNAs", Nucleic Acids Res., vol. 29, No. 16, Aug. 15, 2001, pp. 3327-3334.
Holt et al., "Domain Antibodies: Proteins for Therapy", Trends In Biotechnology vol. 21, No. 11, Nov. 2003, pp. 484-490.

Huang et al., "A De Novo Designed Protein Protein Interface", Protein Science, vol. 16, No. 12, Sep. 21, 2007, pp. 2770-2774.
Huang et al., "Recombinant Immuno-therapeutics: Current State and Perspectives Regarding the Feasibility and Market", Appl Microbiol Biotechnol, vol. 87, No. 2, Jun. 2010, pp. 401-410.
Hudson et al., "High Avidity Scfv Multimers; Diabodies and Triabodies", J. Immunol. Methods, vol. 231, No. 1-2, Dec. 10, 1999, pp. 177-189.
Hust et al., "Single Chain Fab (scFab) Fragment", BMC Biotechnology, vol. 7, No. 14, Available online at: http://www.biomedcentral.com/1472-6750/7/14, Mar. 8, 2007, pp. 1-15.
Hutchins et al., "Improved Biodistribution, Tumor Targeting, and Reduced Immunogenicity in Mice With a Gamma 4 Variant of Campath-1H", Proc. Natl. Acad. Sci., vol. 92, No. 26, Dec. 19, 1995, pp. 11980-11984.
Idusogie et al., "Engineered Antibodies With Increased Activity to Recruit Complement", J. Immunol., vol. 166, No. 4, Feb. 15, 2001, pp. 2571-2575.
Idusogie et al., "Mapping of the C1q Binding Site on Rituxan, a Chimeric Antibody With a Human IgG1 Fc", J. Immunol., vol. 164, No. 8, Apr. 15, 2000, pp. 4178-4184.
Igawa et al., "VH/VL Interface Engineering to Promote Selective Expression and Inhibit Conformational Isomerization of Thrombopoietin Receptor Agonist Single-Chain Diabody", Protein Engineering, Design and Selection, vol. 23, Issue 8, Aug. 2010, pp. 667-677.
IN201647044175, "First Examination Report", Apr. 16, 2021, 7 pages.
IN201847016378, "First Examination Report", Mar. 25, 2021, 9 pages.
IN3768/CHENP/2015, "First Examination Report", Aug. 22, 2019, 10 pages.
Inoue et al., "Efficient Production of a Functional Mouse/Human Chimeric Fab Against Human Urokinase-Type Plasminogen Activator by Bacillus Brevis", Appl Microbiol Biotechnol., vol. 48, No. 4, Oct. 1997, pp. 487-492.
Ionescu et al., "Contribution of Variable Domains to the Stability of Humanized IgG1 Monoclonal Antibodies", Journal of Pharmaceutical Sciences, vol. 97, No. 4, Apr. 2008, pp. 1414-1426.
Jackman et al., "Development of a Two-part Strategy to Identify a Therapeutic Human Bispecific Antibody That Inhibits IgE Receptor Signaling", J Biol Chem., vol. 285, No. 27, Jul. 2, 2010, pp. 20850-20859.
Jaeger, "Clinical Immunology and Allergology", Medicine, Second Edition, vol. 2, 1990, pp. 484-485.
Janeway et al., "Structure of the Antibody Molecule and Immunoglobulin Genes", Immuno Biology, the Immune System in Health and Disease, Third Edition, Garland Publishing Inc. Chapter 3, 1997, pp. 3:1-3:11.
Jefferis et al., "Interaction Sites on Human IgG-Fc for Fcgammar: Current Models", Immunol. Lett., vol. 82, No. 1-2, Jun. 3, 2002, pp. 57-65.
Jefferis et al., "Modulation of Fc(Gamma)R and Human Complement Activation by IgG3-core Oligosaccharide Interactions", Immunol. Lett., vol. 54, No. 2-3, Dec. 1996, pp. 101-104.
Jefferis et al., "Recognition Sites on Human IgG for Fc Gamma Receptors: the Role of Glycosylation", Immunol. Lett., vol. 44, No. 2-3, Jan. 1995, pp. 111-117.
Jin et al., "MetMAb, the One-armed 5D5 Anti-c-met Antibody, Inhibits Orthotopic Pancreatic Tumor Growth and Improves Survival", Cancer Res., vol. 68, No. 11, Jun. 1, 2008, pp. 4360-4368.
Jordan et al., "Structural Understanding of Stabilization Patterns in Engineered Bispecific Ig-like Antibody Molecules", Proteins, vol. 77, No. 4, Dec. 2009, pp. 832-841.
Application No. JP2013-536966, Office Action, Mailed on Aug. 18, 2016, 4 pages.
Application No. JP2013-536966, Office Action, Mailed on Dec. 7, 2015, 5 pages.
Application No. JP2014-539198, Office Action, Mailed on Aug. 22, 2016, 5 pages.
Application No. JP2015-510588, Notice of Decision to Grant, Mailed on May 9, 2018, 3 pages.
Application No. JP2015-510588, Office Action, Mailed on Nov. 2, 2017, 4 pages.

(56) References Cited

OTHER PUBLICATIONS

Application No. JP2015-510588, Office Action, Mailed on Mar. 16, 2017, 7 pages.
Application No. JP2015-535788, Office Action, Mailed on Sep. 4, 2017, 4 pages.
Application No. JP2015-544282, Notice of Decision to Grant, Mailed on Apr. 24, 2018, 4 pages.
Application No. JP2015-544282, Office Action, Mailed on Oct. 4, 2017, 7 pages.
Application No. JP2016-569603, Office Action, Mailed on Jun. 4, 2019, 12 pages.
Application No. JP2016-569603, Office Action, Mailed on Apr. 14, 2020, 6 pages.
Application No. JP2018-099261, Notice of Decision to Grant, Mailed on Oct. 20, 2020, 4 pages.
Application No. JP2018-099261, Office Action, Mailed on Apr. 21, 2020, 6 pages.
Application No. JP2018-099261, Office Action, Mailed on Jun. 11, 2019, 6 pages.
Application No. JP2018-517849, Office Action, Mailed on Sep. 15, 2020, 20 pages.
Jubala et al., "CD20 Expression in Normal Canine B Cells and in Canine non-Hodgkin Lymphoma", Vet Pathol, vol. 42, 2005, pp. 468-476.
Kabat et al., "Sequences of Proteins of Immunological Interest", Diane Publishing, Fifth Edition, NIH Publication No. 91-3242, 1991, pp. 647-657, 661-669.
Kaloff et al., "Coordination of Immunoglobulin Chain Folding and Immunoglobulin Chain Assembly is Essential for the Formation of Functional IgG", Immunity, vol. 2, Jun. 1995, pp. 629-637.
Kang et al., "Engineering Multivalent Antibodies to Target Heregulin-Induced HER3 Signaling in Breast Cancer Cells", MABs, vol. 6, Mar.-Apr. 2014, pp. 340-353.
Kelley, "Very Large Scale Monoclonal Antibody Purification: the Case for Conventional Unit Operations", Biotechnology Progress, vol. 23, No. 5, Sep.-Oct. 2007, pp. 995-1008.
Klein et al., "Progress in Overcoming the Chain Association Issue in Bispecific Heterodimeric IgG Antibodies", mAbs, vol. 4, No. 6, Nov. 1, 2012, pp. 653-663.
Klein et al., "The use of CrossMAb technology for the generation of bi- and multispecific antibodies", mAbs, Aug./Sep. 2016 (Aug./Sep. 2016), vol. 8( 6), Jun. 10, 2016, pp. 1010-1020.
Koerber et al., "An Improved Single-chain Fab Platform for Efficient Display and Recombinant Expression", J Mol Biol., vol. 427, No. 2, Jan. 30, 2015, pp. 567-586.
Kolfschonten et al., "Anti-Inflammatory Activity of Human IgG4 Antibodies by Dynamic Fab Arm Exchange", Science, vol. 317, No. 5844, Sep. 14, 2007, pp. 1554-1557.
Kontermann, "Dual Targeting Strategies with Bispecific Antibodies", mABs, vol. 4, Issue 2, Mar.-Apr. 2012, pp. 182-197.
Application No. KR10-2015-7017124, Notice of Decision to Grant, Mailed on Mar. 26, 2021, 4 pages.
Application No. KR10-2015-7017124, Office Action, Mailed on Mar. 9, 2020, 12 pages.
Application No. KR10-2015-7017124, Office Action, Mailed on Nov. 26, 2020, 7 pages.
Kreudenstein et al., "Improving Biophysical Properties of a Bispecific Antibody Scaffold to Aid Developability", Mabs, vol. 5, No. 5, Sep.-Oct. 2013, pp. 646-654.
Kreudenstein et al., "Protein Engineering and the Use of Molecular Modeling and Simulation: the Case of Heterodimeric Fc Engineering", Methods, vol. 65, No. 1, 2014, pp. 77-94.
Labrijin et al., "Efficient Generation of Stable Bispecific LgG1 by Controlled Fab-arm Exchange", PNAS., vol. 110, No. 13, Mar. 26, 2013, pp. 5145-5150.
Lehmann et al., "Stability Engineering of Anti-EGFR SCFV Antibodies by Rational Design of a Lambda-to-Kappa Swap of the VL Framework Using a Structure-Guided Approach", MAbs, vol. 7, No. 6, 2015, pp. 1058-1071.

Lewis et al., "Generation of Bispecific IgG Antibodies by Structure-Based Design of an Orthogonal Fab Interface", Nature Biotechnology, vol. 32, No. 2, Feb. 2014, pp. 191-198.
Lewis et al., "Targeting Her2-Positive Breast Cancer with Trastuzumab-DM1, an Antibody-Cytotoxic Drug Conjugate", Cancer Res., vol. 68, No. 22, Nov. 15, 2008, pp. 9280-9290.
Li et al., "Bispecific Antibody to Erbb2 Overcomes Trastuzumab Resistance Through Comprehensive Blockade of Erbb2 Heterodimerization", Cancer Research, vol. 73, Issue 21, Sep. 17, 2013, pp. 6471-6483.
Lindhofer et al., "Preferential Species-Restricted Heavy/light Chain Pairing in Rat/Mouse Quadromas", The Journal of Immunology, vol. 155, No. 1, Jul. 1, 1995, pp. 219-225.
Liu et al., "A Novel Antibody Engineering Strategy for Making Monovalent Bispecific Heterodimeric IgG Antibodies by Electrostatic Steering Mechanism", Journal of Biological Chemistry, vol. 290, No. 12, Mar. 20, 2015, pp. 7535-7562.
Lloyd et al., "Modelling the Human Immune Response: Performance of a 10 Human Antibody Repertoire Against a Broad Panel of Therapeutically Relevant Antigens", Protein Engineering, Design and Selection, vol. 22, No. 3, Mar. 2009, pp. 159-168.
Lorusso et al., "Trastuzumab Emtansine: a Unique Antibody-drug Conjugate in Development for Human Epidermal Growth Factor Receptor 2-positive Cancer", Clinical Cancer Research, vol. 17, Issue 20, Oct. 15, 2011, pp. 6437-6447.
Lu et al., "Fab-scFv Fusion Protein: an Efficient Approach to Production of Bispecific Antibody Fragments", Journal of Immunological Methods, vol. 267, No. 2, May 2, 2002, pp. 213-226.
Lund et al., "Human Fc Gamma RI and Fe Gamma RII Interact With Distinct but Overlapping Sites on Human IgG", J. Immunol., vol. 147, No. 8, Oct. 15, 1991, pp. 2657-2662.
Lund et al., "Multiple Binding Sites on the CH2 Domain of IgG for Mouse Fc Gamma R11", Mol. Immunol., vol. 29, No. 1, Jan. 1992, pp. 53-59.
Lund et al., "Multiple Interactions of IgG with its Core Oligosaccharide can Modulate Recognition by Complement and Human Fcy Receptor I and Influence the Synthesis of its Oligosaccharide Chains", J. Immunol., vol. 157, No. 11, Dec. 1, 1996, pp. 4963-4969.
MacCallum et al., "Antibody-Antigen Interactions: Contact Analysis and Binding Site Topography", Journal of Molecular Biology, vol. 262, No. 5, Oct. 1996, pp. 732-745.
Marqusee et al., "Helix Stabilization by Glu -. . . Lys+ Salt Sridges in Short Peptides of De Novo Design", Proc. Natl. Acad. Sci. USA., vol. 84, No. 24, Dec. 1987, pp. 8898-8902.
McCann et al., "Peptide Tags for Labeling Membrane Proteins in Live Cells with Multiple Fluorophores", Bio Techniques, vol. 38, No. 6, Jun. 2005, pp. 945-951.
McDonagh et al., "Antitumor Activity of a Novel Bispecific Antibody that Targets the ErbB2/ErbB3 Oncogenic Unit and Inhibits Heregulin-Induced Activation of ErbB3", Molecular Cancer Therapeutics, vol. 11, No. 3, Mar. 2012, pp. 582-593.
Merchant et al., "An Efficient Route to Human Bispecific IgG", Nature Biotechnology, vol. 16, No. 7, Jul. 1998, pp. 677-681.
Merk et al., "Cell-Free Expression of Two single-Chain Monoclonal Antibodies against Lysozyme: Effect of Domain Arrangement on the Expression", J. Biochem., vol. 125, Dec. 31, 1999, pp. 328-333.
Miller et al., "Stability Engineering of scFvs for the Development of Bispecific and Multivalent Antibodies", Protein Engineering, Design and Selection, vol. 23, Issue 7, 2010, pp. 549-557.
Milstein et al., "Hybrid Hybridomas and their Use in Immunohistochemistry", Nature, vol. 305, No. 6, Oct. 6, 1983, pp. 537-540.
Moore et al., "A Novel Bispecific Antibody Format Enables Simultaneous Bivalent and Monovalent Co-Engagement of Distinct Target Antigens", mAbs, vol. 3, No. 6, Nov.-Dec. 2011, pp. 546-557.
Moore et al., "Engineered Fc Variant Antibodies With Enhanced Ability to Recruit Complement and Mediate Effector Functions", MABS, Landes Biosciences, vol. 2, No. 2, Mar. 1, 2010, pp. 181-189.
Application No. MX/A/2013/004997, Office Action, Mailed on Oct. 13, 2016, 3 pages.

(56) References Cited

OTHER PUBLICATIONS

Application No. MX/A/2015/006758, Office Action, Mailed on Dec. 4, 2019, 10 pages.
Application No. MX/A/2015/006758, Office Action, Mailed on Jul. 21, 2020, 17 pages.
Application No. MX/A/2015/006758, Office Action, Mailed on Jul. 22, 2015, 2 pages.
Application No. MX/A/2016/015459, Office Action, Mailed on Aug. 5, 2020, 10 pages.
Application No. MX/A/2016/015459, Office Action, Mailed on Apr. 12, 2021, 7 pages.
Application No. MX/A/2018/004285, Office Action, Mailed on Jun. 20, 2018, 2 pages.
Application No. MX15/006758, Office Action, Mailed on Oct. 29, 2018, 10 pages.
Application No. MX15/006758, Office Action, Mailed on Apr. 11, 2019, 9 pages.
Omidfar et al., "Single Domain Antibodies: a New Concept for Epidermal Growth Factor Receptor and EGFRvIII Targeting", DNA and Cell Biology, vol. 31, No. 6, Jun. 2012, pp. 1015-1026.
Omidfar et al., "Studies of Thermostability in Camelus Bactrianus (Bactrian Camel) Single-Domain Antibody Specific for the Mutant Epidermal-Growth-Factor Receptor Expressed by Pichia", Biotechnol. Appl. Biochem., vol. 46, Jan. 2007, pp. 41-49.
Osborn et al., "Pharmacokinetic and Pharmacodynamics Studies of a Human Serum Albumin-Interferon-α Fusion Protein in Cynomolgus Monkeys", Journal of Pharmacology and Experimental Therapeutics, vol. 303, No. 2, Nov. 2002, pp. 540-548.
Padlan et al., "Antibody Fab Assembly: the Interface Residues Between CH1 and CL", Molecular Immunology, vol. 23, No. 9, Sep. 1986, pp. 951-960.
Paul, "Protein and Polypeptide Antigenic Determinants", Fundamental Immunology, 3d ed., 1993, p. 242.
Application No. PCT/CA2011/000321, International Search Report and Written Opinion, Mailed on Jul. 15, 2011, 15 pages.
Application No. PCT/CA2011/000322, International Search Report and Written Opinion, Mailed on Jun. 27, 2011, 15 pages.
Application No. PCT/CA2011/001238, International Search Report and Written Opinion, Mailed on Jan. 26, 2012, 16 pages.
Application No. PCT/CA2012/050131, International Search Report and Written Opinion, Mailed on May 23, 2012, 9 pages.
Application No. PCT/CA2012/050780, International Search Report and Written Opinion, Mailed on Feb. 14, 2013, 17 pages.
Application No. PCT/CA2013/000471, International Search Report and Written Opinion, Mailed on Aug. 15, 2013, 12 pages.
Application No. PCT/CA2013/050358, International Search Report and Written Opinion, Mailed on Jul. 30, 2013, 19 pages.
Application No. PCT/CA2013/050832, International Search Report and Written Opinion, Mailed on Jan. 23, 2014, 10 pages.
Application No. PCT/CA2013/050914, International Preliminary Report on Patentability, Mailed on Jun. 11, 2015, 8 pages.
Application No. PCT/CA2013/050914, International Search Report and Written Opinion, Mailed on Feb. 7, 2014, 11 pages.
Application No. PCT/CA2014/050486, International Search Report and Written Opinion, Mailed on Jan. 23, 2014, 15 pages.
Application No. PCT/CA2014/051140, International Search Report and Written Opinion, Mailed on Feb. 18, 2015, 17 pages.
Application No. PCT/CA2016/051183, International Preliminary Report on Patentability, Mailed on Apr. 19, 2018, 9 pages.
Application No. PCT/CA2016/051183, International Search Report and Written Opinion, Mailed on Dec. 21, 2016, 18 pages.
Application No. PCT/CA2018/050809, International Search Report and Written Opinion, Mailed on Sep. 17, 2018, 13 pages.
Application No. PCT/IB2015/054107, International Preliminary Report on Patentability, Mailed on Dec. 8, 2016, 12 pages.
Application No. PCT/IB2015/054107, International Search Report and Written Opinion, Mailed on Sep. 1, 2015, 19 pages.
Application No. PCT/US2013/047725, International Preliminary Report on Patentability, Mailed on Dec. 31, 2014, 7 pages.
Application No. PCT/US2013/047725, International Search Report and Written Opinion, Mailed on Nov. 22, 2013, 15 pages.
Application No. PCT/US2013/050408, International Search Report and Written Opinion, Mailed on Feb. 6, 2014, 14 pages.
PCT/US2013/050408, "Invitation to Pay Additional Fees", Nov. 21, 2013, 3 pages.
Application No. PCT/US2013/050411, International Search Report and Written Opinion, Mailed on Jan. 29, 2014, 19 pages.
Application No. PCT/US2013/051747, International Search Report and Written Opinion, Mailed on Feb. 3, 2014, 14 pages.
Application No. PCT/US2013/063306, International Search Report and Written Opinion, Mailed on Jan. 30, 2014, 41 pages.
PCT/US2013/50411, "Invitation to Pay Additional Fees", Nov. 13, 2013, 4 pages.
Application No. PCT/US2014/037401, International Search Report and Written Opinion, Mailed on Oct. 7, 2014, 10 pages.
Application No. PCT/US2014/065571, International Search Report and Written Opinion, Mailed on Feb. 19, 2015, 13 pages.
Application No. PCT/US2014/46436, International Search Report and Written Opinion, Mailed on Jan. 2, 2015, 15 pages.
PCT/US2014/46436, "Invitation to Pay Additional Fees", Oct. 30, 2014, 3 pages.
PCT/US2014/65546, "Invitation to Pay Additional Fees", Feb. 4, 2015, 2 pages.
PCT/US2015/033071, "Invitation to Pay Additional Fees and Partial Search Report", Aug. 28, 2015, 5 pages.
Pham et al., "Large-Scale Transfection of Mammalian Cells for the Fast Production of Recombinant Protein", Molecular Biotechnology, vol. 34, No. 2, Oct. 2006, pp. 225-237.
Pluckthun, "Antibodies From *Escherichia coli*", in: the Pharmacology of Monoclonal Antibodies, Rosenburg and Moore eds, Springer-Verlag, vol. 113, No. 11, 1994, pp. 269-315.
Portolano et al., "Lack of Promiscuity in Autoantigen-Specific H and L Chain Combinations as Revealed by Human H and L Chain "Roulette"", J Immunol., vol. 150, No. 3, Feb. 1, 1993, pp. 880-887.
Presta et al., "Engineering Therapeutic Antibodies for Improved Function", Biochem. Soc. Trans., vol. 30, No. 4, Aug. 2002, pp. 487-490.
Rakestraw et al., "Secretion-and-Capture Cell-Surface Display for Selection of Target-Binding Proteins", Protein Engineering, Design and Selection, vol. 24, No. 6, Mar. 14, 2011, pp. 525-530.
Raymond et al., "A Simplified Polyethylenimine-Mediated Transfection Process for Large-Scale and High-Throughput Applications", Methods, vol. 55, No. 1, Sep. 2011, pp. 44-51.
Reddy et al., "Elimination of Fc Receptor-Dependent Effector Functions of a Modified IgG4 Monoclonal Antibody to Human CD4", J. Immunol., vol. 164, No. 4, Feb. 15, 2000, pp. 1925-1933.
Ridgway et al., "Knobs-Into-Holes Engineering of Antibody CH3 Domains for Heavy Chain Heterodimerization", Protein Engineering, vol. 9, No. 7, Jul. 1996, pp. 617-621.
Robinson et al., "Targeting ErbB2 and ErbB3 with a Bispecific Single-Chain Fv Enhances Targeting Selectivity and Induces a Therapeutic Effect in Vitro", British Journal of Cancer, vol. 99, Nov. 4, 2008, pp. 1415-1425.
Rothlisberger et al., "Domain Interactions in the Fab Fragment: a Comparative Evaluation of the Single-chain Fv and Fab Format Engineered with Variable Domains of Different Stability", J. Mol. Biol., vol. 347, No. 4, Apr. 8, 2005, pp. 773-789.
Application No. RU2013124423, Notice of Allowance, Mailed on Jun. 15, 2016, 3 pages.
Application No. RU2013124423, Office Action, Mailed on Aug. 27, 2015, 4 pages.
Application No. RU2013124423, Office Action, Mailed on Jan. 22, 2016, 4 pages.
Application No. RU2014121832, Office Action, Mailed on Nov. 25, 2016, 6 pages.
Application No. RU2015125486, Notice of Decision to Grant, Mailed on Feb. 7, 2020, 36 pages.
Application No. RU2015125486, Office Action, Mailed on Jun. 18, 2018, 10 pages.
Application No. RU2015125486, Office Action, Mailed on Oct. 25, 2017, 9 pages.

(56) References Cited

OTHER PUBLICATIONS

Application No. RU2016145906, Notice of Decision to Grant, Mailed on May 26, 2020, 36 pages.
Application No. RU2016145906, Office Action, Mailed on Feb. 14, 2018, 14 pages.
Application No. RU2016145906, Office Action, Mailed on Oct. 11, 2019, 6 pages.
Application No. RU2016145906, Office Action, Mailed on Jul. 10, 2018, 9 pages.
Application No. RU2018116846, Office Action, Mailed on Mar. 27, 2020, 15 pages.
Rudikoff et al., "Single Amino Acid Substitution Altering Antigen-Binding Specificity", Proceedings of the National Academy of Sciences, Immunology, vol. 79, No. 6, Mar. 1982, pp. 1979-1983.
Schaefer et al., "Immunoglobulin Domain Crossover as a Generic Approach for the Production of Bispecific LgG Antibodies", PNAS, vol. 108, No. 27, Jul. 5, 2011, pp. 11187-11192.
Schlatter et al., "On the Optimal Ratio of Heavy to Light Chain Genes for Efficient Recombinant Antibody Production by CHO Cells", Biotechnology Progress, vol. 21, No. 1, Jan.-Feb. 2005, pp. 122-133.
Segal et al., "Introduction: Bispecific Antibodies", Journal of Immunological Methods, vol. 248, Nos. 1-2, Feb. 1, 2001, pp. 1-6.
Shields et al., "High Resolution Mapping of the Binding Site on Human IgG1 for FcγRI, FcγRII, FcγRIII, and FcRn and Design of IgG1 Variants with Improved Binding to the FcγR", Journal of Biological Chemistry, vol. 276, No. 9, Mar. 2, 2001, pp. 6591-6604.
Stancovski et al., "Mechanistic Aspects of the Opposing Effects of Monoclonal Antibodies to the ERBB2 Receptor on Tumor Growth", Proceedings of the National Academy of Sciences, vol. 88, No. 19, Oct. 1, 1991, pp. 8691-8695.
Stanglmaier et al., "Bi20 (FBTA05), a Novel Trifunctional Bispecific Antibody (Anti-CD20 X Anti-CD3), Mediates Efficient Killing of B-Cell Lymphoma Cells Even With Very Low CD20 Expression Levels", International Journal of Cancer, vol. 123, No. 5, Sep. 1, 2008, pp. 1181-1189.
Strohl et al., "Cell Line Development", Therapeutic Antibody Engineering, Cambridge Woodhead Publishing, 2012, pp. 420-437.
Strop et al., "Generating Bispecific Human IgG1 and IgG2 Antibodies from any Antibody Pair", Journal of Molecular Biology, vol. 420, No. 3, Jul. 13, 2012, pp. 204-219.
Suresh et al., "Bispecific Monoclonal Antibodies From Hybrid Hybridomas", Methods in Enzymology, vol. 121, 1986, pp. 210-228.
Talmadge et al., "Murine Models to Evaluate Novel and Conventional Therapeutic Strategies for Cancer", The American Journal of Pathology, vol. 170, No. 3, Mar. 2007, pp. 793-804.
Tamaskovic et al., "Designed Ankyrin Repeat Proteins (DARPins): From Research to Therapy", Methods in Enzymology, vol. 503, 2012, pp. 101-134.
Tao et al., Biochemistry, World Publishing Xi'an Co., Ltd., Aug. 31, 2010, p. 234.
Thurber et al., "Antibody Tumor Penetration: Transport Opposed by Systemic and Antigen-Mediated Clearance", Adv Drug Deliv Rev., vol. 60, No. 12, Apr. 24, 2008, 1421-1434.
Traunecker et al., "Bispecific Single Chain Molecules (Janusins) Target Cytotoxic Lymphocytes on HIV Infected Cells", EMBO Journal, vol. 10, No. 12, Dec. 1991, pp. 3655-3699.
Troise et al., "Differential Binding of Human Immunoagents and Herceptin to the ErbB2 Receptor", FEBS Journal, vol. 275, No. 20, Oct. 2008, pp. 4967-4979.
Tu et al., "Generation and Characterization of Chimeric Antibodies against NS3, NS4, NS5, and Core Antigens of Hepatitis C Virus", Clinical & Vaccine Immnology, vol. 17, No. 6, Jun. 2010, pp. 1040-1047.
Verheesen et al., "Selection by Phage Display of Single Domain Antibodies Specific to Antigens in Their Native Conformation", Methods in Molecular Biology, vol. 911, Jul. 12, 2012, pp. 81-104.
Vie et al., "Human Fusion Proteins Between Interleukin 2 and LgM Heavy Chain are Cytotoxic for Cells Expressing the Interleukin 2 Receptor", Proc. Natl. Acad. Sci., vol. 89, Dec. 1992, pp. 11337-11341.
Vitetta et al., "Considering Therapeutic Antibodies", Immunology, Science, vol. 313, No. 5785, Jul. 21, 2006, pp. 308-309.
Voskoglou-Nomikos et al., "Clinical Predictive Value of the In Vitro Cell Line, Human Xenograft, and Mouse Allograft Preclinical Cancer Models", Clinical Cancer Research, vol. 9, Sep. 15, 2003, pp. 4227-4239.
Wang, "Protein Aggregation and Its Inhibition in Biopharmaceutics", International Journal of Pharmaceutics, vol. 289, Nos. 1-2, Jan. 31, 2005, pp. 1-30.
Ward et al., "Binding Activities of a Repertoire of Single Immunoglobulin Variable Domains Secreted from *Escherichia coli*", Nature, vol. 341, No. 6242, Oct. 12, 1989, pp. 544-546.
Wesolowski et al., "Single Domain Antibodies: Promising Experimental and Therapeutic Tools in Infection and Immunity", Med. Microbiol. Immunol., vol. 198, No. 3, Aug. 2009, pp. 157-174.
Wiens et al., "Mutation of a Single Conserved Residue in VH Complementarity-Determining Region 2 Results in a Severe Ig Secretion Defect", The Journal of Immunology, vol. 167, No. 4, Aug. 2001, pp. 2179-2186.
Woods et al., "LC-MS Characterization and Purity Assessment of a Prototype Bispecific Antibody", mAbs, vol. 5, No. 5, Sep. 1, 2013, pp. 711-722.
Wu et al., "Arming Antibodies: Prospects and Challenges for Immunoconjugates", Nature Biotech., vol. 23, No. 9, Sep. 2005, pp. 1137-1146.
Wu et al., "Humanization of a Murine Monoclonal Antibody by Simultaneous Optimization of Framework and CDR Residues", Journal of Molecular Biology, vol. 294, Nov. 1999, pp. 151-162.
Xu et al., "In Vitro Characterization of Five Humanized OKT3 Effector Function Variant Antibodies", Cell. Immunol., vol. 200, No. 1, Feb. 25, 2000, pp. 16-26.
Yager, "Clinical Immunology and Allergology", 2nd edition, Translated from German., M.: Medicine, vol. 3, 1990, pp. 484-485.
Yarilin, "Basic Immunology", M.: Medicine, 1999, pp. 172-174.
Yarilin, "Fundamentals of Immunology", Textbooks for Medical Students, M.: Medicine, 1999, pp. 172-174.
Yu et al., "Interaction between Bevacizumab and Murine VEGF-A: a Reassessment", Investigative Ophthalmology & Visual Science, vol. 49, No. 2, Feb. 2008, pp. 522-527.
Zhu et al., "Remodeling Domain Interfaces to Enhance Heterodimer Formation", Protein Science, vol. 6, No. 4, Apr. 1997, pp. 781-788.
U.S. Appl. No. 15/314,496, "Corrected Notice of Allowability", Jan. 21, 2022, 9 pages.
U.S. Appl. No. 15/314,496, "Corrected Notice of Allowability", Jan. 27, 2022, 5 pages.
U.S. Appl. No. 15/314,496, "Notice of Allowance", Dec. 6, 2021, 11 pages.
Ru2020112916, "Office Action", Sep. 1, 2023, 27 pages.
Berry, et al., "Substitution of Cysteine for Selenocysteine in Type I Iodothyronine Deiodinase Reduces the Catalytic Efficiency of the Protein but Enhances Its Translation", Endocrinology, vol. 131, No. 4, Oct. 1992, pp. 1848-1852.
Chen, et al., "Fusion Protein Linkers: Property, Design and Functionality", Advanced Drug Delivery Reviews, vol. 65, No. 10, Oct. 15, 2013, pp. 1357-1369.
Halin, et al., "Synergistic Therapeutic Effects of a Tumor Targeting Antibody Fragment, Fused to Interleukin 12 and to Tumor Necrosis Factor Alpha", Cancer Research, vol. 63, No. 12, Jun. 15, 2003, pp. 3202-3210.
Lund, et al., "Oligosaccharide-Protein Interactions in IgG can Modulate Recognition by Fcγ Receptors", The FASEB Journal, vol. 9, No. 1, Jan. 1995, pp. 115-119.
Maeda, et al., "Engineering of Functional Chimeric Protein Gvargula Luciferase", Analytical biochemistry, vol. 249, No. 2, Jul. 1997, pp. 147-152.
Mariuzza, et al., "The Structural Basis of Antigen-Antibody Recognition", Annual Review of Biophysics and Biophysical Chemistry, vol. 16, Jun. 1987, pp. 139-159.

(56) References Cited

OTHER PUBLICATIONS

Pan, et al., "Blocking Neuropilin-1 Function Has an Additive Effect with Anti-VEGF to Inhibit Tumor Growth", Cancer Cell, vol. 11, No. 1, Jan. 2007, pp. 53-67.
Riechmann, et al., "Reshaping Human Antibodies for Therapy", Nature, vol. 332, No. 6162, Mar. 24, 1988, pp. 323-327.
Singer et al., Genes and genomes; Two Volumes, V. 1, Moscow, "Mir", 1998, p. 63.
Su, et al., "The Role of Antibody Vk Framework 3 Region Towards Antigen Binding: Effects on Recombinant Production and Protein L Binding", Scientific Reports, vol. 7, No. 1, Jun. 2017, pp. 1-7.
Vajdos, et al., "Comprehensive Functional Maps of the Antigen-Binding Site of an Anti-ErbB2 Antibody Obtained with Shotgun Scanning Mutagenesis", Journal of Molecular Biology, vol. 320, No. 2, Jul. 5, 2002, pp. 415-428.
Jp2022-186638, "Office Action", Oct. 25, 2023, 4 pages.

\* cited by examiner

Fig. 1

| Co-expression set | | Mutations from wild-type | | | Mutations from wild-type | | | Competition assay screen results | | | Competition assay verification results |
|---|---|---|---|---|---|---|---|---|---|---|---|
| | | Variable domain (VH:VL) | | | | | | | | | |
| Set # | Set # | H1 mutation | L1 mutation | H2 mutation | L2 mutation | | | H1_L1:H1_L2 | H2_L2:H2_L1 | | |
| V001 | V002 | V37W_W103H* | F98L | V37I | F98W | | | 57.22:30.0 | 65.71:21.67 | | |
| V001 | V003 | V37W_W103H | F98L | WT | F98W | | | 57.22:30.0 | 74.2:27.76 | 62.29:30.52 | 50.8:23.6 |
| V004 | V005 | V37W_W103H | F98L | V37A_W103H | P44W | | | 48.27:29.21 | 66.54:6.378 | 62.29:30.52 | |
| V006 | V002 | V37W_W103F | F98L | V37I | F98W | | | 64.17:14.8 | 65.71:21.67 | 56.02:21.18 | |
| V006 | V003 | V37W_W103F | F98L | WT | F98W | | | 64.17:14.8 | 74.2:27.76 | 38.2:27.7 | 50.8:23.6 |
| V007 | V008 | V37W | F98A | V37I | F98W | | | 62.4:23.5 | 66.51:30.86 | 38.2:27.7 | |
| V009 | V010 | V37W | F98A | V37I | WT | | | 64.1:28.8 | 72.56:28.69 | 61.5:23.4 | |
| V011 | V012 | V37I | WT | F100W | F98L | | | 78.51:7.343 | 56.83:29.68 | | 38.9:44.9 |
| V013 | V014 | V37A_W103V | P44W | V37W | F98A | | | 58.9:25.3 | 83.08:9.413 | | |
| V015 | V014 | V37A_W103H | P44W | V37W | F98A | | | 67.47:8.787 | 83.08:9.413 | 47.07:12.28 | |
| V016 | V017 | V37A_W103H | P44W | V37A_W103V | F98W | | | 53.6:19.59 | 52.96:18.56 | | 23.3:44.7 |
| V018 | V005 | V37A_W103H | P44W | V37A_W103V | F98L | | | 66.54:6.378 | 54.8:22.76 | | 52.0:23.0 |
| V019 | V005 | V37A_W103H | P44W | V37I_F100W | F98L | | | 66.54:6.378 | 67.33:26.86 | | 30.5:47.9 |
| V020 | V021 | L45W | Y87G | V37A_W103H | P44W | | | 54.53:23.86 | 53.1:18.9 | 58.1:31.0 | 61.5:23.4 |
| V022 | V007 | WT | F98W | V37W | F98A | | | 67.1:28.7 | 62.4:23.5 | 67.1:28.7 | |
| V023 | V009 | WT | WT | V37W | F98A | | | 84.5:7.5 | 64.1:28.8 | | |
| V024 | V025 | Q39R | Q38E | V37W | F98A | | | 82.55:4.303 | 65.9:8.054 | 76.6:4.0 | 70.5:10.3 |
| V026 | V027 | Q39R | Q38E | WT | WT | | | 66.36:19.12 | 58.83:32.93 | 68.7:21.8 | 57.9:36.9 |
| V028 | V029 | Q39R | Q38E | Q39E | Q38R | | | 71.07:22.74 | 65.35:29.89 | 85.1:8.4 | 62.7:30.2 |
| V030 | V031 | Q39R | Q38D | Q39E | Q38R | | | 73.3:10.75 | 60.01:18.02 | | |
| V032 | V033 | Q39M | Q38M | Q39R | Q38E | | | 69.64:33.29 | 68.33:23.52 | 60.2:31.3, 58.8:40.6 | 82.9:17.3, 70.6:27.4 |
| V034 | V035 | Q39K | Q38N_T85E | Q39D | Q38N_T85K | | | 54.77:30.08 | 71.7:27.38 | | |
| V034 | V036 | Q39K | Q38N_T85E | Q39E | Q38N_T85K | | | 54.77:30.08 | 71.93:30.37 | 66.45:21.72 | 59.09:33.49 |
| V037 | V038 | Q39E | Q38R | V37W | F98A | | | 47.62:29.67 | 48.92:26.84 | 75.1:7.2 | 47.8:26.7 |
| V039 | V030 | Q39D | Q38R | Q39R | Q38D | | | 66.92:34.51 | 73.3:10.75 | 61.8:31.1 | 85.2:11.1 |
| V040 | V041 | V37E | L89R_F98T | WT | WT | | | 54.1:25.0 | 78.0:2.2 | 90.9:16.5 | 89.8:4.6 |
| V042 | V043 | V37E_F100D | L89R_F98W | WT | WT | | | 98.7:4.2 | 85.2:6.2 | 118.6:4.5 | 83.1:14.1 |
| V044 | V045 | V37E_F100D | L89R_F98W | V37S_A97K | F98Y | | | 67.8:24.4 | 71.6:0.5 | 76.3:18.1 | 65.6:11.7 |

*Kabat numbering. #WT: Wild-type D3H44 HC (with C-terminus ABD2-His6 tag) or wild-type D3H44 LC (with a N-terminus HA or FLAG tag).

Fig. 2

| Co-expression set | | Mutations from wild-type | | | | | Competition assay screen results | | Competition assay verification results |
|---|---|---|---|---|---|---|---|---|---|
| | | Constant domain (CH1:CL) | | | | | | | |
| Set # | Set # | H1_mutation* | L1_mutation | H2_mutation | L2_mutation | | H1_L1:H1_L2 | H2_L1:H2_L1 | |
| C500 | C501 | WT | WT | A139W_V190S | F116A | | 67.8:26.3 | 66.92:21.06 | 43.0:22.3 |
| C500 | C502 | WT | WT | A139W_V190S | F116A | | 67.8:26.3 | 74.52:17.84 | 51.4:19.7 |
| C503 | C504 | WT | WT | F100W | F98L | | 71.22:13.34 | 56.83:29.68 | 38.9:44.9 |
| C505 | C506 | A139W_V190S | F116S | A139W | F118W_V133S | | 84.85:15.74 | 76.51:4.6 | 55.4:20.2 | 38.1:40.9 |
| C507 | C508 | A139W_V190S | F116A | A139V | F118W_V133S | | 68.74:33.42 | 63.92:35.74 | 83.78:0.722 | 24.5:56.1 |
| C501 | C502 | A139W | WT | A139W_V190S | F116A | | 58.7:30.5 | 66.92:21.06 | 43.0:22.3 |
| C509 | C509 | A139W | WT | A139W_V190A | F116A | | 58.7:30.5 | 74.52:17.84 | 51.4:19.7 |
| C510 | C508 | A139V_V190S | F116A | A139V | F118W_V133S | | 68.66:35.07 | 63.92:35.74 | 42.12:10.05 | 24.5:56.1 |
| C511 | C512 | A139V_V190S | WT | A139I | F118W_V133S | | 58.8:35.25 | 51.87:28.86 | 52.18:8.664 |
| C513 | C508 | A139I_V190S | F116A | A139V | F118W_V133S | | 64.68:25.15 | 63.92:35.74 | 59.82:0.7587 | 24.5:56.1 |
| C514 | C512 | A139I_V190S | WT | A139I | F118W_V133S | | 67.09:28.03 | 51.87:28.86 | 77.0:8.2 |
| C515 | C516 | A139G_V190A | L135W_N137A | A139W | F116A_L135A | | 70.46:5.156 | 73.59:19.83 | |
| C517 | C518 | A139G_V190A | L135W | A139W | F116A_L135A | | 65.02:10.13 | 77.41:17.4 | 69.49:10.64 | 78.7:10.16 |
| C519 | C520 | A139G_V190A | L135W | A139W | F116A_L135V | | 68.43:13.76 | 62.66:34.63 | 49.05:48.32 | 76.67:19.07 |
| C521 | C522 | S188I | WT | WT | S176V_T178L | | 61.87:41.89 | 99.36:0.0 | |
| C523 | C508 | V190G | F116A | A139V | F118W_V133S | | 55.06:35.32 | 63.92:35.74 | 56.1:24.5 |
| C524 | C506 | V190G | F116S | A139W | F118W_V133S | | 78.25:24.05 | 76.51:4.6 | 25.9:50.8 | 40.9:38.1 |
| C525 | C526 | S188L_V190Y | V133S | F174V_P175S_S188G | S176L | | 90.03:7.72 | 81.12:1.44 | 81.2:12.4 | 68.1:2.9 |
| C527 | C528 | F174V_P175S_S188G | S176L | F174V_S188L | WT | | 53.39:9.68 | 102.9:5.94 | |
| C527 | C529 | F174V_P175S_S188G | S176L | S188L | WT | | 53.39:9.68 | 92.45:9.32 | |
| C530 | C531 | D146G_Q179R | Q124E_Q160E_T178D | K145T_Q179D_S188L | Q160K_T178R | | 86.7:1.4 | 71.0:7.2 | 97.0:0.9 | 74.3:20.0 |
| C532 | C533 | L143A_D146G_Q179R | Q124E_V133W_Q160E_T180E | K145T_Q179D_S188F | V133A_Q160K_T178R | | 97.4:0.4 | 87.3:1.5 | 93.6:0.6 | 83.2:11.5 |

*Kabat numbering. #WT: Wild-type D3H44 HC (with C-terminus ABD2-His6 tag) or wild-type D3H44 LC (with a N-terminus HA or FLAG tag).

Fig. 3

| Heterodimer | Mutations from wild-type | | | Corresponding Co-expression Set # | | Tm (°C) | Antigen affinity (M)^ |
|---|---|---|---|---|---|---|---|
| | H1_mutation | L1_mutation | | Paired | Mispaired | | |
| WT# (940) | - | - | | - | - | 76.0 | $3.30 \times 10^{-11}$ |
| HD100 | Q39E | Q38R | | V029, V031, V037 | | 72.9 | $1.26 \times 10^{-10}$ |
| HD101 | Q39E | Q38E | | | V029 | 67.4 | $2.32 \times 10^{-11}$ |
| HD102 | Q39R | Q38E | | V028, V033, V026, V024 | | 72.8 | $5.53 \times 10^{-11}$ |
| HD103 | Q39R | Q38R | | | V028, V030 | 66.5 | $6.53 \times 10^{-11}$ |
| HD104 | V37A_W103H | P44W | | V015, V005, V016 | | 56.2 | $7.70 \times 10^{-10}$ |
| HD105 | V37W | F98A | | V009, V007, V014, V038, V025 | | 76.9 | $9.77 \times 10^{-10}$ |
| HD106 | V37W | P44W | | | V014 | 64.5 | $8.31 \times 10^{-09}$ |
| HD107 | A139G_V190A | L135W_N137A | | C515 | | 70.7 | $3.91 \times 10^{-11}$ |
| HD108 | A139G_V190A | F116A_L135A | | | C517, C515 | 60.1 | $6.45 \times 10^{-11}$ |
| HD109 | A139W | F116A_L135A | | C516, C518 | | 72.5 | $5.06 \times 10^{-11}$ |
| HD110 | S188H | S176G_T178V | | | | 74.3 | $4.03 \times 10^{-11}$ |
| HD111 | S188H | S176L_T178S | | | | 75.2 | $7.68 \times 10^{-11}$ |
| HD112 | V37W_W103H | F98L | | V001, V004 | | 60.9 | $5.17 \times 10^{-09}$ |
| HD113 | V37W_W103H | F98W | | | V001 | 61.5 | $3.24 \times 10^{-09}$ |
| HD114 | V37I | F98W | | V002, V008 | | 75.8 | $3.93 \times 10^{-11}$ |
| HD115 | V37I | F98L | | | V002, V011 | 70.0 | $2.42 \times 10^{-10}$ |

WT: Wild-type tagged D3H44 Fab. HC tag is a C-terminus ABD2-His$_6$ tag. LC tag is a N-terminus HA or FLAG tag.
^Antigen used: Tissue Factor extracellular domains

ENGINEERED IMMUNOGLOBULIN HEAVY CHAIN-LIGHT CHAIN PAIRS AND USES THEREOF

CROSS REFERENCE TO RELATED APPLICATIONS

This application is a divisional of U.S. patent application Ser. No. 15/896,170, filed Feb. 14, 2018, now U.S. Pat. No. 11,078,296, which is a divisional of U.S. patent application Ser. No. 14/092,804, filed Nov. 27, 2013, now U.S. Pat. No. 9,914,785, which claims the benefit of U.S. Provisional Application No. 61/730,906, filed Nov. 28, 2012, and U.S. Provisional Application No. 61/761,641, filed Feb. 6, 2013, the entire disclosure of each of which is hereby incorporated by reference in its entirety for all purposes.

INTRODUCTION

1. Field of the Invention

The present invention relates to the field of therapeutic antibodies, in particular to the field of therapeutic bi-specific antibodies.

2. Background of the Invention

Bi-specific antibodies are capable of binding to two different epitopes. The epitopes can be on the same antigen, or each epitope can be on a different antigen. This feature of bi-specific antibodies makes them an attractive tool for various therapeutic applications where there is a therapeutic benefit to targeting or recruiting more than one molecule in the treatment of disease. A bi-specific antibody is formed by concomitant expression of two unique antibody heavy chains and two unique antibody light chains. Correctly forming bi-specific antibodies in a format that is similar to wild-type remains a challenge, since antibody heavy chains have evolved to bind antibody light chains in a relatively promiscuous manner. As a result of this promiscuous pairing, concomitant expression of two antibody heavy chains and two antibody light chains naturally leads to a scrambling of heavy chain—light chain pairings. This mispairing remains a major challenge for the generation of bi-specific therapeutics, where homogeneous pairing is an essential requirement for good manufacturability and biological efficacy.

Several approaches have been described to prepare bi-specific antibodies in which specific antibody light chains or fragment pair with specific antibody heavy chains or fragments. A review of various approaches to address this problem can be found in Klein et al., (2012) mAbs 4:6, 653-63. International Patent Application No. PCT/EP2011/056388 (WO 2011/131746) describes an in vitro method for generating a heterodimeric protein in which asymmetrical mutations are introduced into the CH3 regions of two monospecific starting proteins in order to drive directional "Fab-arm" or "half-molecule" exchange between two monospecific IgG4- or IgG4-like antibodies upon incubation under reducing conditions.

Schaefer et al. (Roche Diagnostics GmbH), describe a method to assemble two heavy and two light chains, derived from two existing antibodies, into human bivalent bi-specific IgG antibodies without use of artificial linkers (PNAS (2011) 108(27): 11187-11192). The method involves exchanging heavy chain and light chain domains within the antigen-binding fragment (Fab) of one half of the bi-specific antibody.

Strop et al. (Rinat-Pfizer Inc.), describe a method of producing stable bi-specific antibodies by expressing and purifying two antibodies of interest separately, and then mixing them together under specified redox conditions (J. Mol. Biol. (2012) 420:204-19).

Zhu et al. (Genentech) have engineered mutations in the $V_L/V_H$ interface of a diabody construct consisting of variant domain antibody fragments completely devoid of constant domains, and generated a heterodimeric diabody (Protein Science (1997) 6:781-788). Similarly, Igawa et al. (Chugai) have also engineered mutations in the $V_L/V_H$ interface of a single-chain diabody to promote selective expression and inhibit conformational isomerization of the diabody (Protein Engineering, Design & Selection (2010) 23:667-677).

US Patent Publication No. 2009/0182127 (Novo Nordisk, Inc.) describes the generation of bi-specific antibodies by modifying amino acid residues at the Fc interface and at the $C_{H1}$:$C_L$ interface of light-heavy chain pairs that reduce the ability of the light chain of one pair to interact with the heavy chain of the other pair.

SUMMARY OF THE INVENTION

An object of the present invention is to provide engineered immunoglobulin heavy chain-light chain pairs and uses thereof. In one aspect of the invention is provided an antibody construct comprising at least a first heterodimer and a second heterodimer, said first heterodimer comprising a first immunoglobulin heavy chain polypeptide (H1), and a first immunoglobulin light chain polypeptide (L1); and said second heterodimer comprising a second immunoglobulin heavy chain polypeptide (H2), and a second immunoglobulin light chain polypeptide (L2), wherein H1 and H2 each comprise at least a heavy chain variable domain (VH domain), fragment or derivative thereof; and a heavy chain constant domain (CH1 domain), fragment or derivative thereof; and wherein L1 and L2 each comprise at least a light chain variable domain (VL domain), fragment or derivative thereof; and a light chain constant domain (CL domain), fragment or derivative thereof; and at least one of H1, H2, L1 and L2 comprises at least one amino acid modification of at least one constant domain and at least one variable domain such that H1 pairs preferentially with L1 as compared to L2, and/or H2 pairs preferentially with L2 as compared to L1, when H1, H2, L1 and L2 are co-expressed in a cell.

Provided herein is an antibody construct comprising at least a first heterodimer and a second heterodimer, said first heterodimer comprising a first immunoglobulin heavy chain polypeptide (H1), and a first immunoglobulin light chain polypeptide (L1); and said second heterodimer comprising a second immunoglobulin heavy chain polypeptide (H2), and a second immunoglobulin light chain polypeptide (L2); wherein H1 and H2 each comprise at least a VH domain, fragment or derivative thereof; and a $C_{H1}$ domain, fragment or derivative thereof; and L1 and L2 each comprise at least a VL domain, fragment or derivative thereof; and a CL domain, fragment or derivative thereof; and wherein at least one of H1, H2, L1 and L2 comprises at least one amino acid modification of a VH or VL domain and/or at least one amino acid modification of a CH or CL domain such that H1 pairs preferentially with L1 as compared to L2, and/or H2 pairs preferentially with L2 as compared to L1.

In an aspect is provided an antibody construct comprising at least a first heterodimer and a second heterodimer, said first heterodimer comprising a first immunoglobulin heavy chain polypeptide (H1), and a first immunoglobulin light chain polypeptide (L1); and said second heterodimer comprising a second immunoglobulin heavy chain polypeptide (H2), and a second immunoglobulin light chain polypeptide (L2); wherein H1 and H2 each comprise at least a VH domain, fragment or derivative thereof; and a CH1 domain, fragment or derivative thereof, and at least one of H1 and H2 comprises a variant VH domain or variant CH1 domain; and wherein L1 and L2 each comprise at least a VL domain, fragment or derivative thereof, and a CL domain, fragment or derivative thereof, and at least one of L1 and L2 comprises a variant VL domain or variant CL domain; and wherein the variant domain(s) comprise at least one amino acid modification such that H1 pairs preferentially with L1 as compared to L2, and H2 pairs preferentially with L2 as compared to L1, when H1, H2, L1 and L2 are co-expressed in a cell.

In certain embodiments is an antibody construct described herein, wherein H1 further interacts preferentially with H2 as compared to forming a homodimer. In an embodiment is an antibody construct described herein, wherein when both L1 and L2 are co-expressed with at least one of H1 and H2, the relative yield of the at least one of H1-L1 and H2-L2 heterodimer pair to that of the corresponding mispaired H1-L2 or H2-L1 heterodimer pair is greater than 50%. In some embodiments is an antibody construct described herein, wherein the relative yield of desired H1-L1 or H2-L2 heterodimer pair to that of mispaired H1-L2 or H2-L1 heterodimer pair is greater than 60%. In an embodiment is an antibody construct described herein, wherein the relative yield of desired H1-L1 or H2-L2 heterodimer pair to that of mispaired H1-L2 or H2-L1 heterodimer pair is greater than 70%. In select embodiments is an antibody construct described herein, wherein the relative yield of desired H1-L1 or H2-L2 heterodimer pair to that of mispaired H1-L2 or H2-L1 heterodimer pair is greater than 80%. In another embodiment is an antibody construct described herein, wherein the relative yield of desired H1-L1 or H2-L2 heterodimer pair to that of mispaired H1-L2 or H2-L1 heterodimer pair is greater than 90%.

In certain embodiments is an antibody construct described herein, wherein the thermal stability as measured by the melting temperature (Tm) of at least one of said first and second heterodimers is within about 5° C. of the Tm of the corresponding heterodimer without the amino acid modifications. In certain embodiments is an antibody construct described herein, wherein the thermal stability as measured by the melting temperature (Tm) of each heterodimer comprising at least one amino acid modification is within about 5° C. of the Tm of the corresponding heterodimer without the amino acid modifications.

In certain embodiments is an antibody construct described herein, wherein the affinity of each heterodimer for its antigen is within about 50-fold of the affinity of the wild type heterodimer for the antigen.

In certain embodiments is an antibody construct described herein, wherein at least one of L1 and L2 comprises a variant VL domain comprising an amino acid modification of at least one of F98, P44, Q38 and T85. In an embodiment is an antibody construct described herein, wherein at least one of H1 and H2 comprises a variant VH domain comprising an amino acid modification of at least one of V37, Q39, W103 and F100. In some embodiments is an antibody construct described herein, wherein at least one of H1 and H2 comprises a variant CH1 domain comprising an amino acid modification of at least one of A139, L143, K145, D146, F174, P175, Q179, S188 and V190. In certain embodiments is an antibody construct described herein, wherein at least one of L1 and L2 comprises a variant CL domain comprising an amino acid modification of at least one of F116, F118, Q124, V133, L135, Q160, S176, T178 and T180.

In certain embodiments is an antibody construct described herein, wherein at least one of H1, and L1 comprises at least one variant domain comprising at least one amino acid modification resulting in favorable steric complementarity of amino acids when H1 pairs with L1 as compared to L2. In some embodiments is an antibody construct described herein, wherein at least one of H2 and L2 comprises at least one variant domain comprising at least one amino acid modification resulting in favorable steric complementarity of amino acids when H2 pairs with L2 as compared to L1. In select embodiments is an antibody construct described herein, wherein at least one of H1, and L1 comprises at least one variant domain comprising at least one amino acid modification resulting in favorable electrostatic complementarity between charged amino acids when H1 pairs with L1 as compared to L2. In an embodiment is an antibody construct described herein, wherein at least one of H2, and L2 comprises at least one variant domain comprising at least one amino acid modification resulting in favorable electrostatic complementarity between charged amino acids when H2 pairs with L2 as compared to L1.

In certain embodiments is an antibody construct described herein, which is multispecific. In some embodiments is an antibody construct described herein, which is bispecific.

In certain embodiments is an antibody construct described herein, wherein said construct is multivalent. In some embodiments is an antibody construct described herein, wherein said construct is bivalent.

Provided herein is a nucleic acid construct encoding any of the antibody constructs described above.

Also provided is an expression vector containing a nucleic acid construct described herein, and capable of expressing said nucleic acid construct in a host cell.

In certain embodiments is provided a prokaryotic or eukaryotic host cell comprising an expression vector described herein.

Provided herein is a method for the preparation of an antibody construct described above comprising the steps of: transforming a host cell with vectors comprising nucleic acid molecules encoding antibody construct; culturing the host cell under conditions that allow synthesis of said heteromultimer construct; and recovering said antibody construct from said culture.

Provided herein is a composition comprising a set of polypeptides comprising a first immunoglobulin light chain polypeptide (L1), a second immunoglobulin light chain polypeptide (L2), and a immunoglobulin heavy chain polypeptide (H1) or fragment thereof comprising a VH domain and a CH1 domain, wherein if H1 comprises at least one amino acid modification in the CH1 domain, then at least one of L1 and L2 comprise at least one amino acid modification in the CL domain; and if H1 comprises at least one amino acid modification in the VH domain, then at least one of L1 and L2 comprise at least one amino acid modification in the VL domain; and wherein H1 preferentially pairs with either L1 or L2 when co-expressed in a mammalian cell.

Provided herein is a pharmaceutical composition comprising an antibody construct described above. Also provided is use of the pharmaceutical composition for the treatment of cancer. In certain embodiments is provided the use of an antibody construct described herein, for the manufacture of a medicament for the treatment of cancer. In certain embodiments is a method of treatment of patient suffering from cancer by administering an antibody construct described herein to a patient in the need of such treatment.

Provided herein is a pharmaceutical composition comprising an antibody construct described above. Also provided is the use of the pharmaceutical composition described herein for the treatment of vascular diseases. In certain embodiments is the use of an antibody construct described herein, for the manufacture of a medicament for the treatment of vascular diseases. In certain embodiments is a method of treatment of patient suffering from vascular diseases by administering an antibody construct described herein to a patient in the need of such treatment.

BRIEF DESCRIPTION OF THE FIGURES

FIG. 1 provides a Table showing the preferential pairing of heterodimers, from antibody constructs described herein, in co-expression sets where amino acid modifications have been made to the $V_H$ or $V_L$ domains.

FIG. 2 provides a Table showing the preferential pairing of heterodimers in co-expression sets where amino acid modifications have been made to the $C_{H1}$ or $C_L$ domains.

FIG. 3 provides a Table showing the thermal stability and affinity for antigen for selected preferentially paired or mispaired heterodimers from antibody constructs described herein.

DETAILED DESCRIPTION

Figure 4:
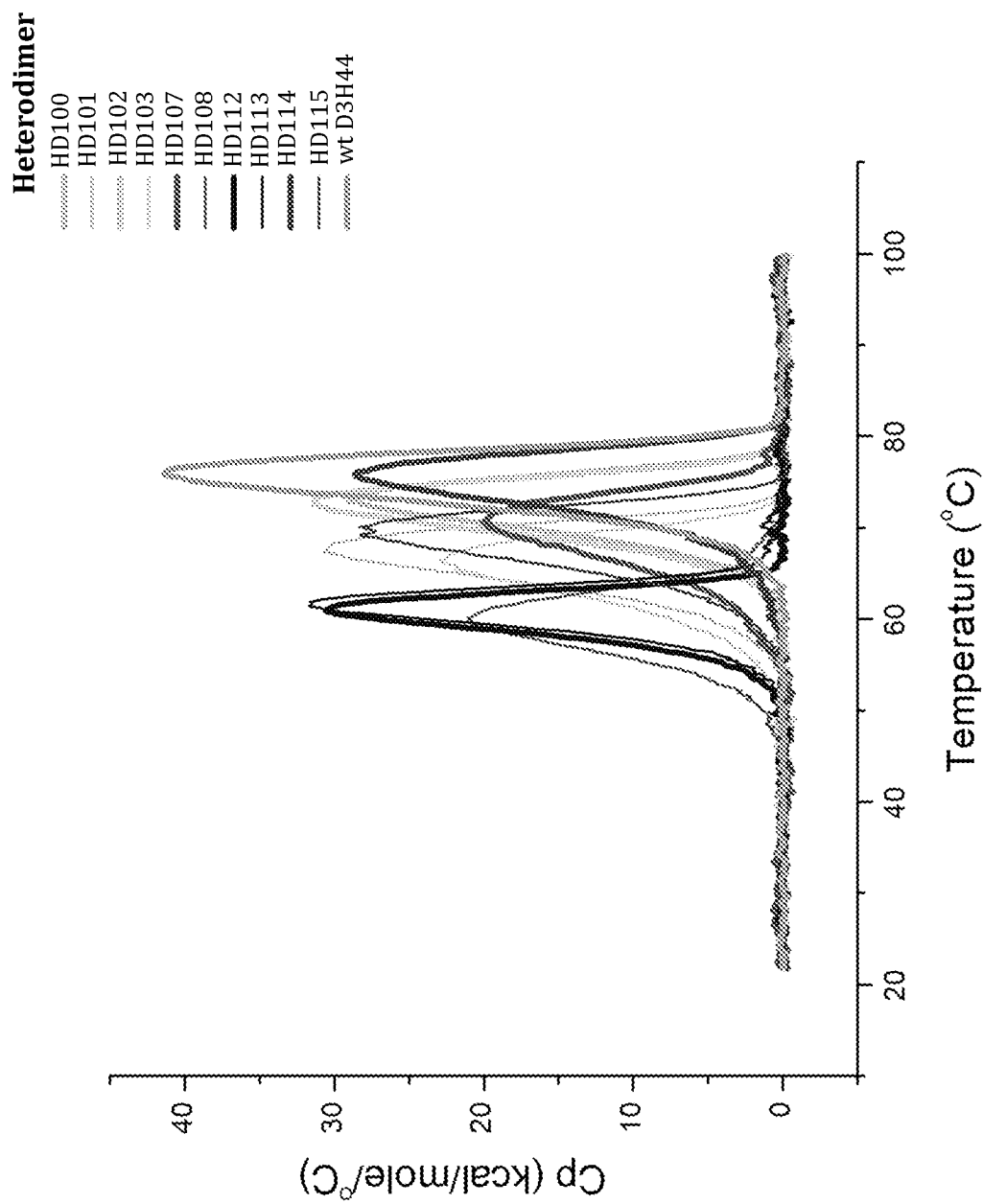
FIG. 4 provides thermal unfolding curves for selected heterodimers.
Figure 5A:
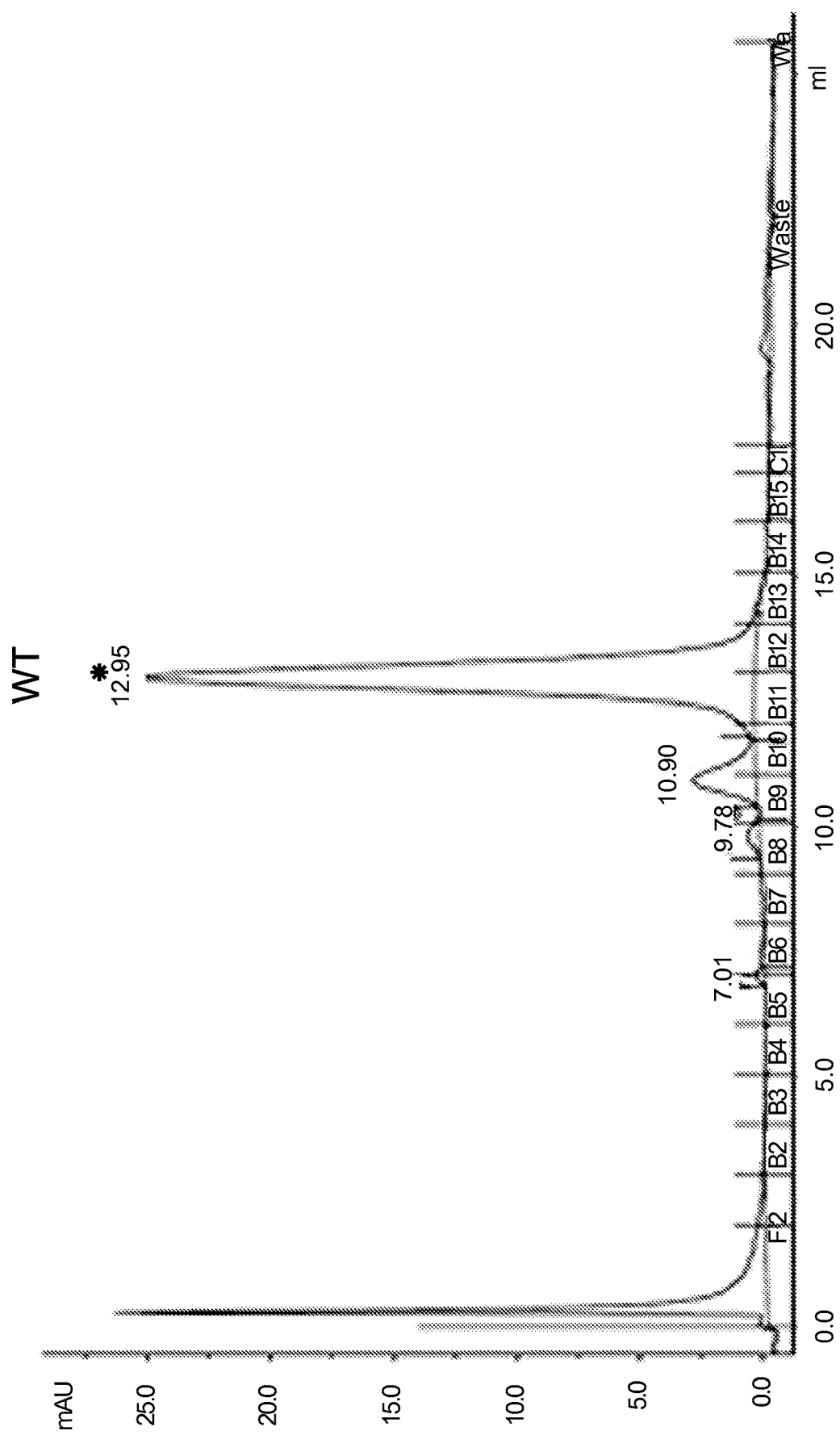
FIGS. 5A-D provides size exclusion chromatography profiles for selected heterodimers.
Figure 5B:
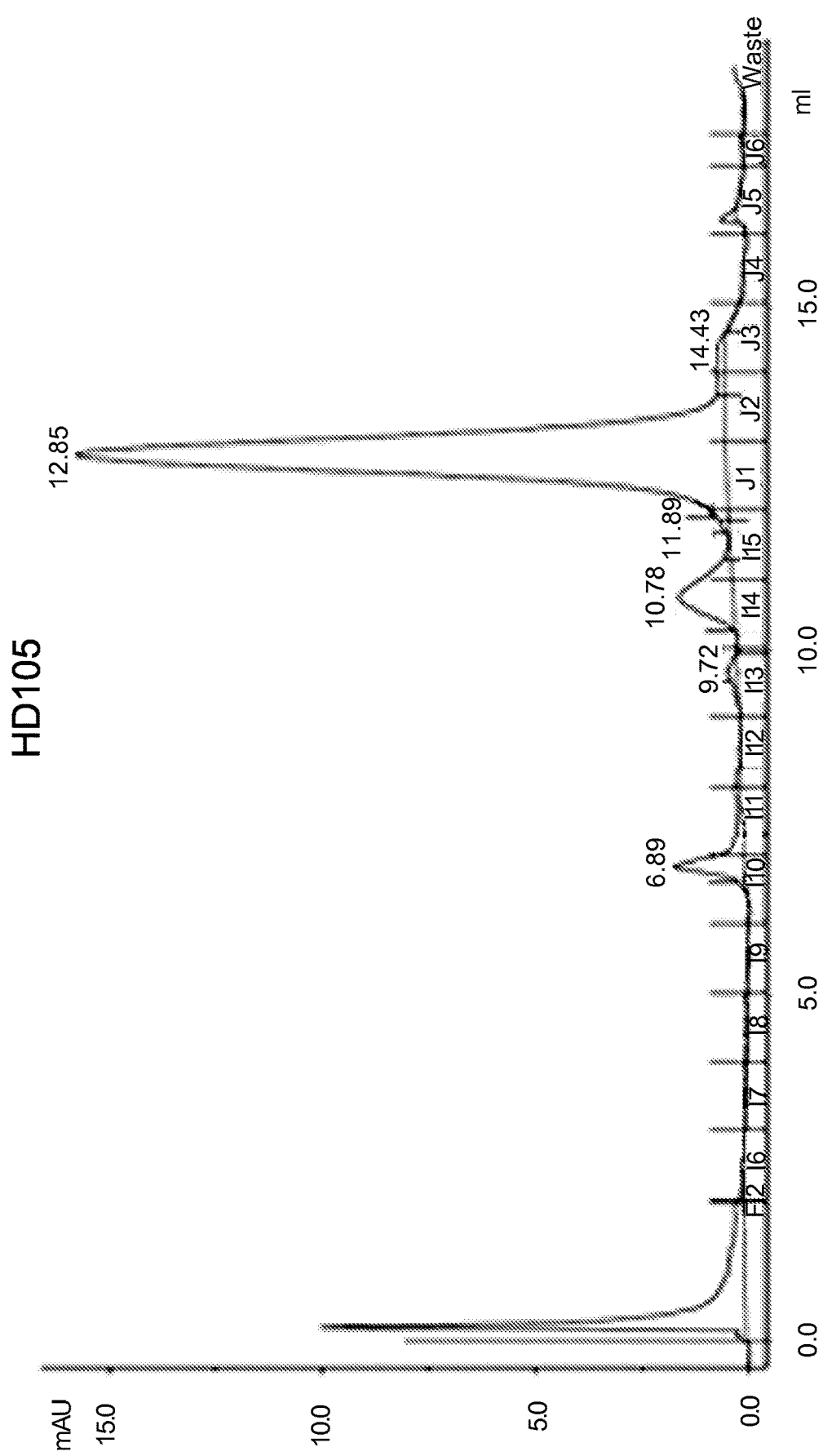
Figure 5C:
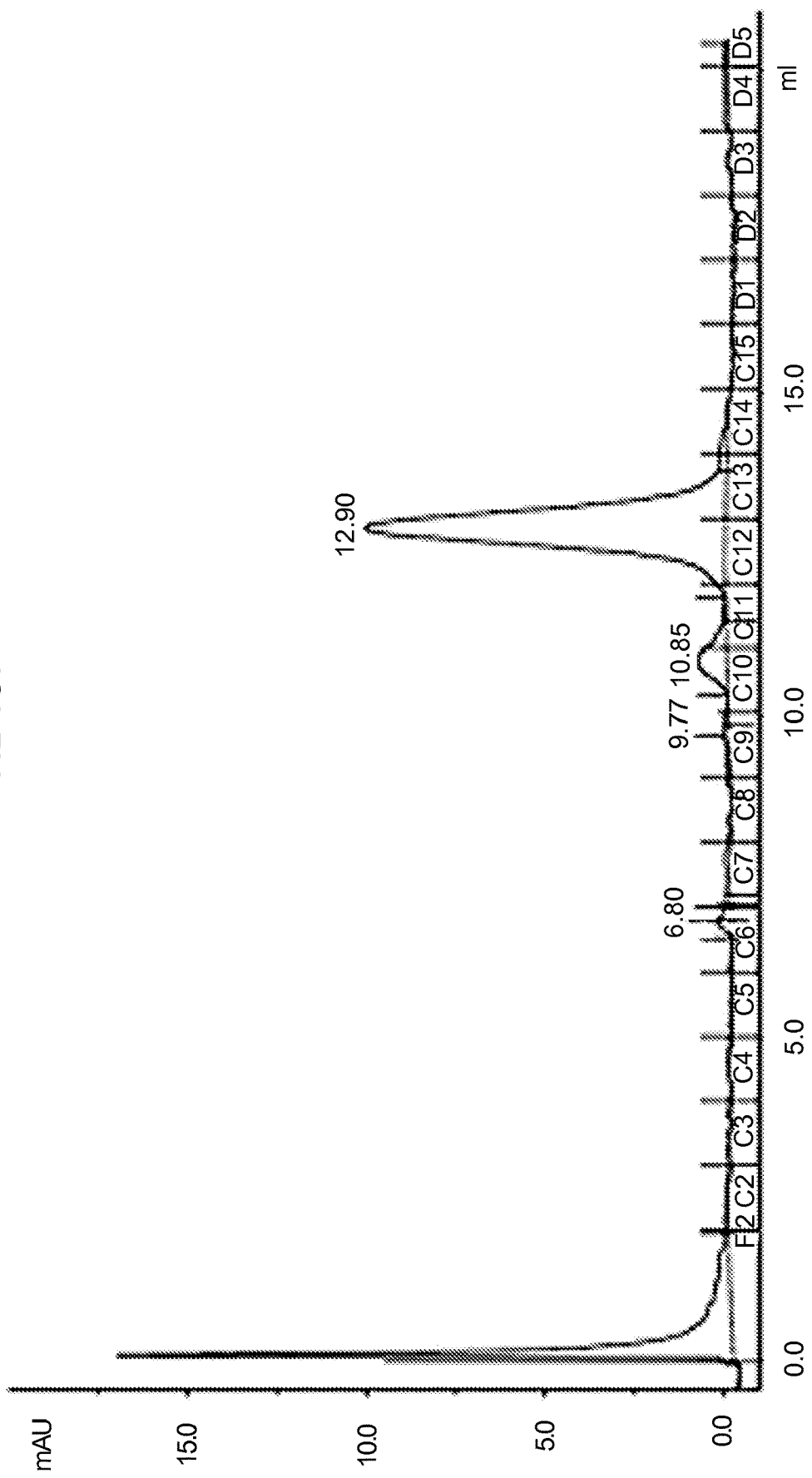
Figure 5D:
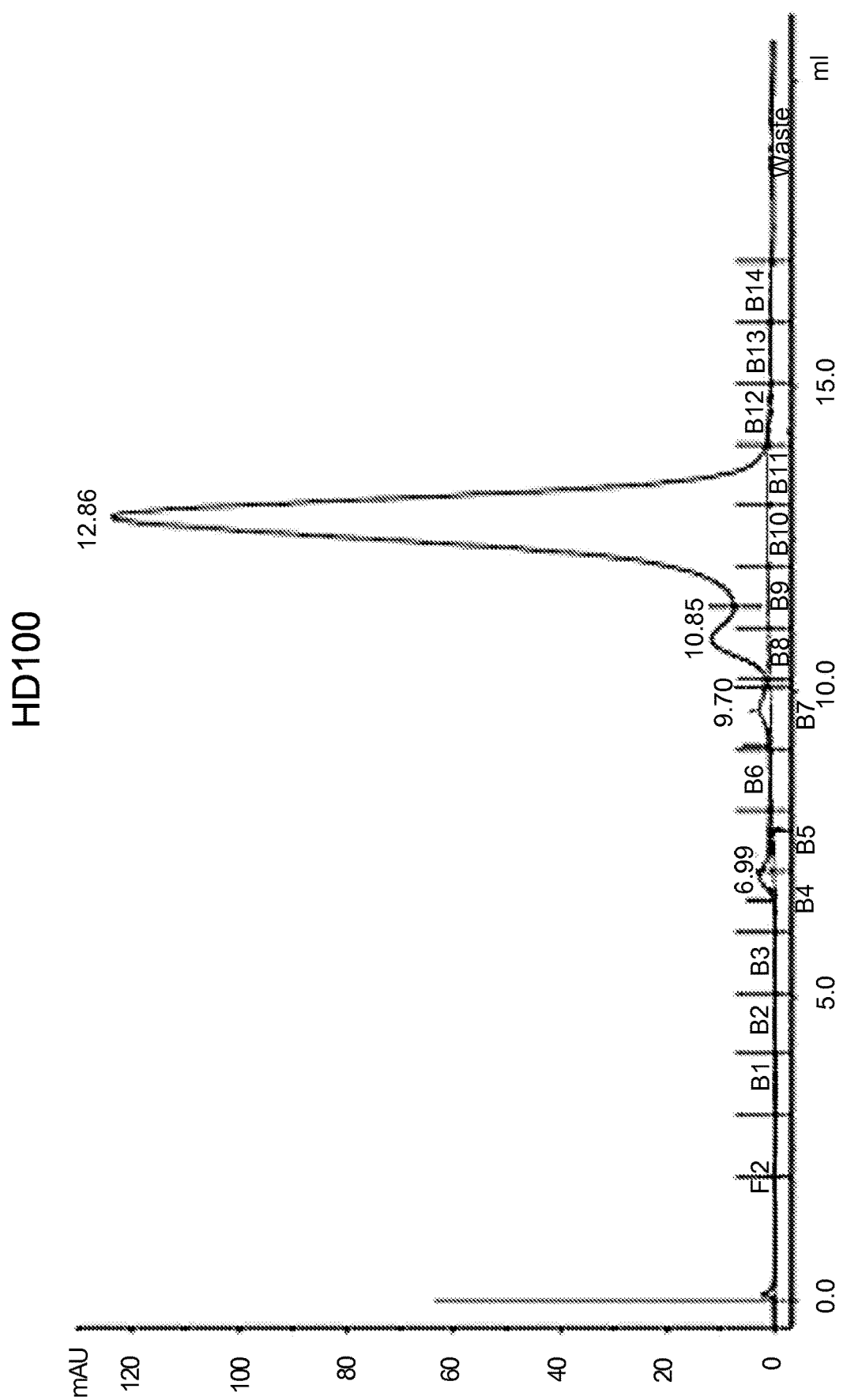

Provided herein are antibody constructs (also referred to as heterodimer pairs) comprising a first heterodimer and a second heterodimer wherein each heterodimer comprises an immunoglobulin heavy chain or fragment thereof and an immunoglobulin light chain. At least one of the heterodimers comprises one or more amino acid modifications in the immunoglobulin heavy chain constant domain 1 ($C_{H1}$) and one or more amino acid modifications in the immunoglobulin light chain constant domain ($C_L$); one or more amino acid modifications in the immunoglobulin heavy chain variable domain ($V_H$) and one or more amino acid modifications in the immunoglobulin light chain variable domain ($V_L$); or a combination of the preceding amino acid modifications to both the constant and variable domains of the heavy and light chains. The amino acids that are modified are part of the interface between the light chain and heavy chain and are modified in order to create preferential pairing between each heavy chain and the desired light chain such that when the two heavy chains and two light chains of the heterodimer are co-expressed in a mammalian cell, the heavy chain of the first heterodimer preferentially pairs with one of the light chains rather than the other. Likewise, the heavy chain of the second heterodimer preferentially pairs with the second light chain rather than first.

As noted above, specific combinations of the amino acid modifications described above promote preferential pairing of heavy chains with specific light chains, thus enabling bi-specific monoclonal antibody (Mab) expression to occur with negligible mispairing, and minimizing the need to purify the desired heterodimers from undesired, or mispaired products. The heterodimers exhibit comparable thermal stability to heterodimers that do not include the amino acid modifications, and also demonstrate binding affinity for antigen that is comparable to heterodimers that do not include the amino acid modifications.

The first and second heterodimers, when co-expressed as a heterodimer pair, can be used to create bi-specific antibodies targeting two different therapeutic targets or targeting two distinct epitopes (overlapping or non-overlapping) within the same antigen.

The invention further provides a method of preparing the heterodimer pairs according to the invention, by co-expressing the heterodimers in a mammalian cell.

Definitions

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously. In addition, it should be understood that the individual single chain polypeptides or immunoglobulin constructs derived from various combinations of the structures and substituents described herein are disclosed by the present application to the same extent as if each single chain polypeptide or heterodimer were set forth individually. Thus, selection of particular components to form individual single chain polypeptides or heterodimers is within the scope of the present disclosure The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

In the present application, amino acid names and atom names (e.g. N, O, C, etc.) are used as defined by the Protein DataBank (PDB) (www.pdb.org), which is based on the IUPAC nomenclature (IUPAC Nomenclature and Symbolism for Amino Acids and Peptides (residue names, atom names etc.), Eur. J. Biochem., 138, 9-37 (1984) together with their corrections in Eur. J. Biochem., 152, 1 (1985). The term "amino acid residue" is primarily intended to indicate an amino acid residue contained in the group consisting of the 20 naturally occurring amino acids, i.e. alanine (Ala or A), cysteine (Cys or C), aspartic acid (Asp or D), glutamic acid (Glu or E), phenylalanine (Phe or F), glycine (Gly or G), histidine (His or H), isoleucine (lie or 1), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "nucleotide sequence" or "nucleic acid sequence" is intended to indicate a consecutive stretch of two or more nucleotide molecules. The nucleotide sequence may be of genomic, cDNA, RNA, semisynthetic or synthetic origin, or any combination thereof.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing DNA into a cell.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, p-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and [0139] 8) Cysteine (C), Methionine (M) (see, e.g., Creighton, Proteins: Structures and Molecular Properties (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 50% identity, about 55% identity, 60% identity, about 65%, about 70%, about 75%, about 80%, about 85%, about 90%, about 95% or about 99% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

As used herein, "isolated" polypeptide or immunoglobulin construct means a construct or polypeptide that has been identified and separated and/or recovered from a component of its natural cell culture environment. Contaminant components of its natural environment are materials that would interfere with diagnostic or therapeutic uses for the heteromultimer, and may include enzymes, hormones, and other proteinaceous or non-proteinaceous solutes.

In certain embodiments, as used herein, "isolated" heterodimer, antibody constructs or antibody constructs described herein comprise heterodimer pairs or "isolated" heterodimer pairs that comprise a heterodimer or heterodimer pair that has been identified and separated and/or recovered from a component of its natural cell culture environment. Contaminant components of its natural environment are materials that would interfere with diagnostic or therapeutic uses for the heterodimer or antibody construct, and may include enzymes, hormones, and other proteinaceous or non-proteinaceous solutes.

The heterodimers and antibody constructs and heterodimer pairs are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homodimers). Expressed in terms of purity, substantial homogeneity means that the amount of by-products does not exceed 10%, and preferably is below 5%, more preferably below 1%, most preferably below 0.5%, wherein the percentages are by weight.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

As used herein, the terms "antibody" and "immunoglobulin" are used interchangeable. An "antibody" or "immunoglobulin" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin isotypes, IgG, IgM, IgA, IgD, and IgE, respectively. Further, the antibody can belong to one of a number of subtypes, for instance, the IgG can belong to the IgG1, IgG2, IgG3, or IgG4 isotypes.

An exemplary immunoglobulin (antibody) structural unit is composed of two pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. In certain embodiments, the immunoglobulin constructs comprise at least one immunoglobulin domain from IgG, IgM, IgA, IgD, or IgE connected to a therapeutic polypeptide. In some embodiments, the immunoglobulin domain comprised in an immunoglobulin construct provided herein, is from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

The term "preferential pairing" is used herein in relation to the pairing of immunoglobulin heavy chains with immunoglobulin light chains in the antibody constructs and heterodimer pairs described herein. It is known in the art that if an immunoglobulin heavy chain (H1) is co-expressed with two different immunoglobulin light chains (L1 and L2), typically, H1 will pair equally with each of the light chains, resulting in an approximate 50:50 mixture of H1 paired with L1 and H1 paired with L2. In this context, "preferential pairing" would occur between, for example, H1 and L1, if the amount of the H1-L1 heavy chain-light chain heterodimer was greater than the amount of the H1-L2 heterodimer when H1 is co-expressed with both L1 and L2. Thus, in this case, H1 preferentially pairs with L1 relative to L2.

Antibody heavy chains pair with antibody light chains and meet at an "interface." The "interface" comprises those "contact" amino acid residues in the first polypeptide that interact with one or more "contact" amino acid residues in the interface of the second polypeptide. As used herein, the interface comprises the CH3 domain of an Fc region that preferably is derived from an IgG antibody and most preferably a human IgG1 antibody.

The immunoglobulin/antibody heavy chain that is to be associated with an immunoglobulin/antibody light chain meet at an "interface." The immunoglobulin light chain associates with the immunoglobulin heavy chain via the "interface". The "interface" comprises those "contact" amino acid residues in the immunoglobulin heavy chain that interact with one or more "contact" amino acid residues in the interface of the immunoglobulin light chain. As used herein, the interface comprises the $V_H$ and $C_{H1}$ domains of the immunoglobulin heavy chain and the $V_L$ and $C_L$ domains of the immunoglobulin light chain. The "interface" preferably is derived from an IgG antibody and most preferably a human IgG1 antibody.

The term "amino acid modifications" as used herein includes, but is not limited to, amino acid insertions, deletions, substitutions, and rearrangements.

It will be understood that the numbering of the $V_L$, $V_H$, $C_L$, and $C_{H1}$ amino acid residues is according to Kabat as in Kabat et al., 1991, NIH Publication 91-3242, National Technical Information Service, Springfield, VA, unless otherwise indicated. The "EU index as set forth in Kabat" refers to the EU index numbering of the human IgG1 Kabat antibody.

A. Antibody Constructs/Heterodimer Pairs)

The antibody constructs described herein comprise a first heterodimer and a second heterodimer; each heterodimer obtained by pairing an immunoglobulin heavy chain with an immunoglobulin light chain. The structure and organization of the constant and variable domains of immunoglobulin heavy and light chains are well known in the art. Immunoglobulin heavy chains comprise one variable ($V_H$) domain, and three constant domains, $C_{H1}$, $C_{H2}$, and $C_{H3}$. Immunoglobulin light chains comprise one variable ($V_L$) domain and one constant ($C_L$) domain.

The antibody constructs and heterodimer pairs described herein comprise a first heterodimer and a second heterodimer, each heterodimer comprising an immunoglobulin/antibody heavy chain or fragment thereof having at least a $V_H$ and $C_{H1}$ domain, and an immunoglobulin/antibody light chain having a $V_L$ domain and a $C_L$ domain. In one embodiment, both heterodimers of the heterodimer pair and antibody construct comprise a full-length immunoglobulin heavy chain. In another embodiment, both heterodimers of the heterodimer pair or antibody construct comprise a fragment of the immunoglobulin heavy chain that includes at least a $V_H$ and a $C_{H1}$ domain. In one embodiment, both heterodimers of the heterodimer pair comprise an amino terminal fragment of the immunoglobulin heavy chain that comprises at least a $V_H$ and a $C_{H1}$ domain. In another embodiment, both heterodimers of the heterodimer pair comprise a carboxy terminal fragment of the immunoglobulin heavy chain that comprises at least a $V_H$ and a $C_{H1}$ domain.

Each heterodimer of the heterodimer pair binds specifically to an antigen or epitope. In one embodiment, the immunoglobulin heavy chain and the immunoglobulin light chain of each heterodimer is derived or engineered from a known therapeutic antibody. A therapeutic antibody is one that effective in treating a disease or disorder in a mammal with or predisposed to the disease or disorder. Suitable therapeutic antibodies from which each heterodimer can be derived include, but are not limited to abagovomab, adalimumab, alemtuzumab, aurograb, bapineuzumab, basiliximab, belimumab, bevacizumab, briakinumab, canakinumab, catumaxomab, certolizumab pegol, cetuximab, daclizumab, denosumab, efalizumab, galiximab, gemtuzumab ozogamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranibizumab, reslizumab, rituximab, teplizumab, tocilizumab/atlizumab, tosituomomab, trastuzumab, Proxinium™, Rencarex™, ustekinumab, and zalutumumab.

In one embodiment, the immunoglobulin heavy chain and the immunoglobulin light chain of each heterodimer are derived or engineered from an antibody that binds a molecule including, but not limited to, the following list of proteins, as well as subunits, domains, motifs and epitopes belonging to the following list of proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR, VEGFR; interferons such as alpha interferon (.alpha.-IFN), beta interferon (.beta.-IFN) and gamma interferon (.gamma.-IFN); protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as AFGF and PFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins; CD proteins such as CD2, CD3, CD4, CD8, CD11a, CD14, CD18, CD19, CD20, CD22, CD23, CD25, CD33, CD34, CD40, CD40L, CD52, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13; TNF.alpha., superoxide dismutase; T-cell receptors; surface membrane proteins; decay accelerating factor; viral antigen such as, for example, a portion of the AIDS envelope, e.g., gp120; transport proteins; homing receptors; addressins; regulatory proteins; cell adhesion molecules such as LFA-1, Mac 1, p150.95, VLA-4, ICAM-1, ICAM-3 and VCAM, a4/p7 integrin, and (Xv/p3 integrin including either a or subunits thereof, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, .alpha.V.beta.3, .alpha.V.beta.5 and .alpha.4.beta.7; a member of an apoptosis pathway; IgE; blood group antigens; flk2/flt3 receptor; obesity (OB) receptor; mp1 receptor; CTLA-4; protein C; an Eph receptor such as EphA2, EphA4, EphB2, etc.; a Human Leukocyte Antigen (HLA) such as HLA-DR; complement proteins such as complement receptor CR1, C1Rq and other complement factors such as C3, and C5; a glycoprotein receptor such as GpIb.alpha., GPIIb/IIIa and CD200; and fragments of any of the above-listed polypeptides.

In an embodiment, the immunoglobulin heavy and light chains of each heterodimer are derived or engineered from antibodies that specifically bind cancer antigens including, but not limited to, ALK receptor (pleiotrophin receptor), pleiotrophin, KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); polymorphic epithelial mucin antigen; human milk fat globule antigen; colorectal tumor-associated antigens such as: CEA, TAG-72, C017-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 514 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); polymorphic epithelial mucin (PEM); malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; Va4-D5; D.sub.156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E.sub.1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T.sub.5A.sub.7 found in myeloid cells; R.sub.24 found in melanoma; 4.2, G.sub.D3, D1.1, OFA-1, G.sub.M2, OFA-2, G.sub.D2, and M1:22:25:8 found in embryonal carcinoma cells and SSEA-3 and SSEA-4 found in 4 to 8-cell stage embryos; Cutaneous Tcell Lymphoma antigen; MART-1 antigen; Sialy Tn (STn) antigen; Colon cancer antigen NY-CO-45; Lung cancer antigen NY-LU-12 valiant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4-a, MAGE-4-b and MAGE-X2; Cancer-Testis Antigen (NY-EOS-1) and fragments of any of the above-listed polypeptides.

Human antibodies can be grouped into isotypes including IgG, IgA, IgE, IgM, and IgD. In one embodiment, the immunoglobulin heavy and light chains of the heterodimer are derived from an IgG isotype. In another embodiment, the immunoglobulin heavy and light chains of the heterodimer are derived from an IgA isotype. In another embodiment, the immunoglobulin heavy and light chains of the heterodimer are derived from an IgE isotype. In another embodiment, the immunoglobulin heavy and light chains of the heterodimer are derived from an IgM isotype. In another embodiment, the immunoglobulin heavy and light chains of the heterodimer are derived from an IgD isotype.

Human IgG antibodies can also be divided into the subclasses IgG1, IgG2, IgG3, and IgG4. Thus, in some embodiments, it is contemplated that the heterodimer immunoglobulin heavy and light chains can be derived from an IgG1, IgG2, IgG3, or IgG4 subclass of antibodies.

Each heterodimer of the heterodimer pair binds specifically to an epitope or antigen. In one embodiment, each heterodimer of the heterodimer pair binds to the same epitope. In another embodiment, the first heterodimer of the heterodimer pair specifically binds to an epitope on one antigen and the second heterodimer of the heterodimer pair binds specifically to a different epitope on the same antigen. In another embodiment, the first heterodimer of the heterodimer pair specifically binds to an epitope on a first antigen, and the second heterodimer of the heterodimer pair specifically binds to an epitope on a second antigen that is different from the first antigen. For example, in one embodiment, the first heterodimer binds specifically to Tissue Factor, while the second heterodimer binds specifically to antigen Her2(ErbB2). In another embodiment, the first heterodimer binds specifically to a molecule or cancer antigen described above. In another embodiment, the second heterodimer binds specifically to a molecule or cancer antigen described above. In yet another embodiment, the first heterodimer binds specifically to antigen CD3, while the second heterodimer binds specifically to antigen CD19.

A.1 Amino Acid Modifications to Heterodimer Immunoglobulin Heavy and Light Chains At least one of the heterodimers of the heterodimer pair comprises one or more amino acid modifications to their immunoglobulin heavy and/or immunoglobulin light chains such that when the two heavy chains and two light chains of the heterodimer pair are co-expressed in a mammalian cell, the heavy chain of the first heterodimer preferentially pairs with one of the light chains rather than the other. Likewise, the heavy chain of the second heterodimer preferentially pairs with the second light chain rather than the first. This preferential pairing of one heavy chain with one of two co-expressed light chains is based on co-expression sets comprising one immunoglobulin heavy chain and two immunoglobulin light chains where the immunoglobulin heavy chain preferentially pairs with one of the two immunoglobulin light chains over the other when the immunoglobulin heavy chain is co-expressed with both immunoglobulin light chains. Thus, a co-expression set comprises one immunoglobulin heavy chain, a first immunoglobulin light chain and a second immunoglobulin light chain.

As indicated above, in some embodiments, the immunoglobulin heavy chain and the immunoglobulin light chain of each heterodimer is derived or engineered from a known therapeutic antibody, or from an antibody that binds various molecules or cancer antigens. The amino acid and nucleotide sequences of numerous such molecules are readily available (see for example, GenBank: AJ308087.1 (Humanized anti-human tissue factor antibody D3H44 light chain variable region and CL domain); GenBank: AJ308086.1 (humanized anti-human tissue factor antibody D3H44 heavy chain variable region and CH1 domain); GenBank: HC359025.1 (Pertuzumab Fab light chain gene module); GenBank: HC359024.1 (Pertuzumab Fab heavy chain gene module); GenBank: GM685465.1 (Antibody Trastuzumab (=Herceptin)—wildtype; light chain); GenBank: GM685463.1 (Antibody Trastuzumab (=Herceptin)—wildtype; heavy chain); GenBank: GM685466.1 (Antibody Trastuzumab (=Herceptin)—GC-optimized light chain); and GenBank: GM685464.1 (Antibody Trastuzumab (=Herceptin)—GC-optimized heavy chain.

In one embodiment, the one or more amino acid modifications comprise one or more amino acid substitutions.

In one embodiment, the preferential pairing demonstrated in the co-expression set is established by modifying one or more amino acids that are part of the interface between the light chain and heavy chain. In one embodiment, the preferential pairing demonstrated in the co-expression set is established by modifying one or more amino acids in at least one of the $C_{H1}$ domain of the immunoglobulin heavy chain, the $C_L$ domain of a first immunoglobulin light chain and the $C_L$ domain of the second immunoglobulin light chain.

In one embodiment the one or amino acid modifications are limited to the conserved framework residues of the variable ($V_H$, $V_L$) and constant ($C_{H1}$, $C_L$) domains as indicated by the Kabat numbering of residues. For example, Almagro [Frontiers In Bioscience (2008) 13: 1619-1633] provides a definition of the framework residues on the basis of Kabat, Chotia, and IMGT numbering schemes.

In one embodiment, at least one of the heterodimers comprises one or more mutations introduced in the immunoglobulin heavy and immunoglobulin light chains that are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces. In one embodiment, at least one of the heterodimers comprises one or more mutations where the mutations introduced in the immunoglobulin heavy and immunoglobulin light chains introduce a new hydrogen bond across the light and heavy chain at the interface.

Non-limiting examples of suitable co-expression sets are shown in Table 1, showing amino acid modifications in one immunoglobulin heavy chain $C_{H1}$ domain (H1) and the two immunoglobulin light chain $C_L$ domains (L1 and L2) of the heterodimers, where H1 preferentially pairs with L1 when H1, L1 and L2 are co-expressed. The amino acid modifications shown in these co-expression sets are based on the amino acid sequence of anti-tissue factor antibody D3H44 immunoglobulin heavy and light chains.

TABLE 1

Selected co-expression sets with constant domain modifications to one immunoglobulin heavy chain (H1) and two immunoglobulin light chains, L1 and L2, where H1 preferentially pairs with L1

| Set # | H1_mutation* | L1_mutation | L2_mutation |
|---|---|---|---|
| C500 | WT | WT | F116A |
| C503 | WT | WT | F98L |
| C505 | A139W_V190S | F116S | F118W_V133S |
| C507 | A139W_V190S | F116A | F118W_V133S |
| C509 | A139W | WT | F116A |
| C510 | A139V_V190S | F116A | F118W_V133S |

TABLE 1-continued

Selected co-expression sets with constant domain modifications to one
immunoglobulin heavy chain (H1) and two immunoglobulin light chains, L1 and L2,
where H1 preferentially pairs with L1

| Set # | H1_mutation* | L1_mutation | L2_mutation |
| --- | --- | --- | --- |
| C511 | A139V_V190S | WT | F118W_V133S |
| C513 | A139I_V190S | F116A | F118W_V133S |
| C514 | A139I_V190S | WT | F118W_V133S |
| C515 | A139G_V190A | L135W_N137A | F116A_L135A |
| C517 | A139G_V190A | L135W | F116A_L135A |
| C519 | A139G_V190A | L135W | F116A_L135V |
| C521 | S188I | WT | S176V_T178L |
| C523 | V190G | F116A | F118W_V133S |
| C524 | V190G | F116S | F118W_V133S |
| C525 | S188L_V190Y | V133S | S176L |
| C527 | F174V_P175S_S188G | S176L | WT |
| C530 | D146G_Q179R | Q124E_Q160E_T178D | Q160K_T178R |
| C532 | L143A_D146G_Q179R | Q124E_V133W_Q160E_T180E | V133A_Q160K_T178R |

*Kabat numbering

Additional non-limiting examples of suitable co-expression sets are shown in Table 2, showing amino acid modifications in one immunoglobulin heavy chain $C_{H1}$ domain (H2) and the two immunoglobulin light chain $C_L$ domains (L1 and L2) of the heterodimers, where H2 preferentially pairs with L2 when H2, L1 and L2 are co-expressed:

TABLE 2

Selected co-expression sets with constant domain modifications to one
immunoglobulin heavy chain (H2) and two immunoglobulin light chains, L1 and L2,
where H2 preferentially pairs with L2

| Set # | H2_mutation | L1_mutation | L2_mutation |
| --- | --- | --- | --- |
| C501 | A139W_V190S | WT* | F116A |
| C502 | A139W_V190A | WT | F116A |
| C504 | F100W | WT | F98L |
| C506 | A139W | F116S | F118W_V133S |
| C508 | A139V | F116A | F118W_V133S |
| C512 | A139I | WT | F118W_V133S |
| C516 | A139W | L135W_N137A | F116A_L135A |
| C518 | A139W | L135W | F116A_L135A |
| C520 | A139W | L135W | F116A_L135V |
| C522 | WT | WT | S176V_T178L |
| C526 | F174V_P175S_S188G | V133S | S176L |
| C528 | F174V_S188L | S176L | WT |
| C529 | S188L | S176L | WT |
| C531 | K145T_Q179D_S188L | Q124E_Q160E_T178D | Q160K_T178R |
| C533 | K145T_Q179D_S188F | Q124E_V133W_Q160E_T180E | V133A_Q160K_T178R |

*WT refers to a wild-type immunoglobulin chain without amino acid mutations

In one embodiment, the co-expression set comprises an immunoglobulin heavy chain with at least one amino acid modification in the $C_{H1}$ domain, a first immunoglobulin light chain with at least one amino acid modification in the $C_L$ domain, and a second immunoglobulin light chain without any amino acid modifications in the $C_L$ domain. In another embodiment, the co-expression set comprises an immunoglobulin heavy chain with at least one amino acid modification in the $C_{H1}$ domain, a first immunoglobulin light chain with at least one amino acid modification in the $C_L$ domain, and a second immunoglobulin light chain with at least one amino acid modification in the $C_L$ domain. In another embodiment, the co-expression set comprises an immunoglobulin heavy chain with at least one amino acid modification in the $C_{H1}$ domain, a first immunoglobulin light chain with at least two amino acid modifications in the $C_L$ domain, and a second immunoglobulin light chain with at least two amino acid modifications in the $C_L$ domain. In another embodiment, the co-expression set comprises an immunoglobulin heavy chain with at least one amino acid modification in the $C_{H1}$ domain, a first immunoglobulin light chain with at least two amino acid modifications in the $C_L$ domain, and a second immunoglobulin light chain with at least one amino acid modification in the $C_L$ domain.

In one embodiment, the co-expression set comprises an immunoglobulin heavy chain with no amino acid modifications in the $C_{H1}$ domain, a first immunoglobulin light chain with no amino acid modifications in the $C_L$ domain, and a second immunoglobulin light chain with at least one amino acid modification in the $C_L$ domain. In one embodiment, the co-expression set comprises an immunoglobulin heavy chain with no amino acid modifications in the $C_{H1}$ domain, a first immunoglobulin light chain with no amino acid modifications in the $C_L$ domain, and a second immunoglobulin light chain with at least two amino acid modifications in the $C_L$ domain.

In one embodiment, the co-expression set comprises an immunoglobulin heavy chain with at least two amino acid modifications in the $C_{H1}$ domain, a first immunoglobulin light chain with no amino acid modifications in the $C_L$ domain, and a second immunoglobulin light chain with at least one amino acid modification in the $C_L$ domain. In one embodiment, the co-expression set comprises an immunoglobulin heavy chain with at least two amino acid modifications in the $C_{H1}$ domain, a first immunoglobulin light chain with at least one amino acid modifications in the $C_L$ domain, and a second immunoglobulin light chain with at least one amino acid modification in the $C_L$ domain. In one embodiment, the co-expression set comprises an immunoglobulin heavy chain with at least two amino acid modifications in the $C_{H1}$ domain, a first immunoglobulin light chain with at least one amino acid modification in the $C_L$ domain, and a second immunoglobulin light chain with at least two amino acid modifications in the $C_L$ domain. In one embodiment, the co-expression set comprises an immunoglobulin heavy chain with at least two amino acid modifications in the $C_{H1}$ domain, a first immunoglobulin light chain with at least two amino acid modifications in the $C_L$ domain, and a second immunoglobulin light chain with at least two amino acid modifications in the $C_L$ domain. In one embodiment, the co-expression set comprises an immunoglobulin heavy chain with at least two amino acid modifications in the $C_{H1}$ domain, a first immunoglobulin light chain with at least three amino acid modifications in the $C_L$ domain, and a second immunoglobulin light chain with at least two amino acid modifications in the $C_L$ domain.

In one embodiment, the co-expression set comprises an immunoglobulin heavy chain with at least three amino acid modifications in the $C_{H1}$ domain, a first immunoglobulin light chain with no amino acid modifications in the $C_L$ domain, and a second immunoglobulin light chain with at least one amino acid modification in the $C_L$ domain. In one embodiment, the co-expression set comprises an immunoglobulin heavy chain with at least three amino acid modifications in the $C_{H1}$ domain, a first immunoglobulin light chain with at least one amino acid modification in the $C_L$ domain, and a second immunoglobulin light chain with at least one amino acid modification in the $C_L$ domain. In one embodiment, the co-expression set comprises an immunoglobulin heavy chain with at least three amino acid modifications in the $C_{H1}$ domain, a first immunoglobulin light chain with at least three amino acid modifications in the $C_L$ domain, and a second immunoglobulin light chain with at least two amino acid modifications in the $C_L$ domain. In one embodiment, the co-expression set comprises an immunoglobulin heavy chain with at least three amino acid modifications in the $C_{H1}$ domain, a first immunoglobulin light chain with at least four amino acid modifications in the $C_L$ domain, and a second immunoglobulin light chain with at least three amino acid modifications in the $C_L$ domain.

In one embodiment, the preferential pairing demonstrated in the co-expression set is established by modifying one or more amino acids in at least one of the $V_H$ domain of the immunoglobulin heavy chain, the $V_L$ domain of a first immunoglobulin light chain and the $V_L$ domain of the second immunoglobulin light chain. Non-limiting examples of suitable co-expression sets are shown in Table 3, showing amino acid modifications in one immunoglobulin heavy chain $V_H$ domain (H1) and the two immunoglobulin light chain $V_L$ domains (L1 and L2) of the heterodimers, where H1 preferentially pairs with L1 when H1, L1 and L2 are co-expressed:

TABLE 3

Selected co-expression sets with variable domain modifications to one immunoglobulin heavy chain and two immunoglobulin light chains, where H1 preferentially pairs with L1

| Set # | H1_mutation* | L1_mutation | L2_mutation |
|---|---|---|---|
| V001 | V37W_W103H | F98L | F98W |
| V004 | V37W_W103H | F98L | P44W |
| V005 | V37A_W103H | P44W | F98L |
| V006 | V37W_W103F | F98L | F98W |
| V007 | V37W | F98A | F98W |
| V009 | V37W | F98A | WT |
| V011 | V37I | WT | F98L |
| V013 | V37A_W103V | P44W | F98A |
| V015 | V37A_W103H | P44W | F98A |
| V016 | V37A_W103H | P44W | F98W |
| V020 | L45W | Y87G | P44W |
| V022 | WT | F98W | F98A |
| V023 | WT | WT | F98A |
| V024 | Q39R | Q38E | F98A |
| V026 | Q39R | Q38E | WT |
| V028 | Q39R | Q38E | Q38R |
| V030 | Q39R | Q38D | Q38R |
| V032 | Q39M | Q38M | Q38E |
| V034 | Q39K | Q38N_T85E | Q38N_T85K |
| V037 | Q39E | Q38R | F98A |
| V039 | Q39D | Q38R | Q38D |
| V040 | V37E | L89R_F98T | WT |
| V042 | V37E_F100D | L89R_F98W | WT |
| V044 | V37E_F100D | L89R_F98W | F98Y |

*Kabat numbering

Additional non-limiting examples of suitable co-expression sets are depicted in Table 4, showing amino acid modifications in one immunoglobulin heavy chain $V_H$ domain (H2) and the two immunoglobulin light chain $V_L$ domains (L1 and L2) of the heterodimers, where H2 preferentially pairs with L2 when H2, L1 and L2 are co-expressed:

TABLE 4

Selected co-expression sets with variable domain modifications to one immunoglobulin heavy chain and two immunoglobulin light chains, where H2 preferentially pairs with L2

| Set # | H2_mutation | L1_mutation | L2_mutation |
|---|---|---|---|
| V002 | V37I | F98L | F98W |
| V003 | WT | F98L | F98W |
| V005 | V37A_W103H | F98L | P44W |
| V007 | V37W | F98W | F98A |
| V008 | V37I | F98A | F98W |
| V009 | V37W | WT | F98A |
| V010 | V37I | F98A | WT |
| V012 | F100W | WT | F98L |
| V014 | V37W | P44W | F98A |
| V017 | V37A_W103V | P44W | F98W |
| V018 | V37A_W103V | P44W | F98L |
| V019 | V37I_F100W | P44W | F98L |
| V021 | V37A_W103H | Y87G | P44W |
| V025 | V37W | Q38E | F98A |
| V027 | WT | Q38E | WT |
| V029 | Q39E | Q38E | Q38R |
| V030 | Q39R | Q38R | Q38D |
| V031 | Q39E | Q38D | Q38R |
| V033 | Q39R | Q38M | Q38E |
| V035 | Q39D | Q38N_T85E | Q38N_T85K |
| V036 | Q39E | Q38N_T85E | Q38N_T85K |
| V038 | V37W | Q38R | F98A |
| V041 | WT | L89R_F98T | WT |
| V043 | WT | L89R_F98W | WT |
| V045 | V37S_A97K | L89R_F98W | F98Y |

In one embodiment, the co-expression set comprises an immunoglobulin heavy chain with no amino acid modifications in the $V_H$ domain, a first immunoglobulin light chain with no amino acid modifications in the $V_L$ domain, and a second immunoglobulin light chain with at least one amino acid modification in the $V_L$ domain. In one embodiment, the co-expression set comprises an immunoglobulin heavy chain with no amino acid modifications in the $V_H$ domain, a first immunoglobulin light chain with no amino acid modifications in the $V_L$ domain, and a second immunoglobulin light chain with at least two amino acid modifications in the $V_L$ domain.

In one embodiment, the co-expression set comprises an immunoglobulin heavy chain with at least one amino acid modification in the $V_H$ domain, a first immunoglobulin light chain with no amino acid modifications in the $V_L$ domain, and a second immunoglobulin light chain with at least one amino acid modification in the $V_L$ domain. In one embodiment, the co-expression set comprises an immunoglobulin heavy chain with at least one amino acid modification in the $V_H$ domain, a first immunoglobulin light chain with at least one amino acid modification in the $V_L$ domain, and a second immunoglobulin light chain with at least one amino acid modification in the $V_L$ domain. In one embodiment, the co-expression set comprises an immunoglobulin heavy chain with at least one amino acid modification in the $V_H$ domain, a first immunoglobulin light chain with at least two amino acid modifications in the $V_L$ domain, and a second immunoglobulin light chain with at least two amino acid modifications in the $V_L$ domain.

In one embodiment, the co-expression set comprises an immunoglobulin heavy chain with at least two amino acid modifications in the $V_H$ domain, a first immunoglobulin light chain with no amino acid modifications in the $V_L$ domain, and a second immunoglobulin light chain with at least one amino acid modification in the $V_L$ domain. In one embodiment, the co-expression set comprises an immunoglobulin heavy chain with at least two amino acid modifications in the $V_H$ domain, a first immunoglobulin light chain with at least two amino acid modifications in the $V_L$ domain, and a second immunoglobulin light chain with at least one amino acid modification in the $V_L$ domain. In one embodiment, the co-expression set comprises an immunoglobulin heavy chain with at least two amino acid modifications in the $V_H$ domain, a first immunoglobulin light chain with at least one amino acid modification in the $V_L$ domain, and a second immunoglobulin light chain with at least one amino acid modification in the $V_L$ domain.

In one embodiment, the co-expression sets shown in Tables 1 to 4 are combined to provide a combination comprising two distinct immunoglobulin heavy chains (H1 and H2) and two distinct immunoglobulin light chains (L1 and L2), where H1 preferentially pairs with L1 and H2 preferentially pairs with L2 when H1, H2, L1, and L2 are co-expressed. In one embodiment, a co-expression set from Table 1, comprising modifications to the $C_{H1}$ domain of the heavy chain and/or the $C_L$ domain of the light chains is combined with a co-expression set from Table 2, also comprising modifications to the $C_H$ domain of the heavy chain and/or the $C_L$ domain of the light chains.

Non-limiting examples of such combinations are shown in Table 5:

TABLE 5

Combinations of co-expression sets comprising constant domain modifications

| Set # | Set # | H1_mutation* | L1_mutation | H2_mutation | L2_mutation |
|---|---|---|---|---|---|
| C500 | C501 | WT | WT | A139W_V190S | F116A |
| C500 | C502 | WT | WT | A139W_V190A | F116A |
| C503 | C504 | WT | WT | F100W | F98L |
| C505 | C506 | A139W_V190S | F116S | A139W | F118W_V133S |
| C507 | C508 | A139W_V190S | F116A | A139V | F118W_V133S |
| C509 | C501 | A139W | WT | A139W_V190S | F116A |
| C509 | C502 | A139W | WT | A139W_V190A | F116A |
| C510 | C508 | A139V_V190S | F116A | A139V | F118W_V133S |
| C511 | C512 | A139V_V190S | WT | A139I | F118W_V133S |
| C513 | C508 | A139I_V190S | F116A | A139V | F118W_V133S |
| C514 | C512 | A139I_V190S | WT | A139I | F118W_V133S |
| C515 | C516 | A139G_V190A | L135W_N137A | A139W | F116A_L135A |
| C517 | C518 | A139G_V190A | L135W | A139W | F116A_L135A |
| C519 | C520 | A139G_V190A | L135W | A139W | F116A_L135V |
| C521 | C522 | S188I | WT | WT | S176V_T178L |
| C523 | C508 | V190G | F116A | A139V | F118W_V133S |
| C524 | C506 | V190G | F116S | A139W | F118W_V133S |
| C525 | C526 | S188L_V190Y | V133S | F174V_P175S_S188G | S176L |
| C527 | C528 | F174V_P175S_S188G | S176L | F174V_S188L | WT |
| C527 | C529 | F174V_P175S_S188G | S176L | S188L | WT |
| C530 | C531 | D146G_Q179R | Q124E_Q160E_T178D | K145T_Q179D_S188L | Q160K_T178R |
| C532 | C533 | L143A_D146G_Q179R | Q124E_V133W_Q160E_T180E | K145T_Q179D_S188F | V133A_Q160K_T178R |

*Kabat numbering

In one embodiment, a co-expression set from Table 3, comprising modifications to the $V_H$ domain of the heavy chain and/or the $V_L$ domain of the light chains is combined with a co-expression set from Table 4, also comprising modifications to the $V_H$ domain of the heavy chain and/or the $V_L$ domain of the light chains. Non-limiting examples of such combinations are shown in Table 6:

TABLE 6

Combinations of co-expression sets comprising variable domain modifications

| Set # | Set # | H1_mutation* | L1_mutation | H2_mutation | L2_mutation |
|---|---|---|---|---|---|
| V001 | V002 | V37W_W103H | F98L | V37I | F98W |
| V001 | V003 | V37W_W103H | F98L | WT | F98W |
| V004 | V005 | V37W_W103H | F98L | V37A_W103H | P44W |
| V006 | V002 | V37W_W103F | F98L | V37I | F98W |
| V006 | V003 | V37W_W103F | F98L | WT | F98W |
| V007 | V008 | V37W | F98A | V37I | F98W |
| V009 | V010 | V37W | F98A | V37I | WT |
| V011 | V012 | V37I | WT | F100W | F98L |
| V013 | V014 | V37A_W103V | P44W | V37W | F98A |
| V015 | V014 | V37A_W103H | P44W | V37W | F98A |
| V016 | V017 | V37A_W103H | P44W | V37A_W103V | F98W |
| V005 | V018 | V37A W103H | P44W | V37A_W103V | F98L |
| V005 | V019 | V37A_W103H | P44W | V37I_F100W | F98L |
| V020 | V021 | L45W | Y87G | V37A_W103H | P44W |
| V022 | V007 | WT | F98W | V37W | F98A |
| V023 | V009 | WT | WT | V37W | F98A |
| V024 | V025 | Q39R | Q38E | V37W | F98A |
| V026 | V027 | Q39R | Q38E | WT | WT |
| V028 | V029 | Q39R | Q38E | Q39E | Q38R |
| V030 | V031 | Q39R | Q38D | Q39E | Q38R |
| V032 | V033 | Q39M | Q38M | Q39R | Q38E |
| V034 | V035 | Q39K | Q38N_T85E | Q39D | Q38N_T85K |
| V034 | V036 | Q39K | Q38N_T85E | Q39E | Q38N_T85K |
| V037 | V038 | Q39E | Q38R | V37W | F98A |
| V039 | V030 | Q39D | Q38R | Q39R | Q38D |
| V040 | V041 | V37E | L89R_F98T | WT | WT |
| V042 | V043 | V37E_F100D | L89R_F98W | WT | WT |
| V044 | V045 | V37E_F100D | L89R_F98W | V37S_A97K | F98Y |

A.2 Transferability of Specific Amino Acid Modifications Identified Herein to Other Antibodies:

Although the specific amino acid modifications to immunoglobulin heavy and light chains identified above have been described with respect to the D3H44 anti-tissue factor extracellular domain antibody immunoglobulin heavy and light chains, it is contemplated that these amino acid modifications are transferable to other immunoglobulin heavy and light chains, resulting in similar patterns of preferential pairing of one immunoglobulin heavy chain with one of the two immunoglobulin light chains in view of the following.

The $V_H$:$V_L$ and $C_{H1}$:$C_L$ interface residues in the interface between immunoglobulin heavy and light chains are relatively well conserved (Padlan et al., 1986, Mol. Immunol. 23(9): 951-960). This sequence conservation, a result of evolutionary constraints, increases the likelihood that functionally active antibody binding domains will be formed during combinatorial pairing of light and heavy chains. As a result of this sequence conservation, it follows that sequence modifications in the specific examples noted above for D3H44, which drive preferential pairing, should also readily transfer to other heavy and light chain pairs (or heterodimers) with approximately equivalent results being obtained with respect to preferential pairing. This is particularly the case for the $C_{H1}$ and $C_L$ domains. There is, however, some sequence variability at the antigen-binding site with respect to CDR (complementarity-determining regions) loop residues (and length), particularly for CDR-H3. Thus, in one embodiment, the heterodimer pairs according to the invention comprise heterodimers where at least one heterodimer comprises one or more amino acid modifications in the $V_H$ and/or $V_L$ domains that lie distal to the CDR loops when the amino acid sequence of the antigen-binding site is significantly different from that of the D3H44 antibody. In another embodiment, the heterodimer pairs according to the invention comprise heterodimers where at least one heterodimer comprises one or more amino acid modifications in the $V_H$ and/or $V_L$ domains that lie proximal or distal to the CDR loops, when the amino acid sequence of the antigen-binding site is substantially the same as that of the D3H44 antibody.

In one embodiment, the amino acid modifications described herein are transferable to the immunoglobulin heavy and light chains of antibodies based on human or humanized IgG1/K.

Non-limiting examples of such IgG1/K chains include Ofatumumab (for human) or Trastuzumab, Pertuzumab or Bevacizumab (for humanized).

In another embodiment, the amino acid modifications described herein are transferable to the immunoglobulin heavy and light chains of antibodies which comprise commonly used $V_H$ and $V_L$ subgroups. Non-limiting examples of such antibodies include Pertuzumab.

In one embodiment, the amino acid modifications described herein are transferable to the immunoglobulin heavy and light chains of antibodies having a framework close to germline. Examples of such antibodies include Obinutuzumab.

In one embodiment, the amino acid modifications described herein are transferable to the immunoglobulin heavy and light chains of antibodies having a $V_H$:$V_L$ interdomain angle close to observed average for heavy and light chain pairs. An example of this type of antibody includes, but is not limited to Pertuzumab. In another embodiment, the amino acid modifications described herein are transferable to the immunoglobulin heavy and light chains of antibodies having canonical $C_L$ and $C_{H1}$ domains. Suitable examples of such antibodies include, but are not limited to Trastuzumab.

An object of the present invention is to provide engineered immunoglobulin heavy chain-light chain pairs and uses thereof. In one aspect of the invention is provided an antibody construct comprising at least a first heterodimer and a second heterodimer, said first heterodimer comprising a first immunoglobulin heavy chain polypeptide (H1), and a first immunoglobulin light chain polypeptide (L1); and said second heterodimer comprising a second immunoglobulin heavy chain polypeptide (H2), and a second immunoglobulin light chain polypeptide (L2), wherein H1 and H2 each comprise at least a heavy chain variable domain (VH domain), fragment or derivative thereof; and a heavy chain constant domain (CH1 domain), fragment or derivative thereof; and wherein L1 and L2 each comprise at least a light chain variable domain (VL domain), fragment or derivative thereof; and a light chain constant domain (CL domain), fragment or derivative thereof; and at least one of H1, H2, L1 and L2 comprises at least one amino acid modification of at least one constant domain and at least one variable domain such that H1 pairs preferentially with L1 as compared to L2, and/or H2 pairs preferentially with L2 as compared to L1, when H1, H2, L1 and L2 are co-expressed in a cell.

Provided herein is an antibody construct comprising at least a first heterodimer and a second heterodimer, said first heterodimer comprising a first immunoglobulin heavy chain polypeptide (H1), and a first immunoglobulin light chain polypeptide (L1); and said second heterodimer comprising a second immunoglobulin heavy chain polypeptide (H2), and a second immunoglobulin light chain polypeptide (L2);

wherein H1 and H2 each comprise at least a VH domain, fragment or derivative thereof; and a CH1 domain, fragment or derivative thereof; and L1 and L2 each comprise at least a VL domain, fragment or derivative thereof; and a CL domain, fragment or derivative thereof; and wherein at least one of H1, H2, L1 and L2 comprises at least one amino acid modification of a VH or VL domain and/or at least one amino acid modification of a CH or CL domain such that H1 pairs preferentially with L1 as compared to L2, and/or H2 pairs preferentially with L2 as compared to L1.

In an aspect is provided an antibody construct comprising at least a first heterodimer and a second heterodimer, said first heterodimer comprising a first immunoglobulin heavy chain polypeptide (H1), and a first immunoglobulin light chain polypeptide (L1); and said second heterodimer comprising a second immunoglobulin heavy chain polypeptide (H2), and a second immunoglobulin light chain polypeptide (L2); wherein H1 and H2 each comprise at least a VH domain, fragment or derivative thereof; and a CH1 domain, fragment or derivative thereof, and at least one of H1 and H2 comprises a variant VH domain or variant CH1 domain; and wherein L1 and L2 each comprise at least a VL domain, fragment or derivative thereof, and a CL domain, fragment or derivative thereof, and at least one of L1 and L2 comprises a variant VL domain or variant CL domain; and wherein the variant domain(s) comprise at least one amino acid modification such that H1 pairs preferentially with L1 as compared to L2, and H2 pairs preferentially with L2 as compared to L1, when H1, H2, L1 and L2 are co-expressed in a cell.

In certain embodiments is an antibody construct described herein, wherein H1 further interacts preferentially with H2 as compared to forming a homodimer. In an embodiment is an antibody construct described herein, wherein when both L1 and L2 are co-expressed with at least one of H1 and H2, the relative yield of the at least one of H1-L1 and H2-L2 heterodimer pair to that of the corresponding mispaired H1-L2 or H2-L1 heterodimer pair is greater than 50%. In some embodiments is an antibody construct described herein, wherein the relative yield of desired H1-L1 or H2-L2 heterodimer pair to that of mispaired H1-L2 or H2-L1 heterodimer pair is greater than 60%. In an embodiment is an antibody construct described herein, wherein the relative yield of desired H1-L1 or H2-L2 heterodimer pair to that of mispaired H1-L2 or H2-L1 heterodimer pair is greater than 70%. In select embodiments is an antibody construct described herein, wherein the relative yield of desired H1-L1 or H2-L2 heterodimer pair to that of mispaired H1-L2 or H2-L1 heterodimer pair is greater than 80%. In another embodiment is an antibody construct described herein, wherein the relative yield of desired H1-L1 or H2-L2 heterodimer pair to that of mispaired H1-L2 or H2-L1 heterodimer pair is greater than 90%.

In certain embodiments is an antibody construct described herein, wherein the thermal stability as measured by the melting temperature (Tm) of at least one of said first and second heterodimers is within about 5° C. of the Tm of the corresponding heterodimer without the amino acid modifications. In certain embodiments is an antibody construct described herein, wherein the thermal stability as measured by the melting temperature (Tm) of each heterodimer comprising at least one amino acid modification is within about 5° C. of the Tm of the corresponding heterodimer without the amino acid modifications.

In certain embodiments is an antibody construct described herein, wherein the affinity of each heterodimer for its antigen is within about 50-fold of the affinity of the wild type heterodimer for the antigen.

In certain embodiments is an antibody construct described herein, wherein at least one of L1 and L2 comprises a variant VL domain comprising an amino acid modification of at least one of F98, P44, Q38 and T85. In an embodiment is an antibody construct described herein, wherein at least one of H1 and H2 comprises a variant VH domain comprising an amino acid modification of at least one of V37, Q39, W103 and F100. In some embodiments is an antibody construct described herein, wherein at least one of H1 and H2 comprises a variant CH1 domain comprising an amino acid modification of at least one of A139, L143, K145, D146, F174, P175, Q179, S188 and V190. In certain embodiments is an antibody construct described herein, wherein at least one of L1 and L2 comprises a variant CL domain comprising an amino acid modification of at least one of F116, F118, Q124, V133, L135, Q160, S176, T178 and T180.

In certain embodiments is an antibody construct described herein, wherein at least one of H1, and L1 comprises at least one variant domain comprising at least one amino acid modification resulting in favorable steric complementarity of amino acids when H1 pairs with L1 as compared to L2. In some embodiments is an antibody construct described herein, wherein at least one of H2 and L2 comprises at least one variant domain comprising at least one amino acid modification resulting in favorable steric complementarity of amino acids when H2 pairs with L2 as compared to L1. In select embodiments is an antibody construct described herein, wherein at least one of H1, and L1 comprises at least one variant domain comprising at least one amino acid modification resulting in favorable electrostatic complementarity between charged amino acids when H1 pairs with L1 as compared to L2. In an embodiment is an antibody construct described herein, wherein at least one of H2, and L2 comprises at least one variant domain comprising at least one amino acid modification resulting in favorable electrostatic complementarity between charged amino acids when H2 pairs with L2 as compared to L1.

In certain embodiments is an antibody construct described herein, which is multispecific. In some embodiments is an antibody construct described herein, which is bispecific.

In certain embodiments is an antibody construct described herein, wherein said construct is multivalent. In some embodiments is an antibody construct described herein, wherein said construct is bivalent.

Provided herein is a nucleic acid construct encoding any of the antibody constructs described above.

Also provided is an expression vector containing a nucleic acid construct described herein, and capable of expressing said nucleic acid construct in a host cell.

In certain embodiments is provided a prokaryotic or eukaryotic host cell comprising an expression vector described herein.

Provided herein is a method for the preparation of an antibody construct described above comprising the steps of: transforming a host cell with vectors comprising nucleic acid molecules encoding antibody construct; culturing the host cell under conditions that allow synthesis of said heteromultimer construct; and recovering said antibody construct from said culture.

Provided herein is a composition comprising a set of polypeptides comprising a first immunoglobulin light chain polypeptide (L1), a second immunoglobulin light chain polypeptide (L2), and a immunoglobulin heavy chain polypeptide (H1) or fragment thereof comprising a VH domain and a CH1 domain, wherein if H1 comprises at least one amino acid modification in the CH1 domain, then at least one of L1 and L2 comprise at least one amino acid modification in the CL domain; and if H1 comprises at least one amino acid modification in the VH domain, then at least one of L1 and L2 comprise at least one amino acid modification in the VL domain; and wherein H1 preferentially pairs with either L1 or L2 when co-expressed in a mammalian cell.

Provided herein is a pharmaceutical composition comprising an antibody construct described above. Also provided is use of the pharmaceutical composition for the treatment of cancer. In certain embodiments is provided the use of an antibody construct described herein, for the manufacture of a medicament for the treatment of cancer. In certain embodiments is a method of treatment of patient suffering from cancer by administering an antibody construct described herein to a patient in the need of such treatment.

Provided herein is a pharmaceutical composition comprising an antibody construct described above. Also provided is the use of the pharmaceutical composition for the treatment of vascular diseases. In certain embodiments is provided the use of an antibody construct described herein, for the manufacture of a medicament for the treatment of vascular diseases. In certain embodiments is provided a method of treatment of patient suffering from vascular diseases by administering an antibody construct described herein to a patient in the need of such treatment.

In some embodiments, certain subsets of the amino acid modifications described herein are utilized in variant domains in antibody constructs provided above.

A.3 Preferential Pairing

As described above, at least one heterodimer of the antibody construct/heterodimer pairs according to the invention comprise one or more amino acid modifications to their immunoglobulin heavy and/or immunoglobulin light chains such that when the two heavy chains (H1 and H2) and two light chains (L1 and L2) of the heterodimer pair are co-expressed in a mammalian cell, the heavy chain of the one heterodimer, for example H1, preferentially pairs with one of the light chains, for example L1, rather than the other light chain, L2, and the heavy chain of the other heterodimer, H2, preferentially pairs with the light chain, L2, rather than the light chain L1. In other words, the desired, preferential pairing is considered to be between H1 and L1, and between H2 and L2. Preferential pairing between, for example, H1 and L1 is considered to occur if the yield of the H1/L1 heterodimer is greater than the yield of the mispaired H1/L2 heterodimer when H1 is co-expressed with L1 and L2. Likewise, preferential pairing between H2 and L2 is considered to occur if the yield of the H2/L2 heterodimer is greater than the yield of the mispaired H2/L1 heterodimer when H2 is co-expressed with L1 and L2. In this context, an heterodimer comprising H1 and L1, or H2 and L2, is referred to herein as a preferentially paired, correctly paired, or desired heterodimer, while an heterodimer comprising H1 and L2, or H2 and L1, is referred to herein as a mispaired heterodimer.

Thus, in one embodiment, when one immunoglobulin heavy chain of a heterodimer is co-expressed with two immunoglobulin light chains, the relative yield of the desired heterodimer is greater than 55%. In another embodiment, when one immunoglobulin heavy chain of a heterodimer is co-expressed with two immunoglobulin light chains, the relative yield of the desired heterodimer is greater than 60%. In another embodiment, when one immunoglobulin heavy chain of a heterodimer is co-expressed with two immunoglobulin light chains, the relative yield of the desired heterodimer is greater than 70%. In another embodiment, when one immunoglobulin heavy chain of a heterodimer is co-expressed with two immunoglobulin light chains, the relative yield of the desired heterodimer is greater than 80%.

In another embodiment, when one immunoglobulin heavy chain of a heterodimer is co-expressed with two immunoglobulin light chains, the relative yield of the desired heterodimer is greater than 90%. In another embodiment, when one immunoglobulin heavy chain of a heterodimer is co-expressed with two immunoglobulin light chains, the relative yield of the desired heterodimer is greater than 95%.

In the above example, preferential pairing between H1/L1 is considered to occur if the amount of the desired H1/L1 heterodimer is greater than the amount of the mispaired H1/L2 heterodimer when H1 is co-expressed with L1 and L2. Similarly, preferential pairing between H2/L2 is considered to occur if the amount of the desired H2/L2 heterodimer is greater than the amount of the mispaired H2/L2 heterodimer when H2 is co-expressed with L1 and L2. Thus, in one embodiment, when one immunoglobulin heavy chain of a heterodimer is co-expressed with two immunoglobulin light chains, the ratio of the desired heterodimer to the mispaired heterodimer is greater than 1.25:1. In one embodiment, when one immunoglobulin heavy chain of a heterodimer is co-expressed with two immunoglobulin light chains, the ratio of the desired heterodimer to the mispaired heterodimer is greater than 1.5:1. In another embodiment, when one immunoglobulin heavy chain of a heterodimer is co-expressed with two immunoglobulin light chains, the ratio of the desired heterodimer to the mispaired heterodimer is greater than 2:1. In another embodiment, when one immunoglobulin heavy chain of a heterodimer is co-expressed with two immunoglobulin light chains, the ratio of the desired heterodimer to the mispaired heterodimer is greater than 3:1. In another embodiment, when one immunoglobulin heavy chain of a heterodimer is co-expressed with two immunoglobulin light chains, the ratio of the desired heterodimer to the mispaired heterodimer is greater than 5:1. In another embodiment, when one immunoglobulin heavy chain of a heterodimer is co-expressed with two immunoglobulin light chains, the ratio of the desired heterodimer to the mispaired heterodimer is greater than 10:1. In another embodiment, when one immunoglobulin heavy chain of a heterodimer is co-expressed with two immunoglobulin light chains, the ratio of the desired heterodimer to the mispaired heterodimer is greater than 25:1. In another embodiment, when one immunoglobulin heavy chain of a heterodimer is co-expressed with two immunoglobulin light chains, the ratio of the desired heterodimer to the mispaired heterodimer is greater than 50:1.

A.4 Thermal Stability of Heterodimers

In one embodiment, each heterodimer of the heterodimer pair according to the invention has a thermal stability that is comparable to that of a heterodimer comprising the same immunoglobulin heavy and light chains but without the amino acid modifications to the $C_{H1}$, $C_L$, $V_H$, or $V_L$ domains described herein. In one embodiment, thermal stability is determined by measurement of melting temperature, or Tm. Thus, in one embodiment, the thermal stability of a heterodimer according to the invention is within about 10° C. of that of a heterodimer comprising the same immunoglobulin heavy and light chains without the amino acid modifications to the $C_{H1}$, $C_L$, $V_H$, or $V_L$ domains described herein. Thus, in one embodiment, the thermal stability of a heterodimer according to the invention is within about 5° C. of that of a heterodimer comprising the same immunoglobulin heavy and light chains without the amino acid modifications to the $C_{H1}$, $C_L$, $V_H$, or $V_L$ domains described herein. In another embodiment, the thermal stability of a heterodimer according to the invention is within about 3° C. of that of a heterodimer comprising the same immunoglobulin heavy and light chains without the amino acid modifications to the $C_{H1}$, $C_L$, $V_H$, or $V_L$ domains described herein. In another embodiment, the thermal stability of a heterodimer according to the invention is within about 2° C. of that of a heterodimer comprising the same immunoglobulin heavy and light chains without the amino acid modifications to the $C_{H1}$, $C_L$, $V_H$, or $V_L$ domains described herein. In another embodiment, the thermal stability of a heterodimer according to the invention is within about 1.5° C. of that of a heterodimer comprising the same immunoglobulin heavy and light chains without the amino acid modifications to the $C_{H1}$, $C_L$, $V_H$, or $V_L$ domains described herein. In another embodiment, the thermal stability of a heterodimer according to the invention is within about 1° C. of that of a heterodimer comprising the same immunoglobulin heavy and light chains without the amino acid modifications to the $C_{H1}$, $C_L$, $V_H$, or $V_L$ domains described herein. In another embodiment, the thermal stability of a heterodimer according to the invention is within about 0.5° C. of that of a heterodimer comprising the same immunoglobulin heavy and light chains without the amino acid modifications to the $C_{H1}$, $C_L$, $V_H$, or $V_L$ domains described herein. In another embodiment, the thermal stability of a heterodimer according to the invention is within about 0.25° C. of that of a heterodimer comprising the same immunoglobulin heavy and light chains without the amino acid modifications to the $C_{H1}$, $C_L$, $V_H$, or $V_L$ domains described herein.

A.5 Affinity of Heterodimers for Antigen

In one embodiment, each heterodimer of the heterodimer pair has an affinity for its respective antigen that is the same or comparable to that of a heterodimer comprising the same immunoglobulin heavy and light chains but without the amino acid modifications to the $C_{H1}$, $C_L$, $V_H$, or $V_L$ domains described herein. In one embodiment, a heterodimer of the heterodimer pair has an affinity for its respective antigen that is within about 50 fold, or one order of magnitude, of that of a heterodimer comprising the same immunoglobulin heavy and light chains without the amino acid modifications to the $C_{H1}$, $C_L$, $V_H$, or $V_L$ domains described herein. In one embodiment, a heterodimer of the heterodimer pair has an affinity for its respective antigen that is within about 25 fold, or one order of magnitude, of that of a heterodimer comprising the same immunoglobulin heavy and light chains without the amino acid modifications to the $C_{H1}$, $C_L$, $V_H$, or $V_L$ domains described herein. In one embodiment, a heterodimer of the heterodimer pair has an affinity for its respective antigen that is within about 10 fold, or one order of magnitude, of that of a heterodimer comprising the same immunoglobulin heavy and light chains without the amino acid modifications to the $C_{H1}$, $C_L$, $V_H$, or $V_L$ domains described herein. In another embodiment, a heterodimer of the heterodimer pair has an affinity for its respective antigen that is within about 5 fold of that of a heterodimer comprising the same immunoglobulin heavy and light chains without the amino acid modifications to the $C_{H1}$, $C_L$, $V_H$, or $V_L$ domains described herein. In another embodiment, a heterodimer of the heterodimer pair has an affinity for its respective antigen that is within about 2.5 fold of that of a heterodimer comprising the same immunoglobulin heavy and light chains without the amino acid modifications to the $C_{H1}$, $C_L$, $V_H$, or $V_L$ domains described herein. In another embodiment, a heterodimer of the heterodimer pair has an affinity for its respective antigen that is within about 2 fold of that of a heterodimer comprising the same immunoglobulin heavy and light chains without the amino acid modifications to the $C_{H1}$, $C_L$, $V_H$, or $V_L$ domains described herein. In another embodiment, a heterodimer of the heterodimer pair has an affinity for its respective antigen that is within about 1.5 fold of that of a heterodimer comprising the same immunoglobulin heavy and light chains without the amino acid modifications to the $C_{H1}$, $C_L$, $V_H$, or $V_L$ domains described herein. In another embodiment, a heterodimer of the heterodimer pair has an affinity for its respective antigen that is within about the same as that of a heterodimer comprising the same immunoglobulin heavy and light chains without the amino acid modifications to the $C_{H1}$, $C_L$, $V_H$, or $V_L$ domains described herein.

A.6 Combination with Other Platforms

It is contemplated that additional amino acid modifications can be made to the immunoglobulin heavy chains in order to increase the level of preferential pairing, and/or the thermal stability of the heterodimer pairs. For example, additional amino acid modifications can be made to the immunoglobulin heavy chain Fc domain in order to drive preferential pairing between heterodimer pairs relative to homodimer pairs. Such amino acid modifications are known in the art and include, for example, those described, in US Patent Publication No. 2012/0149876. Alternatively, alternate strategies for driving preferential pairing between heterodimer pairs relative to homodimer pairs such as, for example, "knobs into holes", charged residues with ionic interactions, and strand-exchange engineered domain (SEED) technologies can also be employed. The latter strategies have been described in the art and are reviewed in Klein et al, supra.

A.7 Additional Optional Modifications

In one embodiment, the immunoglobulin heavy and light chains of the heterodimer pairs according to the invention may be further modified (i.e., by the covalent attachment of various types of molecules) such that covalent attachment does not interfere with the preferential pairing between heavy chain and light chains or affect the ability of the heterodimer to bind to its antigen, or affect its stability. Such modification include, for example, but not by way of limitation, glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc.

In another embodiment, the immunoglobulin heavy and light chains of the heterodimer pairs according to the invention may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), *pseudomonas* exotoxin, cholera toxin, or diphtheria toxin; a protein such as tumor necrosis factor, .alpha.-interferon, .beta.-interferon, nerve growth factor, platelet derived growth factor, tissue plasminogen activator, an apoptotic agent, e.g., TNF-.alpha., TNF-.beta., AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, in an alternate embodiment, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

In some embodiments, the immunoglobulin heavy and light chains of the heterodimer are expressed as fusion proteins comprising a tag to facilitate purification and/or testing etc. As referred to herein, a "tag" is any added series of amino acids which are provided in a protein at either the C-terminus, the N-terminus, or internally that contributes to the identification or purification of the protein. Suitable tags include but are not limited to tags known to those skilled in the art to be useful in purification and/or testing such as albumin binding domain, His tag, FLAG tag, glutathione-s-transferase, haemaglutinin (HA) and maltose binding protein. Such tagged proteins may also be engineered to comprise a cleavage site, such as a thrombin, enterokinase or factor X cleavage site, for ease of removal, of the tag before, during or after purification.

In some embodiments, the cysteine residues at the bottom of the Fab domain (position 219) in the light and heavy chain that form an interchain disulphide bond can be modified to serine.

B. Methods of Preparing Heterodimer Pairs

As described above, the heterodimer pairs according to the invention comprise a first heterodimer and a second heterodimer, each heterodimer comprising an immunoglobulin heavy chain or fragment thereof having at least a $V_H$ and $C_{H1}$ domain, and an immunoglobulin light chain having a $V_L$ domain and a $C_L$ domain. The immunoglobulin heavy chains and immunoglobulin light chains of the heterodimer can readily be prepared using recombinant DNA technology known in the art. Standard techniques such as, for example, those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Short Protocols in Molecular Biology (Ausubel et al., John Wiley and Sons, New York, 4th ed., 1999); and Glick and Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression. Alternatively, the heterodimers and heterodimer pairs according to the invention can be chemically synthesized.

The nucleic acid and amino acid sequences of the immunoglobulin heavy and light chains of the antibodies from which the heterodimers are derived are either known in the art or can be readily determined using nucleic acid and/or protein sequencing methods. Methods of genetically fusing the tags described herein to the immunoglobulin heavy and/or light chains are known in the art, and some are described below and in the Examples.

For example, methods of expressing and co-expressing immunoglobulin heavy and light chains in a host cell are well known in the art. In addition, methods of tagging heavy chains and/or light chains using recombinant DNA technology are also well known in the art.

Expression vectors and host cells suitable for expression of the heavy and light chains are also well known in the art as described below.

B.1 Vectors and Host Cells

Recombinant expression of heavy and light chains requires construction of an expression vector containing a polynucleotide that encodes the heavy or light chain (e.g., antibody, or fusion protein). Once a polynucleotide encoding the heavy or light chain has been obtained, the vector for the production of the heavy or light chain may be produced by recombinant DNA technology using techniques well known in the art. Thus, methods for preparing a protein by expressing a polynucleotide containing the heavy or light chain encoding nucleotide sequence are described herein. Methods that are well known to those skilled in the art can be used to construct expression vectors containing heavy or light chain coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding heavy or light chains, operably linked to a promoter.

The expression vector is transferred to a host cell by conventional techniques and the transfected cells are then cultured by conventional techniques to produce the modified heavy or light chains for use in the method of the invention. In specific embodiments the heavy and light chains for use in the method are co-expressed in the host cell for expression of the entire immunoglobulin molecule, as detailed below.

A variety of host-expression vector systems may be utilized to express the modified heavy and light chains. Such host-expression systems represent vehicles by which the coding sequences of interest may be produced and subsequently purified, but also represent cells which may, when transformed or transfected with the appropriate nucleotide coding sequences, express the modified heavy and light chains in situ. These include but are not limited to microorganisms such as bacteria (e.g., *E. coli* and *B. subtilis*) transformed with recombinant bacteriophage DNA, plasmid DNA or cosmid DNA expression vectors containing the modified heavy and light chain coding sequences; yeast (e.g., *Saccharomyces Pichia*) transformed with recombinant yeast expression vectors containing modified heavy and light chain coding sequences; insect cell systems infected with recombinant virus expression vectors (e.g., baculovirus) containing modified heavy and light chain coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing modified heavy and light chain coding sequences; or mammalian cell systems (e.g., COS, CHO, BHK, HEK-293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of modified heavy and light chains, which is a recombinant antibody or fusion protein molecules. For example, mammalian cells such as Chinese hamster ovary cells (CHO), in conjunction with a promoter such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding the immunoglobulin heavy and light chains of each heterodimer is regulated by a constitutive promoter, inducible promoter or tissue specific promoter.

In mammalian host cells, a number of viral-based expression systems may be utilized. In cases where an adenovirus is used as an expression vector, the modified heavy and light chain coding sequences of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the modified heavy and light chains in infected hosts (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of the immunoglobulin heavy and light chains of the heterodimers may be controlled by any promoter or enhancer element known in the art. Promoters which may be used to control the expression of the gene encoding modified heavy and light chains (e.g., antibody or fusion protein) include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78.1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al, 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, HEK-293, 3T3, W138, NSO, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321 N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines that stably express the modified heavy and light chains of the invention (e.g., antibody or fusion protein) may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

B.2 Co-Expression of Heavy Chains and Light Chains

The immunoglobulin heavy chains and light chains of the heterodimer pairs according to the invention are co-expressed in mammalian cells, as noted above. In one embodiment, one heavy chain is co-expressed with two different light chains in a co-expression set as described above, where the heavy chain preferentially pairs with one of the two light chains. In another embodiment, two heavy chains are co-expressed with two different light chains, where each heavy chain preferentially pairs with one of the light chains.

C. Testing of Heterodimer Pairs

As described above, at least one heterodimer of the heterodimer pairs according to the invention comprises one or more amino acid modifications to their immunoglobulin heavy and/or immunoglobulin light chains such that when the two heavy chains and two light chains of the heterodimer pair are co-expressed in a mammalian cell, the heavy chain of the first heterodimer preferentially pairs with one of the light chains rather than the other. Likewise, the heavy chain of the second heterodimer preferentially pairs with the second light chain rather than the first. The degree of preferential pairing can be assessed, for example, by using the methods described below. The affinity of each heterodimer of the heterodimer pair for its respective antigen can be tested as described below. The thermal stability of each heterodimer of the heterodimer pair can also be tested as described below.

C.1 Methods to Measure Preferential Pairing

LCCA

In one embodiment, preferential pairing between immunoglobulin heavy and light chains is determined by performing a Light Chain Competition Assay (LCCA). The method allows quantitative analysis of the pairing of heavy chains with specific light chains within the mixture of co-expressed proteins and can be used to determine if one particular immunoglobulin heavy chain selectively associates with either one of two immunoglobulin light chains when the heavy chain and light chains are co-expressed. The method is briefly described as follows: At least one heavy chain and two different light chains are co-expressed in a cell, in ratios such that the heavy chain is the limiting pairing reactant; optionally separating the secreted proteins from the cell; separating the immunoglobulin light chain polypeptides bound to heavy chain from the rest of the secreted proteins to produce an isolated heavy chain paired fraction; detecting the amount of each different light chain in the isolated heavy chain fraction; and analyzing the relative amount of each different light chain in the isolated heavy chain fraction to determine the ability of the at least one heavy chain to selectively pair with one of the light chains.

The method provides reasonable throughput and is robust (i.e. insensitive to minor changes in operation, such as user or flow rate) and accurate. The method provides a sensitive assay that can measure the effects of small variations in the protein sequences. Promiscuous protein—protein; domain-domain; chain -chain interactions over large surface areas usually require multiple mutations (swaps) in order to introduce selectivity. The protein products do not need to be isolated and purified which enables more efficient screening. Further details regarding an embodiment of this method are described in the Examples.

Alternative Methods to Determine Preferential Pairing

Alternative methods for detecting preferential pairing include using LC-MS (Liquid chromatography—Mass spectrometry) to quantify the relative heterodimer populations including each light chain using differences in their molecular weight to identify each distinct species. An antigen activity assay could also be used to quantify relative heterodimer populations containing each light chain whereby the degree of binding measured (relative to controls) would be used to estimate each respective heterodimer population.

C.2 Thermal Stability

The thermal stability of the heterodimers can be determined according to methods known in the art. The melting temperature of each heterodimer is indicative of its thermal stability. The melting point of the heterodimer may be measured using techniques such as differential scanning calorimetry (Chen et al (2003) Pharm Res 20:1952-60; Ghirlando et al (1999) Immunol Lett 68:47-52). Alternatively, the thermal stability of the heterodimer may be measured using circular dichroism (Murray et al. (2002) J. Chromatogr Sci 40:343-9).

C.3 Affinity for Antigen

The binding affinity of the heterodimers for their respective antigens and the off-rate of the interaction can be determined by competitive binding assays according to methods well known in the art. One example of a competitive binding assay is a radioimmunoassay comprising the incubation of labeled antigen (e.g., 3H or 125I with a molecule of interest (e.g., heterodimers of the present invention) in the presence of increasing amounts of unlabeled antigen, and the detection of the molecule bound to the labeled ligand. The affinity of the heterodimer of the present invention for the antigen and the binding off-rates can be determined from the saturation data by Scatchard analysis.

The kinetic parameters of a heterodimer according to the invention may also be determined using surface plasmon resonance (SPR) based assays known in the art (e.g., BIAcore kinetic analysis). For a review of SPR-based technology see Mullet et al., 2000, Methods 22: 77-91; Dong et al., 2002, Review in Mol. Biotech., 82: 303-23; Fivash et al., 1998, Current Opinion in Biotechnology 9: 97-101; Rich et al., 2000, Current Opinion in Biotechnology 11: 54-61. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention.

D. Pharmaceutical Compositions

The present invention also provides pharmaceutical compositions comprising the heterodimers or heterodimer pairs. Such compositions comprise a therapeutically effective amount of the heterodimer or heterodimer pair, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the heterodimer or heterodimer pair is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

E. Uses of Heterodimer Pairs

As described above, the heterodimer pairs according to the invention comprises a first heterodimer and a second heterodimer, where the immunoglobulin heavy chain and the immunoglobulin light chain of each heterodimer is derived or engineered from a known therapeutic antibody or from a known antibody that binds a molecule. Thus, it is contemplated that heterodimers derived or engineered from these antibodies could be used for the treatment or prevention of the same disease, disorder, or infection that the known therapeutic antibody or known antibody can be used for.

Thus, in one embodiment, heterodimer pairs according to the invention that comprise a heterodimer with heavy and light chains derived from a therapeutic antibody that can be used for the treatment and/or prevention of cancer and related disorders, can also be used for the treatment and/or prevention of cancer and related disorders.

In another embodiment, heterodimer pairs according to the invention that comprise a heterodimer with heavy and light chains derived from a therapeutic antibody that can be used for preventing, treating, or managing the symptoms of an inflammatory disorder in a subject, can also be used for preventing, treating, or managing the symptoms of an inflammatory disorder in a subject.

In another embodiment, heterodimer pairs according to the invention that comprise a heterodimer with heavy and light chains derived from a therapeutic antibody that can be used for the treatment or prevention of autoimmune disease or inflammatory disease in a subject, can also be used for the treatment or prevention of autoimmune disease or inflammatory disease in a subject.

In another embodiment, heterodimer pairs according to the invention that comprise a heterodimer with heavy and light chains derived from a therapeutic antibody that can be used for the treatment or prevention of an infectious disease in a subject, can also be used for the treatment or prevention of an infectious disease in a subject.

In another embodiment, heterodimer pairs according to the invention that comprise a heterodimer with heavy and light chains derived from a therapeutic antibody that can be used for the treatment of vascular disease in a subject, can also be used for the treatment of vascular disease in a subject.

In another embodiment, the heterodimer pairs according to the invention may also be advantageously utilized in combination with other therapeutic agents known in the art for the treatment or prevention of a cancer, autoimmune disease, inflammatory disorders or infectious diseases. In a specific embodiment, the heterodimer pairs according to the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The heterodimer pairs according to the invention may also be advantageously utilized in combination with one or more drugs used to treat a disease, disorder, or infection such as, for example anti-cancer agents, anti-inflammatory agents or anti-viral agents.

F. Kits

The present invention additionally provides for kits comprising one or more heterodimer pairs. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the heterodimer pairs.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, nasal spray device, syringe, pipette, forceps, measured spoon, eye dropper or similar medically approved delivery vehicle.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

Example 1: Preparation of Constructs Encoding D3H44 IgG Heavy Chains and D3H44 IgG Light Chains The heavy and light chains of the anti-tissue factor antibody D3H44 for use in the co-expression sets described herein were prepared as follows. D3H44 Fab light (AJ308087.1) and heavy (AJ308086.1) chain sequences were taken from GenBank (www.ncbi.nlm.nih.gov/genbank/), gene synthesized and codon optimized for mammalian expression. Light chain vector inserts, consisting of 5'-EcoRI cutsite—HLA-A signal peptide—HA or FLAG tag—Light chain clone—TGA stop—BamH1 cutsite-3', were ligated into a pTT5 vector (Durocher Y et al., Nucl. Acids Res. 2002; 30, No. 2 e9). The resulting vector+insert were sequenced to confirm correct reading frame and sequence of the coding DNA. Likewise, heavy chain vector inserts, consisting of 5'-EcoR1cutsite—HLA-A signal peptide—heavy chain clone—$ABD_2$-$His_6$tag—TGA stop—BamH1 cutsite-3', were ligated into a pTT5 vector (ABD; albumin binding domain). The resulting vector+insert were also sequenced to confirm correct reading frame and sequence of the coding DNA.

Example 2: Assessment of Preferential Pairing of Heterodimers in Co-Expression Sets Comprising Variable Domain Modifications in D3H44 IgG Light and/or Heavy Chains The ability of heterodimers to preferentially pair in co-expression sets comprising D3H44 heavy and light chains with modified $V_L$ and/or $V_H$ domains was determined and the results are shown in FIG. 1. One D3H44 heavy chain construct was co-expressed with two unique D3H44 light chain constructs and the relative light chain pairing specificity (e.g. H1_L1:H1_L2) was determined from a competition assay-SPR screen (Column entitled "Competition assay screen results" in FIG. 1). Selected heterodimer hits were confirmed via a modified competition assay verification where DNA ratios of L1:L2 were varied by 40:60, 50:50 and 60:40 during transfection (Column entitled "Competition assay verification results" in FIG. 1). Heavy chain (HC) was kept in limiting quantities (i.e. HC<L1+L2) for both competition assay screens and verifications. The methods were carried out as follows.

Transfection Method

Co-expression sets comprising one heavy chain and two light chain constructs prepared as described in Example 1 were transfected into CHO-3E7 cells as follows. CHO-3E7 cells were cultured at 37° C. in FreeStyle™ F17 medium (Invitrogen cat #A-1383501) supplemented with 4 mM glutamine and 0.1% Pluronic F-68 (Invitrogen cat #24040-032). Two million cells (CHO-3E7) in 2 ml of growth medium were transfected with a total of 2 ug DNA using PEI-pro (Polyplus cat #115-010) at a DNA:PEI ratio of 1:2.5. Twenty-four hours after the addition of the DNA-PEI mixture, the cells were transferred to 32° C. Supernatants were tested for expression on day 7 by non-reducing SDS-PAGE analysis followed by Coommassie blue staining to visualize the bands. HC: LC ratios are as indicated in Table 7.

TABLE 7

| HC:L1:L2# ratio | Experiment | DNA quantity used for transfection (ng) | | | |
|---|---|---|---|---|---|
| | | HC | LC1 | LC2 | Stuffer^ DNA |
| 50:50:50 | Competition assay screen | 333 | 333 | 333 | 1000 |
| 50:50:50 | Competition assay verification | 333 | 333 | 333 | 1000 |
| 50:40:60 | Competition assay verification | 333 | 266 | 400 | 1000 |
| 50:50:50 | Competition assay verification | 333 | 333 | 333 | 1000 |
| 50:60:40 | Competition assay verification | 333 | 400 | 266 | 1000 |

HC: Heavy chain,
L1: Light chain 1,
L2: Light chain 2
^Stuffer DNA: pTT5 vector without a DNA insert.

Competition Assay SPR Method

The degree of preferential D3H44 light chain pairing to D3H44 heavy chain in co-expression sets was assessed using an SPR-based readout of unique epitope tags located at the N-terminus of each light chain.

Surface Plasmon Resonance (SPR) Supplies.

GLM sensorchips, the Biorad ProteOn amine coupling kit (1-ethyl-3-(3-dimethylaminopropyl) carbodiimide hydrochloride (EDC), N-hydroxysulfosuccinimide (sNHS) and ethanolamine), and 10 mM sodium acetate buffers were purchased from Bio-Rad Laboratories (Canada) Ltd. (Mississauga, ON). Recombinant Her-2 protein was purchased from eBioscience (San Diego, CA). 4-(2-hydroxyethyl)-1-piperazineethanesulfonic acid (HEPES) buffer, ethylenediaminetetraacetic acid (EDTA), and NaCl were purchased from Sigma-Aldrich (Oakville, ON). 10% Tween 20 solution was purchased from Teknova (Hollister, CA).

SPR Biosensor Assays.

All surface plasmon resonance assays were carried out using a BioRad ProteOn XPR36 instrument (Bio-Rad Laboratories (Canada) Ltd. (Mississauga, ON)) with PBST running buffer (PBS Teknova Inc with 0.05% Tween20) at a temperature of 25° C. The anti-penta His capture surface was generated using a GLM sensorchip activated by a 1:5 dilution of the standard BioRad sNHS/EDC solutions injected for 140 s at 100 μL/min in the analyte (horizontal) direction. Immediately after the activation, a 25 μg/mL solution of anti-penta His antibody (Qiagen Inc.) in 10 mM NaOAc pH 4.5 was injected in the analyte (vertical) direction at a flow rate of 25 μL/min until approximately 3000 resonance units (RUs) were immobilized. Remaining active groups were quenched by a 140 s injection of 1M ethanolamine at 100 μL/min in the analyte direction, and this also ensures mock-activated interspots are created for blank referencing.

The screening of the heterodimers for binding to the anti-FLAG (Sigma Inc.) and anti-HA (Roche Inc.) monoclonal antibodies occurred in two steps: an indirect capture of the heterodimers onto the anti-penta His surface in the ligand direction followed by an anti-FLAG and anti-HA injection in the analyte direction. Firstly, one buffer injection for 30 s at 100 uL/min in the ligand direction was used to stabilize the baseline. For each heterodimer capture, unpurified heterodimers in cell-culture media were diluted to 4% in PBST. One to five heterodimers or controls (i.e. controls containing either !00% HA-light chain or 100% FLAG-light chain) were simultaneously injected in individual ligand channels for 240 s at flow 25 μL/min. This resulted in a saturating heterodimer capture of approximately 300 to 400 RUs onto the anti-penta His surface. The first ligand channel was left empty to use as a blank control if required. This heterodimer capture step was immediately followed by two buffer injections in the analyte direction to stabilize the baseline, and then 5 nM anti-FLAG and 5 nM anti-HA were each injected in duplicate at 50 μL/min for 120 s with a 180 s dissociation phase, resulting in a set of binding sensorgrams with a buffer reference for each of the captured heterodimer. Where possible, the antigen to which the heterodimer binds can also be injected over the last remaining analyte channel as an activity control. The heterodimers were regenerated by an 18 s pulse of 0.85% phosphoric acid for 18 s at 100 μL/min to prepare the anti-penta His surface for the next injection cycle. Sensorgrams were aligned and double-referenced using the buffer blank injection and interspots, and the resulting sensorgrams were analyzed using ProteOn Manager software v3.0.

The total percentage of L1 and L2 should, theoretically, add up to 100%. In practice, it was observed for some variants that the total amount of L1 and L2 added up to significantly less than 100%. This discrepancy in total light chain percentage is believed to be due in part to the occurrence of variable non-specific binding during initial heterodimer capture on the SPR chip.

Example 3: Assessment of Preferential Pairing of Heterodimers in Co-Expression Sets Comprising Constant ($C_L$ or $C_{H1}$) Domain Modifications in D3H44 IgG Light and/or Heavy Chains The ability of heterodimers to preferentially pair in co-expression sets comprising D3H44 heavy and light chains with modified $C_L$ and/or $C_{H1}$ domains was determined as described for heterodimers with variable domain modifications in Example 2, and the results are shown in FIG. 2. One D3H44 heavy chain construct was co-expressed with two unique D3H44 light chain constructs and the relative light chain pairing specificity (e.g. H1_L1:H1_L2) was determined from a competition assay-SPR screen (Column entitled "Competition assay screen results" in FIG. 2). Selected heterodimer hits were confirmed via a modified competition assay verification where DNA ratios of L1:L2 were varied by 40:60, 50:50 and 60:40 during transfection (Column entitled "Competition assay verification results" in FIG. 2). As described in Example 2, heavy chain (HC) was kept in limiting quantities (i.e. HC<L1+L2) for both competition assay screens and verifications. Assessment of preferential pairing was carried out as described in Example 2.

Example 4: Scale Up for Biophysical Characterization

Selected heterodimers, both paired and mispaired, were scaled up (typically to 50 ml) and purified as follows in order to test for thermal stability and antigen binding. Heterodimers HD100-HD115, as shown in FIG. 3 were expressed and purified. The heavy and light chain of each heterodimer was expressed in 50 ml cultures of CHO-3E7 cells under the culture conditions described above. Cells were centrifuged and heterodimers purified by loading the supernatant on Fractogel column charged with Nickel as described below. Purification on Fractogel Column Charging with Nickel (his)

Charging the column with Nickel: Sequentially wash with 5 column volumes (CV) of 0.5 M NaCl (no pH adjustment), followed by 4 CV 200 mM of $NiCl_2$ (Nickel) and 2 CV of 0.5 M NaCl pH 5.0. Sample loading and elution: Equilibrate column with 10 CV PBS. Load sample and wash with 10 CV of wash buffer #1 (50 mM sodium phosphate pH 7.0, 300 mM NaCl) followed by 10 CV of wash buffer #2 (50 mM sodium phosphate pH 7.0, 300 mM NaCl, 25 mM Imidazole) to remove impurities bound to the column. The heterodimers were eluted in fractions with wash buffer #1+300 mM Imidazole. The protein content of each fraction was tested by Bradford protein assay. Fractions containing protein were pooled. The purified heterodimers were then assayed for antigen binding and thermal stability as described in Example 5.

Example 5: Thermal Stability and Antigen Affinity Measurements of Heterodimers

The thermal stability and antigen affinity of selected heterodimer pairs was measured in order to compare these features with that of wild type, unmodified heavy chain-light chain pair. Correctly paired and mispaired heterodimers from co-expression sets were individually scaled up, purified (i.e. His tag affinity purification) and assessed for thermal stability and antigen binding as described below. The results are shown in FIG. 3.

Measurement of Thermal Stability

The thermal stability of selected heterodimer pairs was measured using differential scanning calorimetry (DSC) as follows.

Each heterodimer was purified as described in Example 3 and diluted to 0.2 mg/mL in PBS, and a total of 400 µL was used for DSC analysis with a VP-Capillary DSC (GE Healthcare). At the start of each DSC run, 5 buffer blank injections were performed to stabilize the baseline, and a buffer injection was placed before each heterodimer injection for referencing. Each sample was scanned from 20 to 100° C. at a 60° C./hr rate, with low feedback, 8 sec filter, 5 min preTstat, and 70 psi nitrogen pressure. The resulting thermograms were referenced and analyzed using Origin 7 software.

Thermal unfolding curves for the heterodimers tested are shown in FIG. 4. The results indicate that the correctly paired heterodimer (from a design perspective) is usually significantly more stable than the intended mispaired heterodimer (e.g. HD107 versus HD108). In addition, many of the correctly paired heterodimer exhibit a thermal stability close to wild-type Fab (e.g. HD114).

Measurement of Antigen Affinity

The affinity of the heterodimer pairs for antigen (tissue factor extracellular domains) was measured using surface plasmon resonance (SPR) assays. All surface plasmon resonance assays were carried out using a BioRad ProteOn XPR36 instrument (Bio-Rad Laboratories (Canada) Ltd. (Mississauga, ON)) with PBST running buffer (PBS Teknova Inc with 0.05% Tween20) at a temperature of 25° C. A purified tissue factor (TF) surface was generated using a GLM sensorchip activated by a 1:10 dilution of the standard BioRad sNHS/EDC solutions injected for 140 s at 100 µL/min in the ligand (vertical) direction. Immediately after the activation, a 25 µg/mL solution of TF in 10 mM NaOAc pH 4.5 was injected in the ligand direction at a flow rate of 25 µL/min until approximately 1000 resonance units (RUs) were immobilized (or enough for a 100 RU maximum response when flowing 60 nM FAB). Remaining active groups were quenched by a 140 s injection of 1M ethanolamine at 100 µL/min in the analyte direction. For each injection series, two buffer blank injections in the horizontal injection preceded the purified heterodimer. A 3-fold dilution series of each heterodimer (60 nM, 20 nM, 6.7 nM, 2.2 nM) with a blank buffer control was simultaneously injected at 50 µL/min for 120 s with a 20 minute dissociation, resulting in a set of binding sensorgrams with a buffer reference for each of the heterodimers. The heterodimer:TF complexes on the SPR surface were regenerated by an 18 s pulse of 0.85% phosphoric acid for 18 s at 100 µL/min to prepare the TF surface for the next injection cycle. Sensorgrams were aligned and double-referenced using the buffer blank injection and interspots, and the resulting sensorgrams were analyzed using a 1:1 binding model within the ProteOn Manager software v3.0.

The results indicate that the correctly paired heterodimer (from a design perspective) exhibits a range of affinities for antigen, with some designs showing wild-type like binding affinity for antigen (e.g. HD107 and HD114).

Example 6: Size Exclusion Chromatography (SEC) Profiles of Wild-Type Tagged D3H44 Heterodimers and a Representative Sample of Individual Preferentially Paired Heterodimers Wild-type D3H44 heterodimer (one heavy chain and one light chain) with a C-terminus ABD2-$His_6$ tag on the heavy chain and an N-terminus FLAG tag on the light chain was expressed and purified according to methods known in the art and similar to those described in Examples 1 and 4. Preferentially or correctly paired heterodimers from co-expression sets (heterodimers HD100, HD105, and HD107, shown in FIG. 3) were individually scaled up and purified via His tag affinity purification and SEC as described in Example 4.

SEC was carried out as follows. Heterodimer samples were separated using a Superdex 200 HR 10/30 Pharmacia (GE Healthcare) column mounted on a Pharmacia (GE Healthcare) ÄKTA Purifier system. Heterodimer samples (0.3-0.5 ml) in PBS were manually loaded into a 0.5 ml loop filled with PBS. Samples were than automatically injected onto the column and resolved at 0.5 ml/min with a 1CV elution volume. Protein elution was monitored at $OD_{280}$ and collected in 1 ml fractions.

As shown in FIG. 5A-D, correctly paired heterodimers displayed SEC profiles close to that observed for wild-type heterodimer without amino acid modifications (Main peak

[*]:heterodimer). Equivalent results are obtained when the light chain of the wild-type heterodimer has a N-terminus HA tag.

Example 7: Additional Data Relating to the Stability of Heterodimers

Designs shown in Table 8 were highlighted as combinations of design drivers with improved HC-LC selectivities.

TABLE 8

| Design | Set # | Set # | H1_mutation* | L1_mutation | H2_mutation | L2_mutation |
|---|---|---|---|---|---|---|
| 11 | C525 | C526 | S188L_V190Y | V133S | F174V_P175S_S188G | S176L |
| 12 | V042 | V043 | V37E_F100D | L89R_F98W | WT | WT |
| 13 | C532 | C533 | L143A_D144G_Q179R | Q124E_V133W_Q160E_T180E | K145T_Q179D_S188F | V133A_Q160K_T178R |
| *14 | | | D146G_S186R | Q124E_Q160E_T178D | K145E_D146G_Q179D_S188L | Q124R_Q160K_T178R |
| 15 | C530 | C531 | D146G_Q179R | Q124E_Q160E_T178D | K145T_Q179D_S188L | Q160K_T178R |

*Residue numbering for these designs is the same as noted for Table 10 below.

The majority of the designs retain thermal stability (Tm) and TF binding affinity as shown in Table 9

TABLE 9

| | Tm (° C.) | | TF Binding KD (nM) | | H1 Readout | | H2 Readout | |
|---|---|---|---|---|---|---|---|---|
| Design | H1-L1 Tm | H2-L2 Tm | H1-L1 | H2-L2 | H1-L1 | H1-L2 | H2-L2 | H2-L1 |
| 11 | 74.7 | 73.3 | 0.043 | 0.040 | 83 | 24 | 98 | 1 |
| 12 | 76.2 | 76.0 | | 0.052 | 99 | 10 | 88 | 15 |
| 13 | 67.5 | 71.5 | 0.087 | 0.086 | 104 | 1 | 87 | 14 |
| 14 | | | | | 84 | 1 | 74 | 2 |
| 15 | 70.1 | 76.3 | 0.082 | 0.071 | 93 | 1 | 83 | 24 |

Design 12 consists of WT H2-L2 pairing - the resulting binding affinity is WT
WT Tm of anti-TF Fab is ~76° C. (not shown)

Example 8: Additional Heterodimers and Testing of Same

Additional heterodimer pairs as described in Table 10 were prepared and tested. These heterodimers were designed to increase Fab hotspot coverage and maximize the number of potentially transferable solutions.

TABLE 10

| Design | H1_mutation | L1_mutation | H2_mutation | L2_mutation |
|---|---|---|---|---|
| 26 | A139G_V190A | L135W | A139W_ K145Y_ Q175E | F116A_ S131K_ L135A |
| 27 | A139I_K145T_ D146G_Q179E_ S188G_V190S | F116A_ V133G_S176F_ T178A | S186K_ S188H_ V190G | F118W_ Q124E_ V133S_ S176A_ T178S_ T180E |
| 28 | A139V_K145L_ Q179E_S188G_ V190S | F116A_S131K_ V133G_S176F_ T178A | A139W_ S186K_ S188A | F118W_ V133S_ S176A_ T180E |
| 29 | L143K_D146G | Q124E_V133D | L143E_ K145T | Q124R |
| 30 | D146G_Q179K | Q124E_Q160E_ T180E | L143E_ K145T | Q160K_ T178R |
| 31 | Q39D_A139G_ V190A | Q38R_L135W | Q39R_ A139W | Q38D_ F116A_ L135A |
| 32 | Q39E | Q38R | Q39R | Q38E_F98W |

Residue numbering in Table 10 is according to Kabat.

The stability, ability to bind to target, and the ability to selectively pair for these heterodimers was determined as shown in Table 11.

TABLE 11

| | Tm (° C.) | | TF Binding KD (nM) | | H1 Readout | | H2 Readout | |
|---|---|---|---|---|---|---|---|---|
| Design | H1-L1 Tm | H2-L2 Tm | H1-L1 | H2-L2 | H1-L1 | H1-L2 | H2-L2 | H2-L1 |
| 26 | 67.8 | 73.6 | | | 92 | 1 | 106 | 1 |
| 27 | 71.0 | | | | 67 | 1 | 85 | 12 |
| 28 | | | | | 85 | 4 | 94 | 1 |
| 29 | 64.1 | 68.3 | | | 93 | 1 | 102 | 1 |
| 30 | 67.0 | 75.5 | 0.024 | 0.060 | 96 | 1 | 102 | 1 |
| 31 | 74.3 | | 0.025 | | 106 | 1 | 78 | 1 |
| 32 | | | | | 98 | 1 | 93 | 1 |

WT anti-TF Fab KD = 0.052 nM
WT Tm of anti-TF Fab is ~76° C.

All publications, patents and patent applications mentioned in this specification are herein incorporated by reference into the specification to the same extent as if each individual publication, patent or patent application was specifically and individually indicated to be incorporated herein by reference.

The invention claimed is:

1. An antibody construct comprising at least a first heterodimer and a second heterodimer,
   the first heterodimer comprising a first human or humanized immunoglobulin G (IgG) heavy chain polypeptide (H1) and a first human or humanized immunoglobulin light chain polypeptide (L1), and binding a first epitope,
   the second heterodimer comprising a second human or humanized IgG heavy chain polypeptide (H2) and a second human or humanized immunoglobulin light chain polypeptide (L2), and binding a second epitope,
   H1 and H2 each comprising a heavy chain variable domain (VH domain) and a heavy chain constant domain 1 (CH1 domain), and L1 and L2 each comprising a light chain variable domain (VL domain) and a light chain constant domain (CL domain);
   wherein H1, H2, L1 and/or L2 comprise the following amino acid substitutions at positions identified according to the Kabat numbering system:
   a) H1 comprises amino acid substitutions 37W and 103F, L1 comprises amino acid substitution 98L, H2 comprises amino acid substitution 37I, and L2 comprises amino acid substitution 98W;
   b) H1 comprises amino acid substitutions 37W and 103F, L1 comprises amino acid substitution 98L, H2 comprises no amino acid substitutions that promote preferential pairing, and L2 comprises amino acid substitution 98W;
   c) H1 comprises amino acid substitution 37W, L1 comprises amino acid substitution 98A, H2 comprises amino acid substitution 37I, and L2 comprises amino acid substitution 98W;
   d) H1 comprises amino acid substitution 37W, L1 comprises amino acid substitution 98A, H2 comprises amino acid substitution 37I, and L2 comprises no amino acid substitutions that promote preferential pairing;
   e) H1 comprises no amino acid substitutions that promote preferential pairing, L1 comprises amino acid substitution 98W, H2 comprises amino acid substitution 37W, and L2 comprises amino acid substitution 98A;
   f) H1 comprises no amino acid substitutions that promote preferential pairing, L1 comprises no amino acid substitutions that promote preferential pairing, H2 comprises amino acid substitution 37W, and L2 comprises amino acid substitution 98A;
   g) H1 comprises amino acid substitution 37E, L1 comprises amino acid substitutions 89R and 98T, H2 comprises no amino acid substitutions that promote preferential pairing, and L2 comprises no amino acid substitutions that promote preferential pairing;
   h) H1 comprises amino acid substitutions 37E and 100D, L1 comprises amino acid substitutions 89R and 98W, H2 comprises no amino acid substitutions that promote preferential pairing, and L2 comprises no amino acid substitutions that B promote preferential pairing; or
   i) H1 comprises amino acid substitutions 37E and 100D, L1 comprises amino acid substitutions 89R and 98W, H2 comprises amino acid substitutions 37S and 97K, B and L2 comprises amino acid substitution 98Y;
   and wherein the amino acid substitutions promote preferential pairing of H1 with L1 as compared to L2, and of H2 with L2 as compared to L1, when H1, H2, L1 and L2 are co-expressed in a cell.

2. A pharmaceutical composition comprising the antibody construct according to claim 1 and a pharmaceutically acceptable carrier.

3. A set of polynucleotides encoding the antibody construct according to claim 1.

4. One or more vectors comprising the set of polynucleotides according to claim 3.

5. An isolated prokaryotic or eukaryotic host cell comprising the one or more vectors according to claim 4.

6. A method for preparing the antibody construct according to claim 1, comprising the steps of:
   transforming a host cell with one or more vectors comprising a set of polynucleotides encoding the antibody construct of claim 1;
   culturing the host cell under conditions that allow expression of the antibody construct; and
   recovering the antibody construct from the culture.

7. The antibody construct of claim 1, wherein L1 and/or L2 are kappa light chains.

8. The antibody construct of claim 1, wherein the first heterodimer and the second heterodimer each comprise a full-length IgG heavy chain having an Fc domain.

9. The antibody construct of claim 8, wherein the Fc domain of H1 interacts preferentially with the Fc domain of H2 as compared to forming a homodimer.

10. The antibody construct of claim 1, wherein H1 and H2 are from an IgG1, IgG2, IgG3, or IgG4 antibody.

11. The antibody construct of claim 1, wherein when both L1 and L2 are co-expressed with at least one of H1 and H2, the relative yield of the at least one of H1-L1 and H2-L2 heterodimer pair to that of the corresponding mispaired H1-L2 or H2-L1 heterodimer pair is greater than 50%.

12. The antibody construct of claim 1, wherein the thermal stability as measured by the melting temperature (Tm) of at least one of the first and second heterodimers is within about 10° C. of the Tm of the corresponding heterodimer without the amino acid substitutions.

13. The antibody construct of claim 1, wherein the affinity of each heterodimer for its antigen is within about 50-fold of the affinity of the wild type heterodimer for the antigen.

14. The antibody construct of claim 1, wherein the antibody construct is bispecific.

\* \* \* \* \*